United States Patent [19]

Ishikawa et al.

[11] 4,416,884
[45] Nov. 22, 1983

[54] PIPERAZINYLBENZOHETEROCYCLIC COMPOUNDS

[75] Inventors: Hiroshi Ishikawa; Fujio Tabusa; Kazuyuki Nakagawa, all of Tokushima, Japan

[73] Assignee: Otsuka Pharmaceutical Co., Ltd., Tokyo, Japan

[21] Appl. No.: 195,691

[22] Filed: Oct. 9, 1980

Related U.S. Application Data

[63] Continuation-in-part of Ser. No. 28,788, Apr. 10, 1979, abandoned.

[30] Foreign Application Priority Data

| | | | |
|---|---|---|---|
| Apr. 12, 1978 | [JP] | Japan | 53-43624 |
| Sep. 7, 1978 | [JP] | Japan | 53-110464 |
| Nov. 16, 1978 | [JP] | Japan | 53-141785 |
| Nov. 24, 1978 | [JP] | Japan | 53-145638 |
| Aug. 31, 1978 | [JP] | Japan | 53-107387 |
| Nov. 6, 1978 | [JP] | Japan | 53-137157 |
| Nov. 17, 1978 | [JP] | Japan | 53-142731 |
| Oct. 11, 1979 | [JP] | Japan | 54-131630 |

[51] Int. Cl.³ ............... A61K 31/495; C07D 401/04
[52] U.S. Cl. .................................. 424/250; 544/361; 544/362; 546/94; 546/152; 546/157; 546/165; 546/171; 546/180
[58] Field of Search ............... 424/250; 544/361, 362

[56] References Cited

U.S. PATENT DOCUMENTS

| | | | |
|---|---|---|---|
| 3,567,727 | 3/1971 | Barber et al. | 544/361 |
| 3,896,131 | 7/1975 | Gerster | 424/258 |
| 3,917,609 | 11/1975 | Gerster | 424/258 |
| 3,969,463 | 7/1976 | Gerster | 424/258 |
| 3,985,882 | 10/1976 | Gerster | 424/258 |
| 4,001,243 | 1/1977 | Gerster | 424/258 |
| 4,014,877 | 3/1977 | Gerster | 544/126 |
| 4,146,719 | 3/1979 | Irikura et al. | 544/363 |

FOREIGN PATENT DOCUMENTS

| | | | |
|---|---|---|---|
| 55-40616 | 3/1980 | Japan | 544/361 |
| 2057440A | 4/1981 | United Kingdom | 544/361 |

Primary Examiner—Donald G. Daus
Assistant Examiner—James H. Turnipseed

Attorney, Agent, or Firm—Sughrue, Mion, Zinn, Macpeak & Seas

[57] ABSTRACT

A piperazinylbenzoheterocyclic compound having antimicrobial properties and represented by the formula (I)

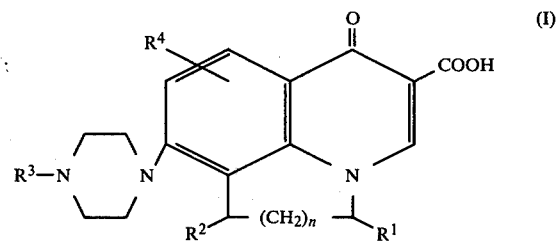

wherein $R^1$ represents hydrogen or lower alkyl; $R^2$ represents hydrogen; $R^3$ represents hydrogen, lower alkyl, lower alkanoyl, lower alkylsulfonyl, phenylalkyl, benzoyl, p-toluenesulfonyl, a group represented by the formula

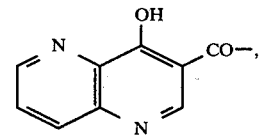

lower alkyl substituted with one to three of halogen and hydroxy, lower alkanoyl substituted with one to seven of halogen, phenylalkyl substituted with one to three of lower alkoxy on the phenyl ring, lower alkylsulfonyl substituted with one to three of halogen, lower alkenyl or lower alkynyl; $R^4$ represents hydrogen or halogen, and n is an integer of 0 or 1, except that when n is 0, $R^1$ and $R^2$ together can represent the atoms necessary to form a cyclohexane ring, and when $R^3$ represents lower alkyl substituted with one to three of halogen and hydroxy, lower alkanoyl substituted with one to seven of halogen, phenylalkyl substituted with one to three of lower alkoxy on the phenyl ring, lower alkylsulfonyl substituted with one to three of halogen, lower alkenyl or lower alkynyl, n is 1.

64 Claims, No Drawings

PIPERAZINYLBENZOHETEROCYCLIC COMPOUNDS

This application is a continuation-in-part application of Ser. No. 28,788, filed Apr. 10, 1979, now abandoned.

BACKGROUND OF THE INVENTION

1. Field of the Invention

This invention relates to certain piperazinylbenzoheterocyclic compounds and to pharmaceutically acceptable salts thereof which are useful as antimicrobial agents, processes for preparing the same, and pharmaceutical compositions containing the piperazinylbenzoheterocyclic compound or salt thereof.

2. Description of the Prior Art

It is known that certain types of polyheterocyclic compounds exhibit antimicrobial activities. For example, U.S. Pat. No. 3,917,609 to Gerster et al. discloses substituted derivatives of 1,2-dihydro-6-oxo-6H-pyrrolo[3,2,1-ij]quinoline which are useful as antimicrobial agents or as intermediates for the preparation of antimicrobial agents.

Also, U.S. Pat. Nos. 3,896,131, 3,985,882, 3,969,463, 4,001,243 and 4,014,877 to Gerster et al. disclose 6,7-dihydro-1-oxo-1H,5H-benzo[ij]quinolizine derivatives having antimicrobial activities.

However, the piperazinylbenzoheterocyclic compounds of the present invention are structurally different from such quinoline and quinolizine compounds.

SUMMARY OF THE INVENTION

Accordingly, one object of the present invention is to provide piperazinylbenzoheterocyclic compounds having antimicrobial activity and low toxicity.

A more particular object of the present invention is to provide piperazinylbenzoheterocyclic compounds having low oral toxicity in comparison to the effective oral dosage thereof.

Another object of the present invention is to provide an antibacterial agent which shows no decrease in activity in the presence of serum.

Still another object of the present invention is to provide an antimicrobial agent which is effective against bacteria which are resistant to conventional antibiotics such as penicillin, ampicillin, streptomycin, etc.

A further object of the present invention is to provide a pharmaceutical composition containing the aforesaid antimicrobial agent or a pharmaceutically acceptable salt thereof in an antimicrobially effective amount.

Still a further object of the present invention is to provide a process for preparing a piperazinylbenzoheterocyclic compound.

Accordingly, the present invention provides a piperazinylbenzoheterocyclic compound represented by the formula (I)

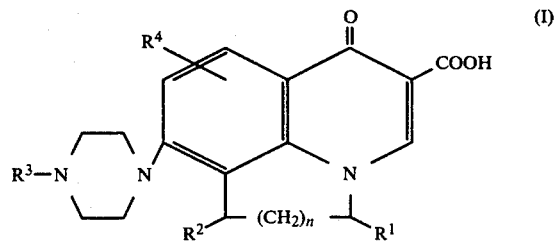

wherein $R^1$ can represent a hydrogen atom or a lower alkyl group; $R^2$ can represent a hydrogen atom; $R^3$ represents a hydrogen atom, a lower alkyl group, a lower alkanoyl group, a lower alkanesulfonyl group, a phenylalkyl group, a benzoyl group, a p-toluenesulfonyl group or a group represented by the formula

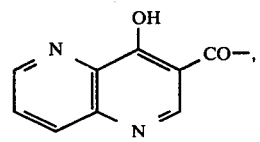

a lower alkyl group substituted with one or more of a halogen group and a hydroxy group, a lower alkanoyl group substituted with one or more halogen groups, a phenylalkyl group substituted with one or more lower alkoxy groups on the phenyl ring, a lower alkanesulfonyl group substituted with one or more halogen groups, a lower alkenyl group, or a lower alkynyl group; $R^4$ represents a hydrogen atom or a halogen group, n is an integer of 0 or 1, except that when n is 0 $R^1$ and $R^2$ together can represent the atoms necessary to form a cyclohexane ring, and when $R^3$ represents a lower alkyl group substituted with one or more of a halogen group and a hydroxy group, a lower alkanoyl group substituted with one or more halogen groups, a phenyl alkyl group substituted with one or more lower alkoxy groups on the phenyl ring, a lower alkanesulfonyl group substituted with one or more halogen groups, a lower alkenyl group or a lower alkynyl group, n is 1; and pharmaceutically acceptable salts thereof.

In another aspect this invention provides a pharmaceutical composition containing a compound according to formula (I) or a pharmaceutically acceptable salt thereof in an antimicrobially effective amount.

Further, this invention provides processes for preparing the compounds of the formula (I) and pharmaceutically acceptable salts thereof.

DETAILED DESCRIPTION OF THE INVENTION

The term "halogen" as used herein includes a chlorine atom, a bromine atom, an iodine atom and a fluorine atom.

The term "lower alkyl" as used herein refers to a straight or branched chain alkyl group having from 1 to 4 carbon atoms, such as a methyl group, an ethyl group, a propyl group, an isopropyl group, a butyl group, a tert-butyl group and the like.

The term "lower alkanoyl" as used herein refers to a straight or branched alkanoyl group having from 1 to 4 carbon atoms, such as a formyl group, an acetyl group, a propanoyl group, a butanoyl group, an isobutanoyl group and the like.

The term "lower alkanesulfonyl" as used herein refers to a straight or branched alkanesulfonyl group having from 1 to 4 carbon atoms, such as a methanesulfonyl group, an ethanesulfonyl group, a propanesulfonyl group, an isopropanesulfonyl group, a butanesulfonyl group, a tert-butanesulfonyl group and the like.

The term "phenylalkyl" as used herein refers to a phenylalkyl group consisting of a phenyl group and a straight or branched alkylene group having from 1 to 4 carbon atoms, such as a benzyl group, a 2-phenylethyl group, a 3-phenylpropyl group, a 4-phenylbutyl group, a 1-phenylethyl group, a 1,1-dimethyl-2-phenylethyl group and the like.

In the above formula (I), the group of the formula

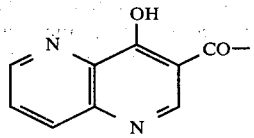

representing $R^3$ may be present as a tautomer, an enol type group (A), i.e., a 4-hydroxy-1,5-naphthyridine-3-carbonyl group, or a keto type group (B), i.e., a 4-oxo-1,4-dihydro-1,5-naphthyridine-3-carbonyl group. This invention includes both enol and keto type tautomers.

The term "lower alkyl group substituted with one or more of a halogen group and a hydroxy group" as used herein refers to a straight or branched chain alkyl group having from 1 to 4 carbon atoms substituted with from 1 to 3 of a halogen group and a hydroxy group, such as a trifluoromethyl group, a trichloromethyl group, a dichloromethyl group, a tribromomethyl group, a 2,2,2-trifluoroethyl group, a 2,2,2-trichloroethyl group, a 2-chloroethyl group, a 1,2-dichloroethyl group, a 3,3,3-trichloropropyl group, a 3-fluoropropyl group, a 4-chlorobutyl group, a 3-chloro-2-methylethyl group, a hydroxymethyl group, a 2-hydroxyethyl group, a 3-hydroxypropyl group, a 2,3-dihydroxypropyl, 4-hydroxybutyl, 2-hydroxypropyl group and the like.

The term "lower alkanoyl group substituted with one or more halogen atoms" as used herein refers to a straight or branched chain alkanoyl group having from 2 to 4 carbon atoms substituted with from 1 to 7 halogen atoms such as trifluoroacetyl group, a trichloroacetyl group, a tribromoacetyl group, a 2,2-dichloropropionyl group, a monochloroacetyl group, a 2-chlorobutyryl group, a pentafluoropropionyl group, a heptafluorobutyryl group and the like.

The term "phenylalkyl group substituted with one or more lower alkoxy group on the phenyl ring" as used herein refers to a phenylalkyl group substituted with from 1 to 3 lower alkoxy group having from 1 to 4 carbon atoms on the phenyl ring consisting of the substituted phenyl group and a straight or branched alkylene group having from 1 to 4 carbon atoms such as a 4-methoxybenzyl group, a 2-isopropoxybenzyl group, a 3,4-dimethoxybenzyl group, a β-3,4-dimethoxhphenethyl group, an α-3,4-dimethoxyphenethyl group, a β-2,3,4-trimethoxyphenethyl group, a 3-(4-ethoxyphenyl)propyl group, a 4-(4-methoxyphenyl)butyl group and the like.

The term "lower alkanesulfonyl group substituted with one or more halogen groups" as used herein refers to a straight or branched chain alkanesulfonyl group having from 1 to 4 carbon atoms substituted with from 1 to 3 halogen atoms such as a trifluoromethanesulfonyl group, a trichloromethanesulfonyl group, a tribromomethanesulfonyl group, a dichloromethanesulfonyl group, a 2,2,2-trifluoroethanesulfonyl group, a 2,2,2-trichloroethanesulfonyl group, a 2-chloroethanesulfonyl group, a 1,2-dichloroethanesulfonyl group, a 3,3,3-trifluoropropanesulfonyl group, a 3,3,3-trichloropropanesulfonyl group, a 3-fluoropropanesulfonyl group, a 4-chlorobutanesulfonyl group, a 3-chloro-2-methylethanesulfonyl group and the like.

The term "lower alkenyl group" as used herein refers to a straight or branched chain alkenyl group having from 2 to 4 carbon atoms such as a vinyl group, an allyl group, a crotyl group, a 1-methylallyl group and the like.

The term "lower alkynyl group" as used herein refers to a straight or branched alkynyl group having 2 to 4 carbon atoms such as an ethynyl group, a 2-propynyl group, a 2-butynyl group, a 1-methyl-2-propynyl group and the like.

The compounds of this invention are particularly effective against bacteria belonging to the genera Streptococcus, Pseudomonas, Enterobacter, etc., and exhibit potent antibacterial activity on those bacteria which are resistant to streptomycin, ampicillin and/or tetracyclin.

Representative examples of compounds according to this invention include the following compounds, which are provided for illustration only, and are not intended to limit the scope of this invention:

8-(1-piperazinyl)-6,7-dihydro-1-oxo-1H,5H-benzo[ij]-quinolizine-2-carboxylic acid 10-chloro-8-(1-piperazinyl)-6,7-dihydro-1-oxo-1H,5H-benzo[ij]quinolizine-2-carboxylic acid 9-chloro-8-(1-piperazinyl)-6,7-dihydro-1-oxo-1H,5H-benzo[ij]quinolizine-2-carboxylic acid 9-fluoro-8-(1-piperazinyl)-6,7-dihydro-1-oxo-1H,5H-benzo[ij]quinolizine-2-carboxylic acid 8-(1-piperazinyl)-5-methyl-6,7-dihydro-1-oxo-1H,5H-benzo[ij]quinolizne-2-carboxylic acid 8-(1-piperazinyl)-5-ethyl-6,7-dihydro-1-oxo-1H,5H-benzo[ij]quinolizine-2-carboxylic acid 8-(1-piperazinyl)-5-butyl-6,7-dihydro-1-oxo-1H,5H-benzo[ij]quinolizine-2-carboxylic acid 8-(4-methyl-1-piperazinyl)-6,7-dihydro-1-oxo-1H,5H-benzo[ij]quinolizine-2-carboxylic acid 8-(4-butyl-1-piperazinyl)-5-methyl-6,7-dihydro-1-oxo-1H,5H-benzo[ij]quinolizine-2-carboxylic acid 8-(4-acetyl-1-piperazinyl)-6,7-dihydro-1-oxo-1H,5H-benzo[ij]quinolizine-2-carboxylic acid 8-(4-isobutyl-1-piperazinyl)-5-methyl-6,7-dihydro-1-oxo-1H,5H-benzo[ij]quinolizine-2-carboxylic acid 8-(4-formyl-1-piperazinyl)-9-fluoro-5-methyl-6,7-dihydro-1-oxo-1H,5H-benzo[ij]quinolizine-2-carboxylic acid 8-(4-benzoyl-1-piperazinyl)-6,7-dihydro-1-oxo-1H,5H-benzo[ij]quinolizine-2-carboxylic acid 8-(4-benzoyl-1-piperazinyl)-5-methyl-6,7-dihydro-1-oxo-1H,5H-benzo[ij]quinolizine-2-carboxylic acid 8-(4-methanesulfonyl-1-piperazinyl)-6,7-dihydro-1-oxo-1H,5H-benzo[ij]quinolizine-2-carboxylic acid 8-(4-tert-butanesulfonyl-1-piperazinyl)-5-methyl-6,7-dihydro-1-oxo-1H,5H-benzo[ij]quinolizine-2-carboxylic acid 8-(4-benzyl-1-piperazinyl)-6,7-dihydro-1-oxo-1H,5H-benzo[ij]quinolizine-2-carboxylic acid 8-[4-(2-phenylethyl)-1-piperazinyl]-5-methyl-6,7-dihydro-1-oxo-1H,5H-benzo[ij]quinolizine-2-carboxylic acid 8-[4-(4-phenylbutyl)-1-piperazinyl]-10-chloro-6,7-dihydro-1-oxo-1H,5H-benzo[ij]quinolizine-2-carboxylic acid 8-(1-piperazinyl)-9-fluoro-5-methyl-6,7-dihydro-1-oxo-1H,5H-benzo[ij]quinolizine-2-carboxylic acid 8-[4-(4-hydroxy-1,5-naphthyridine-3-carbonyl)-1-piperazinyl]-6,7-dihydro-1-oxo-1H,5H-benzo[ij]-quinolizine-2-carboxylic acid 8-[4-(4-hydroxy-1,5-naphthyridine-3-carbonyl)-1-piperazinyl]-5-methyl-6,7-dihydro-1-oxo-1H,5H-benzo[ii]-quinolizine-2-carboxylic acid 8-[4-(4-oxo-1,4-dihydro-1,5-naphthyridine-3-carbonyl)-1-piperazinyl]-6,7-dihydro-1-oxo-1H,5H-benzo[ij]quinolizine-2-carboxylic acid 8-(4-ethyl-1-piperazinyl)-10-fluoro-6,7-dihydro-1-oxo-1H,5H-benzo[ij]quinolizine-2-carboxylic acid 8-(4-propionyl-1-piperazinyl)-9-bromo-5-methyl-6,7-dihydro-1-oxo-1H,5H-benzo[ij]quinolizine-2-carboxylic acid 8-(1-piperazinyl)-10-fluoro-5-methyl-6,7-dihydro-1-oxo-1H,5H-benzo[ij]quinolizine-2-carboxylic acid 8-(4-benzoyl-1-piperazinyl)-9-fluoro-5-methyl-6,7-dihydro-1-oxo-1H,5H-benzo[ij]quinolizine-2-carboxylic acid 8-[4-(p-toluenesulfonyl)-1-piperazinyl]-5-methyl-6,7-dihydro-1-oxo-1H,5H-benzo[ij]quinolizne-2-carboxylic acid 9-(1-piperazinyl)-6-oxo-1,2-dihydro-6H-pyrrolo-[3,2,1-ij]quinoline-5-carboxylic acid 9-(1-piperazinyl)-2-methyl-6-oxo-1,2-dihydro-6H-pyrrolo[3,2,1-ij]quinoline-5-carboxylic acid 9-(1-piperazinyl)-2-ethyl-6-oxo-1,2-dihydro-6H-pyrrolo[3,2,1-ij]quinoline-5-carboxylic acid 9-(1-piperazinyl)-2-isopropyl-6-oxo-1,2-dihydro-6H-pyrrolo[3,2,1-i]quinoline-5-carboxylic acid 9-(1-piperazinyl)-2-butyl-6-oxo-1,2-dihydro-6H-pyrrolo[3,2,1-ij]quinoline-5-carboxylic acid 7-chloro-9-(1-piperazinyl)-6-oxo-1,2-dihydro-6H-pyrrolo[3,2,1-ij]quinoline-5-carboxylic acid 8-fluoro-9-(1-piperazinyl)-6-oxo-1,2-dihydro-6H-pyrrolo[3,2,1-ij]quinoline-5-carboxylic acid 9-(4-methyl-1-piperazinyl)-2-methyl-6-oxo-1,2-dihydro-6H-pyrrolo[3,2,1-ij]quinoline-5-carboxylic acid 9-(4-isopropyl-1-piperazinyl)-6-oxo-1,2-dihydro-6H-pyrrolo[3,2,1-ij]quinoline-5-carboxylic acid 9-(4-acetyl-1-piperazinyl)-2-methyl-6-oxo-1,2-dihydro-6H-pyrrolo[3,2,1-ij]quinoline-5-carboxylic acid 9-(4-butyryl-1-piperazinyl)-6-oxo-1,2-dihydro-6H-pyrrolo[3,2,1-ij]quinoline-5-carboxylic acid 9-(4-formyl-1-piperazinyl)-2-methyl-6-oxo-1,2-dihydro-6H-pyrrolo[3,2,1-ij]quinoline-5-carboxylic acid 9-(4-benzoyl-1-piperazinyl)-2-methyl-6-oxo-1,2-dihydro-6H-pyrrolo[3,2,1-ij]quinoline-5-carboxylic acid 9-(4-methanesulfonyl-1-piperazinyl)-2-methyl-6-oxo-1,2-dihydro-6H-pyrrolo[3,2,1-ij]quinoline-5-carboxylic acid 9-(4-propanesulfonyl-1-piperazinyl)-6-oxo-1,2-dihydro-6H-pyrrolo[3,2,1-ij]quinoline-5-carboxylic acid 9-(4-benzyl-1-piperazinyl)-2-methyl-6-oxo-1,2-dihydro-6H-pyrrolo[3,2,1-ij]quinoline-5-carboxylic acid 9-[4-(4-phenylbutyl)-1-piperazinyl]-6-oxo-1,2-dihydro-6H-pyrrolo[3,2,1-ij]quinoline-5-carboxylic acid 8-fluoro-9-(1-piperazinyl)-2-methyl-6-oxo-1,2-dihydro-6H-pyrrolo[3,2,1-ij]quinoline-5-carboxylic acid 8-chloro-9-(4-acetyl-1-piperazinyl)-2-methyl-6-oxo-1,2-dihydro-6H-pyrrolo[3,2,1-ij]quinoline-5-carboxylic acid 9-[4-(4-hydroxy-1,5-naphthyridine-3-carbonyl)-1-piperazinyl]-2-methyl-6-oxo-1,2-dihydro-6H-pyrrolo-[3,2,1-ij]quinoline-5-carboxylic acid 9-[4-(4-oxo-1,4-dihydro-1,5-naphthyridine-3-carbonyl)-1-piperazinyl]-6-oxo-1,2-dihydro-6H-pyrrolo-[3,2,1-ij]quinoline-5-carboxylic acid 9-(4-ethyl-1-piperazinyl)-8-bromo-2-methyl-6-oxo-1,2-dihydro-6H-pyrrolo[3,2,1-ij]quinoline-5-carboxylic acid 1-(1-piperazinyl)-7a,8,9,10,11,11a-hexahydro-4-oxo-4H-pyrido[3,2,1-jk]carbazole-5-carboxylic acid 3-chloro-1-(piperazinyl)-7a,8,9,10,11,11a-hexahydro-4-oxo-4H-pyrido[3,2,1-jk]carbazole-5-carboxylic acid 2-fluoro-1-(piperazinyl)-7a,8,9,10,11,11a-hexahydro-4-oxo-4H-pyrido[3,2,1-jk]carbazole-5-carboxylic acid 1-(4-acetyl-1-piperazinyl)-7a,8,9,10,11,11a-hexahydro-4-oxo-4H-pyrido[3,2,1-jk]carbazole-5-carboxylic acid 1-(4-benzoyl-1-piperazinyl)-7a,8,9,10,11,11a-hexahydro-4-oxo-4H-pyrido[3,2,1-jk]carbazole-5-carboxylic acid 1-(4-methanesulfonyl-1-piperazinyl)-7a,8,9,10,11,11a-hexahydro-4-oxo-4H-pyrido[3,2,1-jk]carbazole-5-carboxylic acid 1-(4-benzyl-1-piperazinyl)-7a,8,9,10,11,11a-hexahydro-4-oxo-4H-pyrido[3,2,1-jk]carbazole-5-carboxylic acid 1-(4-methyl-1-piperazinyl)-7a,8,9,10,11,11a-hexahydro-4-oxo-4H-pyrido[3,2,1-jk]carbazole-5-carboxylic acid 1-[4-(4-hydroxy-1,5-naphthyridine-3-carbonyl)-1-piperazinyl]-7a,8,9,10,11,11a-hexahydro-4-oxo-4H-pyrido-[3,2,1-jk]carbazole-5-carboxylic acid 1-(4-ethyl-1-piperazinyl)-2-chloro-7a,8,9,10,11,11a-hexahydro-4-oxo-4H-pyrido[3,2,1-jk]carbazole-5-carboxylic acid 1-(4-acetyl-1-piperazinyl)-3-fluoro-7a,8,9,10,11,11a-hexahydro-4-oxo-4H-pyrido[3,2,1-jk]carbazole-5-carboxylic acid 8-(4-trifluoroacetyl-1-piperazinyl)-9-chloro-5-methyl-6,7-dihydro-1-oxo-1H,5H-benzo[ij]quinolizine-2-carboxylic acid 8-(4-trifluoroacetyl-1-piperazinyl)-9-fluoro-5-methyl-6,7-dihydro-1-oxo-1H,5H-benzo[ij]quinolizine-2-carboxylic acid 8-(4-trifluoroacetyl-1-piperazinyl)-10-chloro-5-methyl-6,7-dihydro-1-oxo-1H,5H-benzo[ij]quinolizine-2-carboxylic acid 8-(4-trichloroacetyl-1-piperazinyl)-9-chloro-5-methyl-6,7-dihydro-1-oxo-1H,5H-benzo[ij]quinolizine-2-carboxylic acid 8-(4-trifluoroacetyl-1-piperazinyl)-9-chloro-5-ethyl-6,7-dihydro-1-oxo-1H,5H-benzo[ij]quinolizine-2-carboxylic acid 8-(4-trifluoroacetyl-1-piperazinyl)-9-chloro-5-butyl-6,7-dihydro-1-oxo-1H,5H-benzo[ij]quinolizine-2-carboxylic acid 8-(4-monochloroacetyl-1-piperazinyl)-9-chloro-5-methyl-6,7-dihydro-1-oxo-1H,5H-benzo[ij]quinolizine-2-carboxylic acid 8-(4-trifluoromethanesulfonyl-1-piperazinyl)-9-chloro-5-methyl-6,7-dihydro-1-oxo-1H,5H-benzo[ij]quinolizine-2-carboxylic acid 8-(4-trifluoromethanesulfonyl-1-piperazinyl)-9-fluoro-5-methyl-6,7-dihydro-1-oxo-1H,5H-benzo[ij]quinolizine-2-carboxylic acid 8-[4-(2,2,2-trifluoroethanesulfonyl)-1-piperazinyl]-9-chloro-5-methyl-6,7-dihydro-1-oxo-1H,5H-benzo[ij]quinolizine-2-carboxylic acid 8-[4-(2-chloroethyl)-1-piperazinyl]-9-chloro-5-methyl-6,7-dihydro-1-oxo-1H,5H-benzo[ij]quinolizine-2-carboxylic acid 8-(4-tribromoacetyl-1-piperazinyl)-9-bromo-5-methyl-6,7-dihydro-1-oxo-1H,5H-benzo[ij]quinolizine-2-carboxylic acid 8-[4-(2-chlorobutyl)-1-piperazinyl]-9-chloro-5-methyl-6,7-dihydro-1-oxo-1H,5H-benzo[ij]quinolizine-2-carboxylic acid 8-(4-trifluoroacetyl-1-piperazinyl)-5-methyl-6,7-dihydro-1-oxo-1H,5H-benzo[ij]quinolizine-2-carboxylic acid 8-(4-trifluoroacetyl-1-piperazinyl)-9-chloro-6,7-dihydro-1-oxo-1H,5H-benzo[ij]quinolizine-2-carboxylic acid 8-(4-allyl-1-piperazinyl)-9-chloro-5-methyl-6,7-dihydro-1-oxo-1H,5H-benzo[ij]quinolizine-2-carboxylic acid 8-(4-crotyl-1-piperazinyl)-9-chloro-5-methyl-6,7-dihydro-1-oxo-1H,5H-benzo[ij]quinolizine-2-carboxylic acid 8-(4-allyl-1-piperazinyl)-5-methyl-6,7-dihydro-1-oxo-1H,5H-benzo[ij]quinolizine-2-carboxylic acid 8-(4-allyl-1-piperazinyl)-9-chloro-6,7-dihydro-1-oxo-1H,5H-benzo[ij]quinolizine-2-carboxylic acid 8-(4-allyl-1-piperazinyl)-9-fluoro-5-methyl-6,7-dihydro-1-oxo-1H,5H-benzo[ij]quinolizine-2-carboxylic acid 8-(4-trifluoromethyl-1-piperazinyl)-10-chloro-5-methyl-6,7-dihydro-1-oxo-1H,5H-benzo[ij]quinolizine-2-carboxylic acid 8-(4-trifluoromethyl-1-piperazinyl)-9-chloro-5-methyl-6,7-dihydro-1-oxo-1H,5H-benzo[ij]quinolizine-2-carboxylic acid 8-(4-trichloromethyl-1-piperazinyl)-9-chloro-5-methyl-6,7-dihydro-1-oxo-1H,5H-benzo[ij]quinolizine-2-carboxylic acid 8-[4-(2,2,2-trifluoroethyl)-1-piperazinyl]-9-chloro-5-methyl-6,7-dihydro-1-oxo-1H,5H-benzo[ij]quinolizine-2-carboxylic acid 8-[4-(4-chlorobutyl)-1-piperazinyl]-9-chloro-5-methyl-6,7-dihydro-1-oxo-1H,5H-benzo[ij]quinolizine-2-carboxylic acid 8-(4-trifluoromethyl-1-piperazinyl)-9-fluoro-5-methyl-6,7-dihydro-1-oxo-1H,5H-benzo[ij]quinolizine-2-carboxylic acid 8-(4-trifluoromethyl-1-piperazinyl)-5-methyl-6,7-dihydro-1-oxo-1H,5H-benzo[ij]quinolizine-2-carboxylic acid 8-[4-(2,2,2-trifluoroethyl)-1-piperazinyl]-9-chloro-6,7-dihydro-1-oxo-1H,5H-benzo[ij]quinolizine-2-carboxylic acid 8-(4-trifluoromethyl-1-piperazinyl)-9-chloro-5-ethyl-6,7-dihydro-1-oxo-1H,5H-benzo[ij]quinolizine-2-carboxylic acid 8-[4-(2-hydroxyethyl)-1-piperazinyl]-9-chloro-5-methyl-6,7-dihydro-1-oxo-1H,5H-benzo[ij]quinolizine-2-carboxylic acid 8-[4-(2-hydroxyethyl)-1-piperazinyl]-9-fluoro-5-methyl-6,7-dihydro-1-oxo-1H,5H-benzo[ij]quinolizine-2-carboxylic acid 8-[4-(2-hydroxyethyl)-1-piperazinyl]-10-chloro-5-methyl-6,7-dihydro-1-oxo-1H,5H-benzo[ij]quinolizine-2-carboxylic acid 8-[4-(2-hydroxyethyl)-1-piperazinyl]-5-methyl-6,7-dihydro-1-oxo-1H,5H-benzo[ij]quinolizine-2-carboxylic acid 8-[4-(2-hydroxyethyl)-1-piperazinyl]-9-chloro-6,7-dihydro-1-oxo-1H,5H-benzo[ij]quinolizine-2-carboxylic acid 8-[4-(2,3-dihydroxylpropyl)-1-piperazinyl]-9-chloro-5-methyl-6,7-dihydro-1-oxo-1H,5H-benzo[ij]quinolizine-2-carboxylic acid 8-[4-(4-hydroxybutyl)-1-piperazinyl]-9-chloro-5-methyl-6,7-dihydro-1-oxo-1H,5H-benzo[ij]quinolizine-2-carboxylic acid 8-[4-(2-propynyl)-1-piperazinyl]-9-chloro-5-methyl-6,7-dihydro-1-oxo-1H,5H-benzo[ij]quinolizine-2-carboxylic acid 8-[4-(2-propynyl)-1-piperazinyl]-9-fluoro-5-methyl-6,7-dihydro-1-oxo-1H,5H-benzo[ij]quinolizine-2-carboxylic acid 8-[4-(2-propynyl)-1-piperazinyl]-5-methyl-6,7-dihydro-1-oxo-1H,5H-benzo[ij]quinolizine-2-carboxylic acid 8-[4-(2-propynyl)-1-piperazinyl]-9-fluoro-6,7-dihydro-1-oxo-1H,5H-benzo[ij]quinolizine-2-carboxylic acid 8-[4-(1-methyl-2-propynyl)-1-piperazinyl]-9-chloro-5-methyl-6,7-dihydro-1-oxo-1H,5H-benzo[ij]quinolizine-2-carboxylic acid 8-[4-(2-propynyl)-1-piperazinyl]-10-chloro-5-methyl-6,7-dihydro-1-oxo-1H,5H-benzo[ij]quinolizine-2-carboxylic acid 8-[4-(4-methoxybenzyl)-1-piperazinyl]-9-chloro-5-methyl-6,7-dihydro-1-oxo-1H,5H-benzo[ij]quinolizine-2-carboxylic acid 8-[4-(4-methoxybenzyl)-1-piperazinyl]-9-fluoro-5-methyl-6,7-dihydro-1-oxo-1H,5H-benzo[ij]quinolizine-2-carboxylic acid 8-[4-(4-methoxybenzyl)-1-piperazinyl]-9-chloro-6,7-dihydro-1-oxo-1H,5H-benzo[ij]quinolizine-2-carboxylic acid 8-[4-(4-methoxybenzyl)-1-piperazinyl]-5-methyl-6,7-dihydro-1-oxo-1H,5H-benzo[ij]quinolizine-2-carboxylic acid 8-[4-(4-methoxybenzyl)-1-piperazinyl]-10-fluoro-5-methyl-6,7-dihydro-1-oxo-1H,5H-benzo[ij]quinolizine-2-carboxylic acid 8-[4-(3,4-dimethoxybenzyl)-1-piperazinyl]-9-chloro-5-methyl-6,7-dihydro-1-oxo-1H,5H-benzo[ij]quinolizine-2-carboxylic acid 8-[4-(β-3,4-dimethoxyphenethyl)-1-piperazinyl]-9-chloro-5-methyl-6,7-dihydro-1-oxo-1H,5H-benzo[ij]quinolizine-2-carboxylic acid 8-{4-[3-(4-ethoxyphenyl)propyl]-1-piperazinyl}-9-chloro-5-methyl-6,7-dihydro-1-oxo-1H,5H-benzo[ij]quinolizine-2-carboxylic acid 8-[4-(β-2,3,4-trimethoxyphenethyl)-1-piperazinyl]-9-chloro-5-methyl-6,7-dihydro-1-oxo-1H,5H-benzo[ij]quinolizine-2-carboxylic acid 8-(4-trifluoroacetyl-1-piperazinyl)-9-bromo-5-methyl-6,7-dihydro-1-oxo-1H,5H-benzo[ij]quinolizine-2-carboxylic acid 8-(4-trifluoromethyl-1-piperazinyl)-9-bromo-5-methyl-6,7-dihydro-1-oxo-1H,5H-benzo[ij]quinolizine-2-carboxylic acid 8-(4-allyl-1-piperazinyl)-9-bromo-5-methyl-6,7-dihydro-1-oxo-1H,5H-benzo[ij]quinolizine-2-carboxylic acid 8-(4-pentafluoropropionyl-1-piperazinyl)-5-methyl-6,7-dihydro-1-oxo-1H,5H-benzo[ij]quinolizine-2-carboxylic acid 8-(4-heptafluorobutyryl-1-piperazinyl)-9-chloro-6,7-dihydro-1-oxo-1H,5H-benzo[ij]quinolizine-2-carboxylic acid 8-(4-pentafluoropropionyl-1-piperazinyl)-10-chloro-5-methyl-6,7-dihydro-1-oxo-1H,5H-benzo[ij]quinolizine-2carboxylic acid 8-(4-heptafluorobutyryl-1-piperazinyl)-5-methyl-6,7-dihydro-1-oxo-1H,5H-benzo[ij]quinolizine-2-carboxylic acid 8-(4-trifluoromethanesulfonyl-1-piperazinyl)-9-chloro-6,7-dihydro-1-oxo-1H,5H-benzo[ij]quinolizine-2-carboxylic acid 8-(4-pentafluoropropionyl-1-piperazinyl)-9-chloro-6,7-dihydro-1-oxo-1H,5H-benzo[ij]quinolizine-2-carboxylic acid 8-(4-heptafluorobutyryl-1-piperazinyl)-10-chloro-5-methyl-6,7-dihydro-1oxo-1H,5H-benzo[ij]quinolizine-2-carboxylic acid 8-(4-trifluoromethanesulfonyl-1-piperazinyl)-5-methyl-6,7-dihydro-1-oxo-1H,5H-benzo[ij]quinolizine-2-carboxylic acid 8-(4-trifluoromethyl-1-piperazinyl)-6,7-dihydro-1-oxo-1H,5H-benzo[ij]quinolizine-2-carboxylic acid The compounds of this invention represented by the formula (I) can be prepared by various alternative procedures. For example, one procedure comprises reacting a benzoheterocyclic compound of the formula (II)

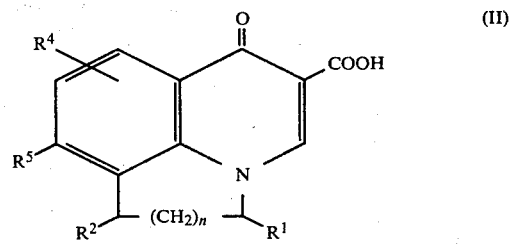

wherein $R^1$, $R^2$, $R^4$ and n have the same meaning as defined above, and $R^5$ represents a halogen group, a lower alkanesulfonyloxy group or an arylsulfonyloxy group; with a piperazine compound represented by the formula (III)

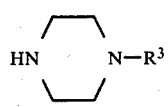

wherein $R^3$ has the same meaning as defined above.

The term "lower alkanesulfonyloxy" as used herein refers to a straight or branched alkanesulfonyloxy group having from 1 to 4 carbon atoms, such as a methanesulfonyloxy group, an ethanesulfonyloxy group, a propanesulfonyloxy group, an isopropanesulfonyloxy group, a butanesulfonyloxy group, a tert-butanesulfonyloxy group and the like.

The term "arylsulfonyloxy" as used herein includes a benzenesulfonyloxy group, a naphthalenesulfonyloxy group and the like. The aryl ring included in the arenesulfonyloxy group may be substituted with one or more of a halogen group, a lower alkyl group, a hydroxy group, a nitro group and the like.

More particularly, the reaction of the compound of the formula (II) with the compound of the formula (III) can be carried out in an inert solvent, desirably under pressurized conditions, i.e., at a pressure of from about 1 to 20 atms (atmospheres), and preferably from 1 to 10 atms, at a temperature of from about 100° to 250° C., and preferably from 140° to 200° C., for a period of about 5 to about 20 hours.

In the above reaction the proportion of the compound of the formula (III) to the compound of the formula (II) is not particularly limited, and can be varied broadly. Usually the reaction is carried out using at least an equimolar amount, and preferably from 1 to 5 mols, of the compound of the formula (III) per mol of the compound of the formula (II).

Suitable examples of the inert solvent include water, lower alcohols such as methanol, ethanol, isopropanol, etc., aromatic hydrocarbons such as benzene, toluene, xylene, etc., ethers such as tetrahydrofuran, dioxane, diglyme (diethylene glycol dimethyl ether), etc., dimethyl sulfoxide, dimethylformamide, hexamethylphosphoric triamide and the like, with dimethyl sulfoxide, dimethylformamide and hexamethylphosphoric triamide being preferred.

The above reaction may be conducted in the presence of a deoxidizing agent in an amount of at least an approximately equimolar amount, and preferably from 1 to 2 mols, of the oxidizing agent per mol of the compound of the formula (II).

Examples of suitable deoxidizing agent include alkali metal hydroxides such as sodium hyroxide, potassium hydroxide, etc., inorganic carbonates such as sodium carbonate, potassium carbonate, potassium hydrogen carbonate, sodium hydrogen carbonate, etc., tertiary amines such as pyridine, quinoline, triethylamine, etc.

With respect to the benzoheterocyclic compounds of the formula (II) which can be used as the starting material for preparing the compounds of this invention represented by the formula (I), some of them are known compounds, as described in U.S. Pat. Nos. 3,917,609, 3,896,131, 3,985,882, 3,969,463, 4,001,243 and 4,014,877, and others are novel and can be prepared by Reaction Scheme-1 described hereinbelow.

On the other hand, the compounds of the formula (III), another starting material of the compounds of this invention represented by the formula (I), are known and commercially available.

Reaction Scheme-1

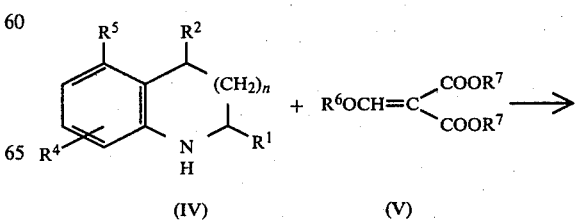

-continued
Reaction Scheme-1

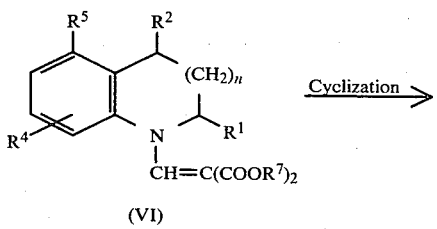

etc., or can be easily prepared by known processes described therein; while those in which $R^5$ represents a lower alkanesulfonyloxy group or an arylsulfonyloxy group are novel compounds and can be prepared easily in accordance with the process shown in Reaction Scheme-2 shown hereinbelow.

On the other hand, the compounds of the formula (V), another starting material, are known compounds and commercially available.

Further, the compounds of the formula (IV) in which $R^5$ represents a halogen atom can also be prepared easily in accordance with the process shown in Reaction Scheme-2 below.

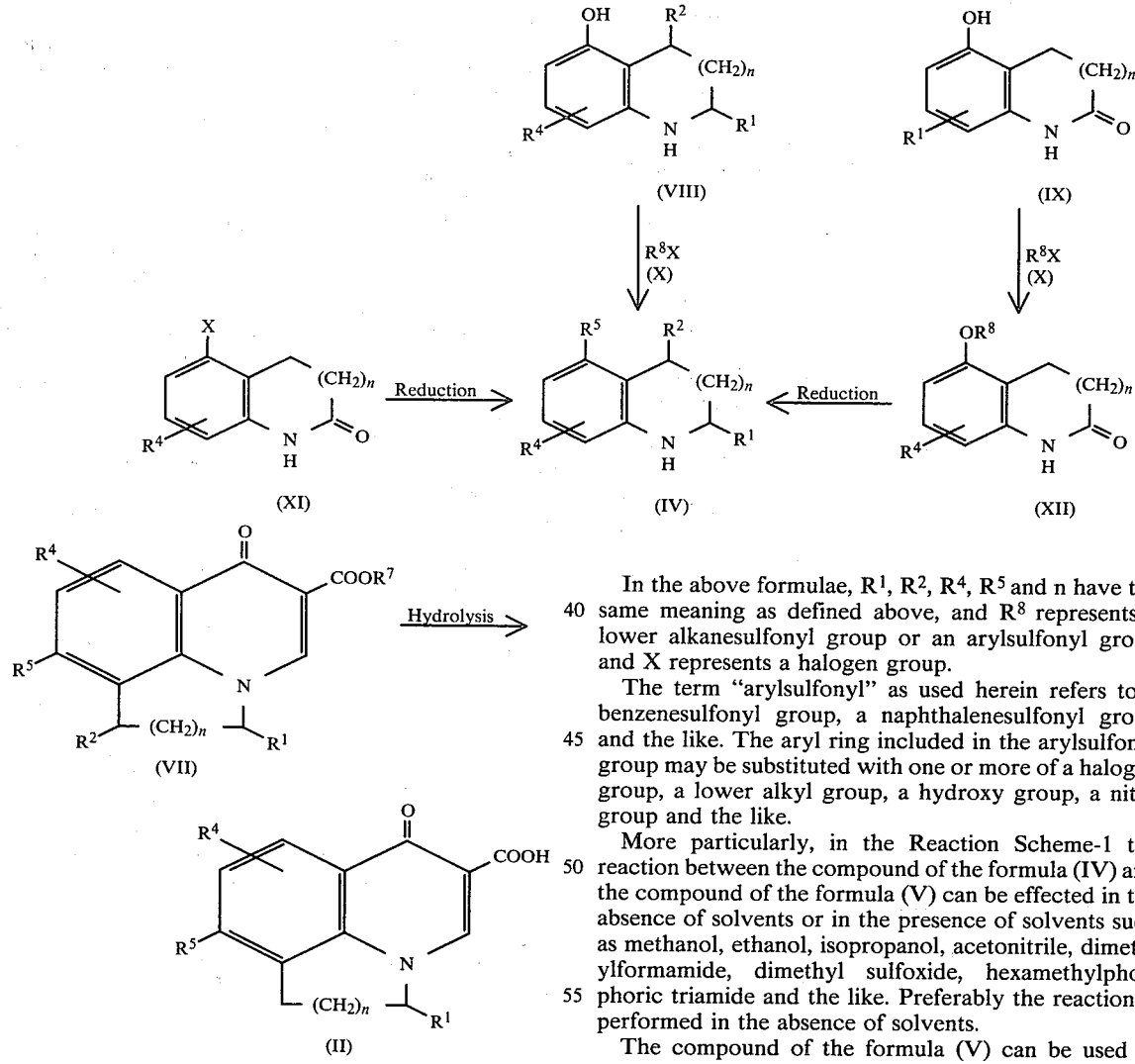

In the above formulae (II), (IV), (V), (VI) and (VII), $R^1$, $R^2$, $R^4$, $R^5$ and n have the same meaning as defined above, and $R^6$ and $R^7$, which may be the same or different, each represent a lower alkyl group.

In Reaction Scheme-1 above, of the compounds of the formula (IV) which are used as a starting material those in which $R^5$ represents a halogen atom are known compounds as described in the above-mentioned U.S. Patents to Gerster et al., Bayer, *Annalen*, 278, 105 (1894), Schmidt and Sitwart, *Berichte*, 45, 1779 (1912), In the above formulae, $R^1$, $R^2$, $R^4$, $R^5$ and n have the same meaning as defined above, and $R^8$ represents a lower alkanesulfonyl group or an arylsulfonyl group and X represents a halogen group.

The term "arylsulfonyl" as used herein refers to a benzenesulfonyl group, a naphthalenesulfonyl group and the like. The aryl ring included in the arylsulfonyl group may be substituted with one or more of a halogen group, a lower alkyl group, a hydroxy group, a nitro group and the like.

More particularly, in the Reaction Scheme-1 the reaction between the compound of the formula (IV) and the compound of the formula (V) can be effected in the absence of solvents or in the presence of solvents such as methanol, ethanol, isopropanol, acetonitrile, dimethylformamide, dimethyl sulfoxide, hexamethylphosphoric triamide and the like. Preferably the reaction is performed in the absence of solvents.

The compound of the formula (V) can be used in excess amounts over the equimolar amount relative to the compounds of the formula (IV), preferably in an equimolar amount in the absence of solvents and in an amount of from about 1.1 to 1.5 mols per mol of the compound of the formula (III) in the presence of solvents. The reaction can generally be carried out at a temperature from room temperature (about 15° to 30° C.) to about 150° C., and preferably from 100° to 130° C., for a period of from about 0.5 to 6 hours, thereby easily yielding the compound represented by the formula (VI).

The subsequent cyclization reaction of the thus-obtained compound of the formula (VI) can be effected in accordance with conventional cyclization reactions, for example, by heating the compound of the formula (VI) or by using an acidic substance such as phosphorus oxychloride, phosphorus pentachloride, phosphorus trichloride, thionyl chloride, concentrated sulfuric acid, polyphosphoric acid and the like. When the cyclization is effected by heating, it is preferred to heat the compound of the formula (VI) in a solvent such as high boiling point hydrocarbons or high boiling point ethers, for example, tetralin diphenyl ether, diethylene glycol dimethyl ether, etc., at a temperature of from about 100° to 250° C., and preferably from 150° to 200° C., for a period of from about 0.5 to 6 hours. When the cyclization is effected using an acidic substance, the cyclization can be effected in the presence of the acid substance in an approximately equimolar amount to a large excess amount, preferably 10 to 20 molar excess acid, relative to the amount of the compound of the formula (VI) at a temperature of about 100° to 150° C. for a period of about 0.5 to about 6 hours, whereby the desired compounds of the formula (VII) can be produced advantageously.

In the above Reaction Scheme-1, the hydrolysis of the compound of the formula (VII) into the compound of the formula (II) can be achieved by a conventional hydrolysis procedure in the presence of a typical hydrolysis usual catalyst, for example, a basic compound such as sodium hydroxide, potassium hydroxide, barium hydroxide and the like, or an inorganic or organic acid such as sulfuric acid, hyrochloric acid, nitric acid, acetic acid, an aromatic sulfonic acid and the like. The hydrolysis can be carried out in a solvent such as water, methanol, ethanol, isopropanol, acetone, methyl ethyl ketone, dioxane, ethylene glycol, acetic acid and the like at a temperature of from room temperature to about 200° C., and preferably from 50° to 150° C., for a period of from about 0.5 to 6 hours, thereby easily yielding the compound represented by the formula (II).

In Reaction Scheme-2 above, a suitable amount of the compound of the formula (X) to be reacted with the compound of the formula (VIII) or (IX) is at least an approximately equimolar amount, and preferably from 1 to 2 mols of the compound of the formula (X), per mol of the compound of the formula (VIII) or (IX).

The reaction proceeds usually in an inert solvent in the presence of a deoxidizing agent in an amount of at least an approximately equimolar amount, and preferably from 1 to 2 mols, of the oxidizing agent per mol of the compound of the formula (VIII) or (IX), at a temperature of from about 0° to 100° C., and preferably at room temperature, for from about 0.5 to 6 hours, thereby yielding the compound of the formula (IV) or (XII).

Examples of suitable deoxidizing agents include alkali metal hydroxides such as sodium hydroxide, potassium hydroxide, etc., inorganic carbonates such as sodium carbonate, potassium carbonate, potassium hydrogen carbonate, sodium hydrogen carbonate, etc., tertiary amines such as pyridine, quinoline, triethylamine, etc.

Examples of suitable inert solvents include lower alcohols such as methanol, ethanol, isopropanol, etc., ethers such as dioxane, tetrahydrofuran, diglyme, etc., aromatic hydrocarbons such as benzene, toluene, etc., dimethyl sulfoxide, dimethylformamide, hexamethylphosphoric triamide, pyridine, etc.

In Reaction Scheme-2 above, the reduction of the compounds of the formula (XI) or (XII) can be conducted catalytically or using a conventional hydrogenating agent such as a combination of sodium borohydride or lithium aluminum hydride and a lower fatty acid, e.g., acetic acid, trifluoroacetic acid, -propionic acid, etc.

Suitable amounts of sodium borohydride or lithium aluminum hydride and the lower fatty acid are an approximately equimolar amount to a large excess amount, and preferably from 3 to 5 mols per mol of the compound of the formula (XI) or (XII), respectively.

The reduction reaction using a hydrogenating agent can proceed advantageously in an inert solvent such as ethers, e.g., dioxane, tetrahydrofuran, diglyme, etc., aromatic hydrocarbons, e.g., benzene, toluene, etc., lower fatty acids, e.g., trifluoroacetic acid, propionic acid, etc., at a temperature of from room temperature to about 100° C., and preferably from 50° to 100° C., for from about 1 to 6 hours.

The compounds of this invention represented by the formula (I) can also be prepared by the following Reaction Scheme-2a.

Reaction Scheme-2a

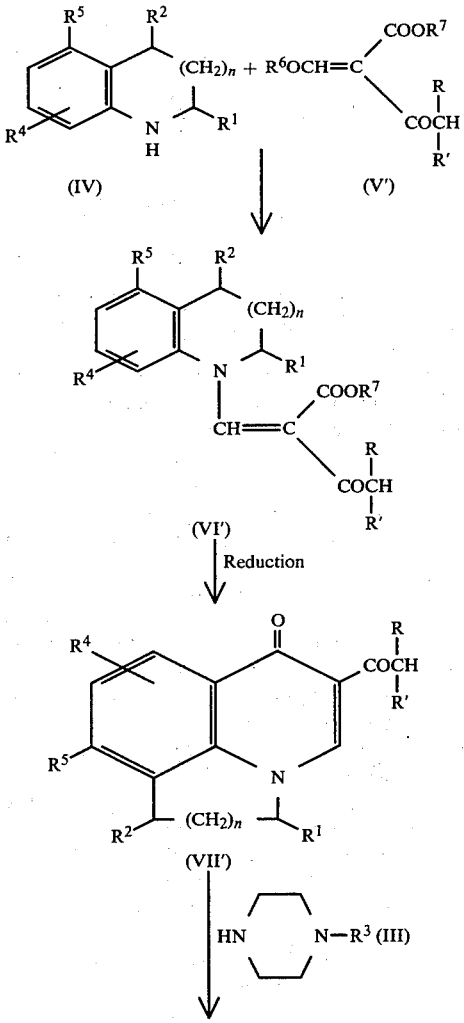

-continued
Reaction Scheme-2a

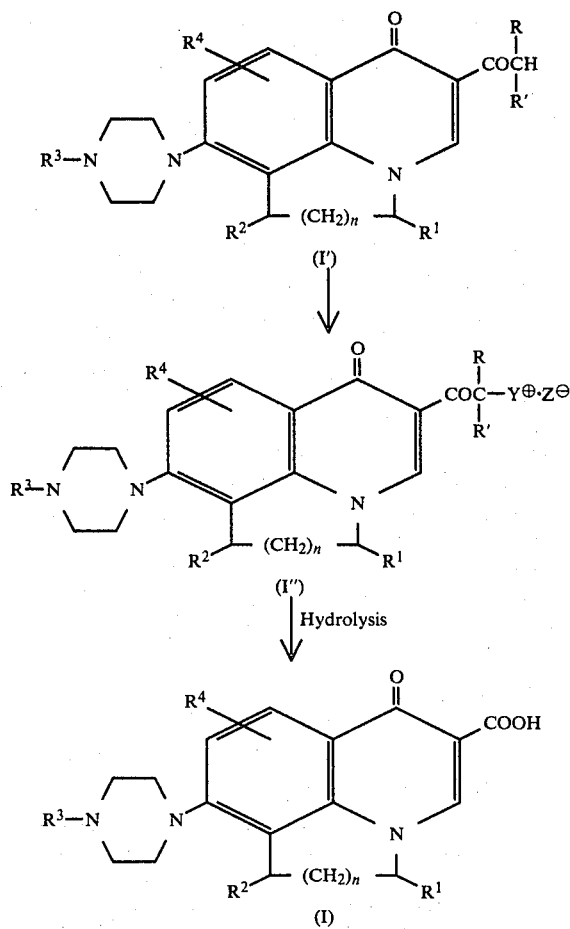

wherein R and R' represent a hydrogen atom or a lower alkyl group; $Y^{\oplus}$ represents an aromatic heterocyclic ring containing a tertiary nitrogen atom through which it is connected or a trialkylamino group; $Z^{\ominus}$ represents an anionic ion; and $R^1$, $R^2$, $R^3$, $R^4$, $R^5$, $R^6$, $R^7$ and n have the same meaning as defined above.

In the above Reaction Scheme-2a, the reaction between the compound of the formula (IV) and the compound of the formula (V') can be conducted in the same manner as the reaction between the compound of the formula (IV) and the compound of the formula (V) described above. The cyclization of the compound of the formula (VI') can be carried out in the same manner as the cyclization of the compound of the formula (VI) described above. The reaction between the compound of the formula (VII') and the compound of the formula (III) can be carried out in the same manner as the reaction between the compound of the formula (II) and the compound of the formula (III).

The preparation of the compounds of the formula (I) from the compound of the formula (I') can be effected by reacting the compound of the formula (I') with a tertiary-nitrogen-atom-containing aromatic heterocyclic compound or a trialkylamine and an anion donating compound in an appropriate inert solvent to obtain a compound of the formula (I'') and hydrolyzing the compound of the formula (I'') thus obtained after isolation or without isolation thereof.

In the above reaction, examples of suitable tertiary-nitrogen-atom-containing aromatic heterocyclic compound include unsubstituted pyridine and alkyl substituted pyridine compounds such as picolines, lutidines, etc., quinoline and alkyl substituted quinolines such as quinaldine, lepidine, etc.

Examples of suitable trialkylamines include trialkylamines having 1 to 6 carbon atoms in each alkyl moiety, such as trimethylamine, triethylamine, tripropylamine, triisopropylamine, etc.

Examples of suitable anion donating compounds include those compounds which can donate a halogen ion such as an iodine ion, a bromine ion, a chlorine ion, etc., for example, iodine, bromine, chlorine, or those compounds which can donate a sulfate residue, a phosphate residue, a perchlorate residue, etc., for example, sulfuric acid, phosphoric acid, perchloric acid, etc.

Examples of suitable inert solvent which can be used in the above reaction include lower alcohols such as methanol, ethanol, isopropanol, etc., aromatic hydrocarbons such as benzene, toluene, etc., ethers such as tetrahydrofuran, dioxane, diglyme, etc., dimethyl sulfoxide, dimethylformamide, hexamethylphosphoric triamide, pyridine, etc.

The tertiary-nitrogen-containing aromatic heterocyclic compound or trialkylamine, and anion donating compound can be used in excess amounts over the equimolar amount relative to the compounds of the formula (I'), and preferably are used in an amount of from 1 to 2 mols per mol of the compound of the formula (I').

The reaction can usually be carried out at from room temperature to about 120° C., and is preferably from 50° to 100° C., for from about 30 minutes to 6 hours.

The hydrolysis of the compound of the formula (I'') thus-obtained can be conducted in an appropriate solvent in the absence or presence of an acid hydrolyzing agent or an alkaline hydrolyzing agent, preferably in the presence of such agent.

Examples of suitable alkaline hydrolyzing agent which can be used in the above hydrolysis reaction include alkali metal hydroxides such as sodium hydroxide, potassium hydroxide, etc., alkaline earth metal hydroxides such as calcium hydroxide, etc., ammonium hydroxide, and carbonates of these metals and ammonium.

The hydrolysis of the compound of the formula (I'') can also be conducted in an aqueous medium in the presence of a trialkylamine, such as a lower trialkylamine, e.g., trimethylamine, triethylamine, etc.

Examples of suitable solvents which can be used include lower alcohols such as methanol, ethanol, isopropanol, etc., aromatic hydrocarbons such as benzene, toluene, etc., ethers such as tetrahydrofuran, dioxane, diglyme, etc., water, pyridine, dimethyl sulfoxide, dimethylformamide, hexamethylphosphoric triamide, etc.

The hydrolysis can usually be effected at from about 20° C. to 150° C., and preferably at from 80° C. to 120° C., for from 30 minutes to 6 hours. The above hydrolysis can be accelerated by the addition of a lower alcohol.

Of the compounds of this invention represented by the formula (I) those compounds in which $R^3$ represents a lower alkyl group, a lower alkanoyl group, a benzoyl group, a lower alkanesulfonyl group, a p-toluenesulfonyl group, a phenylalkyl group, or a group represented by the following formula

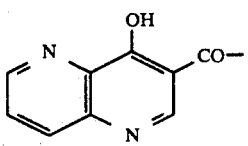

that is, compounds of the formula (Ib) below, can also be prepared by reacting compounds in which $R^3$ represents a hydrogen atom (compounds of the formula (Ia) below) with a compound of the formula (XIII) below in the presence of a deoxidizing agent.

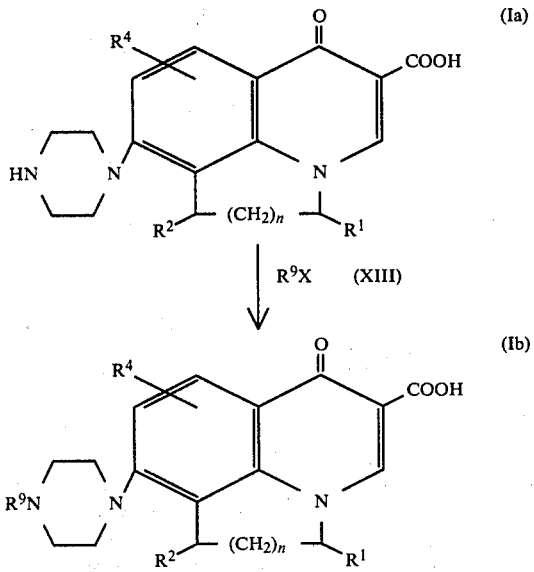

In the above formulae, $R^1$, $R^2$, $R^4$, n and X have the same meaning as defined above, and $R^9$ represents a lower alkyl group, a lower alkanoyl group, a benzoyl group, a lower alkanesulfonyl group, a p-toluenesulfonyl group, a phenylalkyl group or a group represented by the following formula

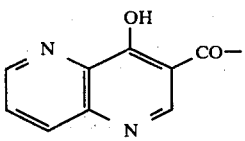

The compounds of this invention represented by the formula (I) prepared as described above can form pharmaceutically acceptable salts with acids when the compound of the formula (I) has a basic group, and this invention also includes within its scope such pharmaceutically acceptable salts. The pharmaceutically acceptable acids which can be used for the salt formation can be various organic or inorganic acids, for example, hydrochloric acid, sulfuric acid, nitric acid, hydrobromic acid, phosphoric acid, acetic acid, oxalic acid malonic acid, succinic acid, maleic acid, fumaric acid, malic acid, mandelic acid, ethanesulfonic acid, p-toluenesulfonic acid and the like.

The benzoheterocyclic compounds of the formula (I) can be converted into a corresponding carboxylate by reacting the carboxylic acid with a pharmaceutically acceptable basic compound. Examples of basic compounds are inorganic basic compounds such as sodium hydroxide, potassium hydroxide, calcium hydroxide, aluminum hydroxide, sodium bicarbonate and the like and organic basic compounds such as morpholine, piperazine, pyridine, piperidine, ethylamine, dimethylamine, triethylamine, aniline and the like.

The compounds of the formula (I) and the salts thereof obtained as described above can be isolated from the respective reaction mixtures upon completion and purified by conventional procedures, for example, by solvent extraction, dilution, precipitation, recrystallization, column chromatography and the like.

The compounds of this invention of the formula (I) and the salts thereof exhibit excellent antimicrobial activity broadly, on both gram positive and negative bacteria at low concentrations. They are useful compounds which show particularly potent antibacterial activity on Streptococcus, Pseudomonas, Enterobacter, etc., on which many conventional synthetic antibacterial agents are not effective or only slightly effective. In addition, they show a high antibacterial activity on coliform bacilli, staphylococci, etc., which are major causes of infectious diseases and are also effective on Serratia, Klebsiella, etc., which cause infectious diseases that have recently attracted wide attention of many workers in the field, and therefore they are very useful clinically.

As stated above, the compounds of this invention are advantageous not only because they are characterized by a broad antimicrobial spectrum and potent activity, but also because they show no decrease in antimicrobial activity but rather show a tendency of an increase in such activity even in the presence of a serum. This phenomenon is surprising to those skilled in the art, since it has hitherto been observed that conventional pharmaceuticals having antimicrobial activity show decreased activity in the presence of a serum. This indicates that the compound of this invention can exhibit potent antimicrobial activity in the blood.

The oral toxicity of the compounds of this invention is low as compared with effective oral dosage thereof.

The compounds of this invention have excellent antimicrobial activity on those bacteria which are resistant or have acquired resistance to conventional antibiotics such as penicillin, cephalosporin, ampicillin, streptomycin, erythromycin, Kanamycin, nalidixic acid, etc.

The compounds of this invention represented by the formula (I) can be converted into penicillanic acid derivatives represented by the formula (XIV) below which exhibit excellent antimicrobial activity on gram positive and negative bacteria, especially on Pseudomonas and Streptococcus, in accordance with the process shown in Reaction Scheme-3 below and as exemplified in Reference Examples 16 to 18.

Reaction Scheme-3

Reaction Scheme-3

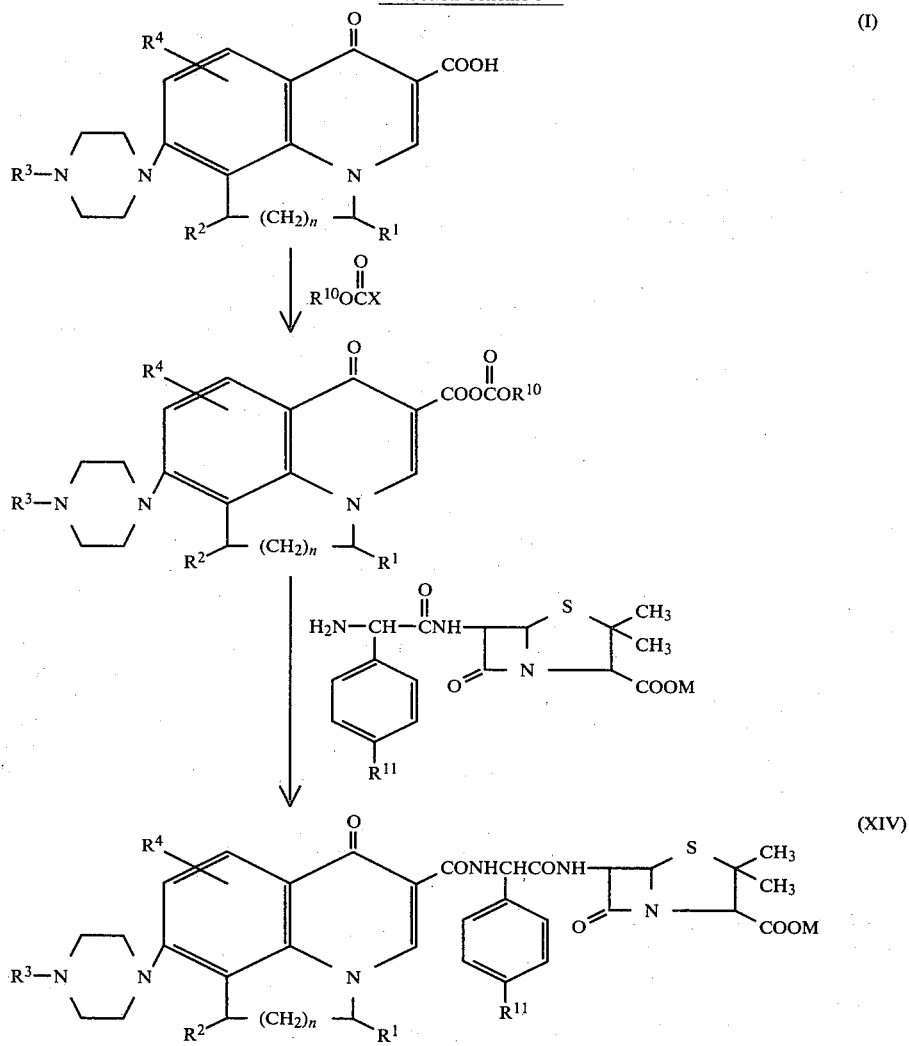

In Reaction Scheme-3 above, the reaction between the compound of the formula (I) and the alkyl haloformate $R^{10}OOCX$, which is a known compound, can be achieved in accordance with conventional Schotten-Baumann reaction and the resulting compound (a carboxyl-activated derivative of the compound of the formula (I)) can be subjected further to reaction with an ampicillin derivative or cephaloglycine derivative without isolation. The ampicillin derivatives and cephaloglycine derivatives are described in F. P. Doyle et al., *J. Chem. Soc.*, 1440 (1962) and J. L. Spencer et al., *J. Med. Chem.*, 9, 746 (1966).

The Schotten-Baumann reaction applied to the reaction between the compounds of the formula (I) and the alkyl haloformate can be effected without solvent in the presence of a basic compound. The reaction proceeds advantageously in a solvent in the presence of a basic compound.

Examples of suitable solvents include chloroform, dichloromethane, dichloroethane, acetonitrile, dimethylformamide, dimethyl sulfoxide, hexamethylphosphoric triamide, etc.

Examples of suitable basic compounds include amines such as triethylamine, trimethylamine, pyridine, dimethylaniline, N-methylmorpholine, etc., metal salts of inorganic acid such as potassium carbonate, sodium carbonate, potassium hydrogen carbonate, sodium hydrogen carbonate, etc., metal salts of organic acids such as sodium acetate, sodium propionate, etc.

Examples of suitable alkyl haloformate include methyl chloroformate, methyl bromoformate, ethyl chloroformate, ethyl bromoformate, isobutyl chloroformate, etc.

The proportion of the compound of the alkyl haloformate to the compound of the formula (I) is generally at least an equimolar amount, and preferably 1.1 to 1.5 mols when the reaction proceeds in a solvent, of the alkyl formate per mol of the compound of the formula (I).

The reaction can be carried out at a temperature of about $-20°$ C. to about $30°$ C., preferably 0 to room temperature, for about 0.5 to about 3 hours.

The reaction of the carboxyl-activated derivative of the compound of the formula (I) with the ampicillin derivative or cephaloglycine derivative can proceed advantageously in the above-described solvent or a mixture of water and the solvent using at least an approximately equimolar, preferably 1 to 1.5 mols, of the ampicillin derivative or cephaloglycine derivative per mol of the compound (I) at a temperature of room temperature to about 100° C., preferably at room temperature for about 2 to about 10 hours.

In the above formulae, $R^{10}$ represents a lower alkyl group, X represents a halogen group, $R^{11}$ represents a hydrogen atom and a hydroxy group, M represents a hydrogen atom or an alkali metal and $R^1$, $R^2$, $R^3$, $R^4$ and n have the same meaning as defined above.

With respect to the compounds of formula (II) which can be used as the starting material for preparing the compounds of this invention represented by the formula (I), some of those in which $R^4$ represents a halogen atom are known compounds as described in U.S. Pat. Nos. 3,917,609, 3,896,131, 3,985,882, 3,969,463, 4,001,243 and 4,014,877 and others can be easily prepared by appropriate selection of starting materials according to known processes as described in Japanese Patent Publication No. 6156/76 and U.S. Pat. No. 4,014,877.

The compounds of the formula (IIb)

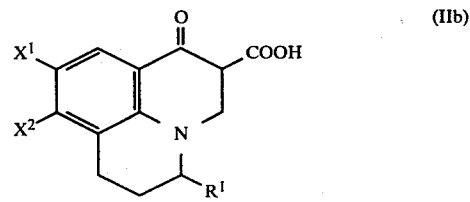

wherein $X^1$ and $X^2$ each represents a halogen group and $R^1$ has the same meaning as above, can also be prepared by the following Reaction Scheme-4.

Reaction Scheme-4

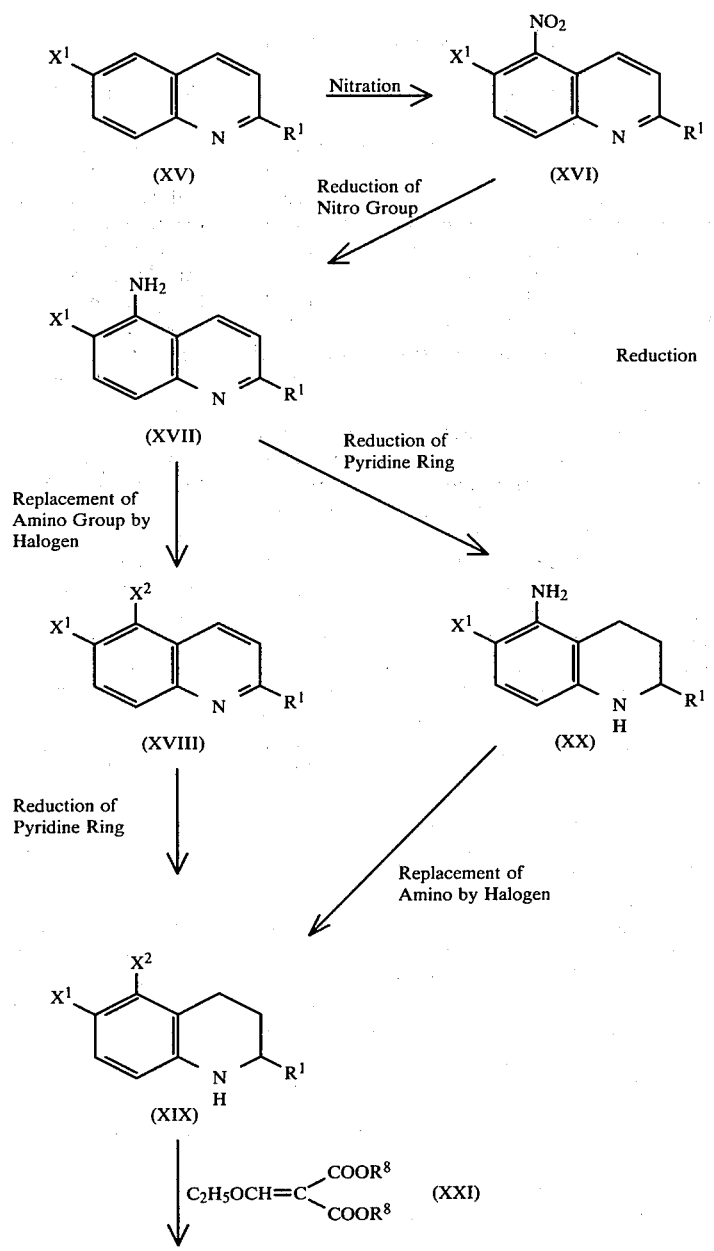

Reaction Scheme-4 -continued

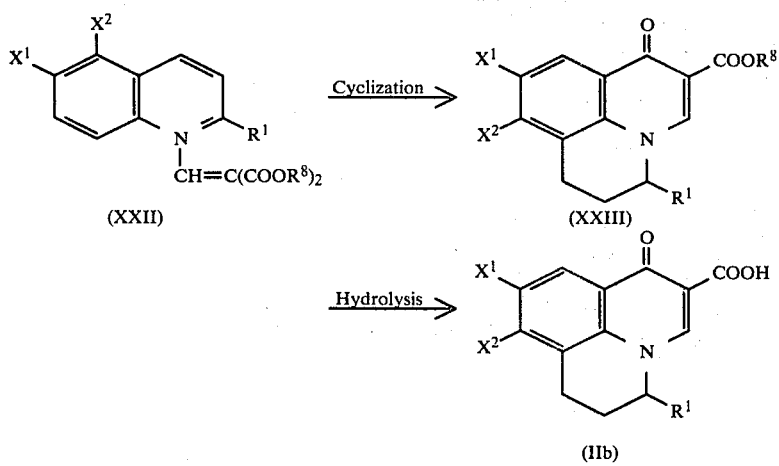

In the above formulae, $R^1$, $R^8$, $X^1$ and $X^2$ have the same meanings as defined above.

In the Reaction Scheme-4 above, nitration of the compound of the formula (XV) can proceed under conventional conditions for nitration of aromatic compounds, e.g., in the absence of solvents or in the presence of a suitable inert solvent using a nitration agent.

Suitable examples of the inert solvent include acetic acid, acetic anhydride, concentrated sulfuric acid, etc.

Suitable examples of nitration agent include fuming nitric acid, concentrated nitric acid, a mixed acid (a mixture of nitric acid and sulfuric acid, fuming sulfuric acid, phosphoric acid or acetic anhydride), alkali metal nitrates such as potassium nitrate and sodium nitrate, and sulfuric acid, etc.

The reaction proceeds advantageously in the presence of at least an equimolar amount, and preferably an excess amount, of the nitration agent, with respect to the starting compound, at a temperature of, preferably, from 0° to 15° C. for from 1 to 4 hours.

Reduction of the nitro group of the compound of the formula (XVI) obtained in the above nitration can be conducted in an inert solvent in the presence of a reducing agent such as a mixture of iron, zinc, tin or stannous chloride and an acid (e.g., hydrochloric acid and sulfuric acid) or a mixture of iron, iron sulfite, zinc or tin and hydroxide, sulfate, sulfite, etc., of an alkali metal. Alternatively, the reduction can be carried out catalytically using a reducing catalyst such as palladium on carbon in an inert solvent.

Examples of suitable inert solvents include water, acetic acid, methanol, ethanol, dioxane, etc.

The conditions under which the above reduction of nitro group is carried out can be suitably selected. For example, the reduction using a mixture of stannous chloride and hydrochloric acid as a reducing agent can proceed advantageously at a temperature of from 70° to 100° C. for from 0.5 to 1 hour using at least equimolar amount, and preferably from 1 to 2 mols of the reducing agent per mol of the starting compound. When the reduction is carried out catalytically, it can proceed advantageously at room temperature for from 0.5 to several hours.

The amino group of the compound of the formula (XVII) thus-obtained can be replaced by halogen by the application of the Sandmeyer reaction involving diazotation. Diazotation of the compound of the formula (XVII) can proceed advantageously in a solvent such as water, hydrochloric acid, sulfuric acid, etc., in the presence of a diazotation agent such as a mixture of sodium sulfite or potassium nitrite and hydrochloric acid or sulfuric acid at a temperature of from −30° C. to room temperature for from 0.5 to 2 hours. Subsequently, the diazonium salt of the compound of the formula (XVIII) thus-obtained, without isolation, can be reacted, with a halogenating agent such as cuprous chloride, cuprous bromide, etc., in an amount of at least an equimolar amount, and preferably from 1 to 2 mols, of the halogenating agent per mol of the starting compound at a temperature of from 0° C. to 50° C., for from 0.5 to 2 hours, to form a compound of the formula (XVIII).

Reduction of the pyridine ring of the compound of the formula (XVIII) can be carried out catalytically in an inert solvent such as dioxane, tetrahydrofuran, acetic acid, water, etc., under acidic condition using various acids capable of forming a quinolinium salt such as acetic acid, hydrochloric acid, sulfuric acid, etc., in the presence of a catalytic reduction agent such as platinum-carbon, palladium-carbon, rhodium-carbon, ruthenium-carbon, etc., at a temperature of from room temperature up to 50° C. for from 1 to 10 hours, thus yielding a compound of the formula (XIX).

Alternatively, the compound of the formula (XIX) can also be prepared by reducing the pyridine ring of the compound of the formula (XVII) to form a compound of the formula (XX) and then replacing the amino group of the compound of the formula (XX) by halogen atoms. The reduction of the pyridine ring of the compound of the formula (XVII) can be carried out in the same manner as the reduction of the pyridine ring of the compound of the formula (XVIII). Also, the replacement of the amino group of the compound of the formula (XX) by a halogen atom can be conducted in the same manner as the replacement of the amino group of the compound of the formula (XVII) by a halogen atom.

Further, the compound of the formula (XX) can be prepared by reducing the compound of the formula (XVI) in the same manner as the reduction of the pyridine ring of the compound of the formula (XVII).

Reaction between the compound of the formula (XIX) thus-obtained and the compound of the formula (XXI) can be carried out under the same conditions as the reaction between the compound of the formula (IV) and that of the formula (V).

Cyclization of the compound (XXII) which is formed in the above reaction and hydrolysis of the cyclized compound of the formula (XXIII) can proceed in an analogous manner as the cyclization of the compound of the formula (VI) and the hydrolysis of the compound of the formula (VII), respectively, thus yielding the compound of the formula (IIb).

Having asymmetric carbon atoms, the compounds of the formula (I) can exist in optically active forms and this invention includes such optical isomers within its scope.

In using the compounds of this invention of the formula (I) and the salts thereof as therapeutic agents, these compounds can be formulated into pharmaceutical compositions together with ordinary pharmaceutically acceptable carriers. Suitable carriers which can be used are, for example, diluents or excipients, such as fillers, extenders, binders, wetting agents, disintegrants, surface active agents and lubricants which are usually employed to prepared such drugs depending on the type of dosage forms.

Various dosage forms of the therapeutic agents as an antimicrobial agent can be selected according to the purpose of the therapy. Typical dosage forms which can be used are: tablets, pills, powders, liquid preparations, suspensions, emulsions, granules, capsules, suppositories, and injectable preparations (solutions, suspensions, etc.).

In molding a pharmaceutical composition containing the compounds of the formula (I) or the pharmaceutically acceptable salt thereof as an active ingredient into a tablet form, a wide range of carriers known in the art can be used. Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween (fatty acid ester of polyoxyethylenesorbitan, produced by Atlas Powder Co.), sodium lauryl sulfate, stearic acid monoglyceride, starch, and lactose, disintegration inhibitors such as white sugar, stearic acid glyceryl ester, cacao butter and hydrogenated oils, absorption promotors such as quaternary ammonium bases and sodium lauryl sulfate, humectants such as glycerol and starch, adsorbents such as starch, lactose, kaolin, bentonite and colloidal silicic acid, and lubricants such as purified talc, stearic acid salts, boric acid powder, Macrogol (trade name for a polyethylene glycol, produced by Shinetsu Chemical Industry Co., Ltd.) and solid polyethylene glycol.

The tablets, if desired, can be coated, and made into gugar-coated tablets, gelatin-coated tablets, enteric-coated tablets, film-coated tablets, or tablets comprising two or more layers.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, esters of higher alcohols, gelatin, and semisynthetic glycerides.

When the pharmaceutical composition is formulated into an injectable preparation, the resulting solution and suspension are preferably sterilized and isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a therapeutic agent, e.g., as a nephritis treating agent in an amount sufficient to prepare isotonic solutions. The antimicrobial pharmaceutical composition may further contain ordinary dissolving acids, buffers, pain-alleviating agents, and preservatives, and optionally coloring agents, perfumes, flavors, sweeteners, and other drugs.

The amount of the compound of the formula (I) and the pharmaceutically acceptable salts thereof of this invention as an active ingredients to be incorporated into a pharmaceutical composition useful as an antimicrobial agent is not particularly limited, and can vary over a wide range. A suitable effective amount of the compound of the formula (I) and the pharmaceutically acceptable salts thereof of this invention is usually from about 1% to 70% by weight, and preferably from 5 to 50% by weight, based on the weight of the entire composition.

There is no particular restriction on the manner of using the therapeutic agent and the therapeutic agent can be administered by routes suitable for the particular forms of the therapeutic agent. For example, the tablets, pills, liquid preparations, suspensions, emulsions, granules, and capsules are orally administered. The injectable preparations are intravenously administered either alone or together with ordinary auxiliary agents such as glucose and amino acids. Furthermore, as required, the therapeutic agent can be singly administered intramuscularly, intracutaneously, subcutaneously, or intraperitoneally. The suppository is administered intrarectally and the ointment is coated on the skin.

The dosage of the antimicrobial agent is suitably selected according to the purpose of use, the symptoms, etc. Usually, a preferred dosage of the compound of this invention is about 10 mg to 5 g/kg body wt/day in 3 or 4 doses/day.

I. ANTIMICROBIAL ACTIVITY

1. TEST METHOD

The antimicrobial activity of the following test compounds on various test organisms listed below was determined by the serial dilution method on agar plate (Heart Infusion agar produced by Difco Co.) (see CHEMOTHERAPY 22, pp. 1126–1128 (1974)), and the minimum inhibitory concentrations (mcg/ml) obtained are shown in Table 1 below.

A sample of each test organism was prepared so that the population of the organism was $1 \times 10^8$ cells/ml (O.D. 660 m$\mu$=0.07 to 0.16) and $1 \times 10^6$ cells/ml (which was obtained by diluting the above 1×10⁸ cells/ml preparation).

2. TEST ORGANISMS

| | | |
|---|---|---|
| 1. Escherichia | Coli NIHJ | |
| 2. Escherichia | Coli NIHJ | JC-2 (IFO 12734) |
| 3. Klebsiella | pneumoniae | |
| 4. Klebsiella | pneumoniae | ST-101 |
| 5. Proteus | rettgeri NIH | 96 |
| 6. Proteus | morganii IID | Kono |
| 7. Proteus | vulgaris IID | OX-19 |
| 8. Enterobacter | aerogenes | IFO 12979 |
| 9. Enterobacter | cloacae | |
| 10. Yersinia | enterocolitica | 0-3 |
| 11. Yersinia | enterocolitica | 0-5 |
| 12. Hafnia | alvei | IFO 3731 |
| 13. Pseudomonas | aeruginosa | E-2 |
| 14. Pseudomonas | aeruginosa | NCTC 10490 |
| 15. Pseudomonas | aeruginosa | ATCC 10145 |
| 16. Pseudomonas | maltophilia | IFO 12692 |
| 17. Pseudomonas | putida | IFO 13696 |
| 18. Salmonella | typhi | 0-901 (NCTC 8393) |
| 19. Shigella | Sonnei | EW 33 |
| 20. Serattia | marcescens | IFO 12648 |
| 21. Bacillus | subtilis | PCI 219 |
| 22. Staphylococcus | aureus | FDA 209 P |
| 23. Streptococcus | pyogenes | IID S-23 |
| 24. Streptococcus | pyogenes | IID Cook |
| 25. Streptococcus | pneumoniae | Type I |
| 26. Streptococcus | pneumoniae | Type II |
| 27. Streptococcus | pneumoniae | Type III |
| 28. Corinebacterium | diphteriae | |

3. TEST COMPOUND

| | |
|---|---|
| Compound A (Invention) | 8-(1-Piperazinyl)-5-methyl-6,7-dihydro-1-oxo-1H,5H—benzo[ij]quinolizine-2-carboxylic acid hydrochloride |
| Compound B (Invention) | 8-(1-Piperazinyl)-6,7-dihydro-1-oxo-1H,5H—benzo[ij]quinolizine-2-carboxylic acid hydrochloride |
| Compound C (Invention) | 9-(1-Piperazinyl)-2-methyl-6-oxo-1,2-dihydro-6H—pyrrolo[3,2,1-ij]quinoline-5-carboxylic acid hydrochloride |
| Compound D (Invention) | 1-(1-Piperazinyl)-7a,8,9,10,11,11a-hexahydro-4-oxo-4H—pyrido[3,2,1-jk]-carbazole-5-carboxylic acid hydrochloride |
| Compound E (Comparison) | 1-Ethyl-1,4-dihydro-7-methyl-4-oxo-1,8-naphthyridene-3-carboxylic acid (nalidixic acid) |
| Compound F (Comparison) | 9-Fluoro-5-methyl-6,7-dihydro-1-oxo-1H,5H—benzo[ij]quinolizine-2-carboxylic acid (flumequine) |
| Compound G (Comparison) | Sodium 9-chloro-2-methyl-6-oxo-1,2-dihydro-6H—pyrrolo[3,2,1-ij]quinoline-5-carboxylate |
| Compound H (Comparison) | 6-{2-[8-(4-Acetyl-1-piperazinyl)-6,7-dihydro-1-oxo-1H,5H—benzo[ij]quinolizine-2-carboxamido]-2-phenylacetamido}-3,3-dimethyl-7-oxo-4-thia-1-azabicyclo[3,2,0]heptane-2-carboxylic acid |
| Compound I (Comparison) | 6-{2-[8-(1-Piperazinyl)-6,7-dihydro-1-oxo-1H,5H—benzo[ij]quinolizine-2-carboxamido]-2-phenylacetamido}-3,3-dimethyl-7-oxo-4-thia-1-azabicyclo[3,2,0]heptane-2-carboxylic acid |
| Compound J (Comparison) | 6-{2-[8-(4-Methanesulfonyl-1-piperazinyl)-6,7-dihydro-1-oxo-1H,5H—benzo[ij]quinolizine-2-carboxamido]-2-phenylacetamido}-3,3-dimethyl-7-oxo-4-thia-1-azabicyclo[3,2,0]-heptane-2-carboxylic acid |
| Compound K (Comparison) | 6-{2-[10-Chloro-8-(1-piperazinyl)-6,7-dihydro-1-oxo-1H,5H—benzo[ij]quinolizine-2-carboxamido]-2-phenylacetamido}-3,3-dimethyl-7-oxo-4-thia-1-azabicyclo[3,2,0]heptane-2-carboxylic acid |
| Compound L (Invention) | 8-(4-Methyl-1-piperazinyl)-6,7-dihydro-1-oxo-1H,5H—benzo[ij]quinolizine-2-carboxylic acid |
| Compound M (Invention) | 8-(4-Formyl-1-piperazinyl)-6,7-dihydro-1-oxo-1H,5H—benzo[ij]quinolizine-2-carboxylic acid |
| Compound N (Invention) | 8-(4-Benzoyl-1-piperazinyl)-6,7-dihydro-1-oxo-1H,5H—benzo[ij]quinolizine-2-carboxylic acid |
| Compound O (Invention) | 8-(4-Methanesulfonyl-1-piperazinyl)-6,7-dihydro-1-oxo-1H,5H—benzo[ij]quinolizine-2-carboxylic acid |
| Compound P (Invention) | 9-Chloro-8-(1-piperazinyl)-6,7-dihydro-1-oxo-1H,5H—benzo[ij]quinolizine-2-carboxylic acid hydrochloride |
| Compound Q (Invention) | 9-(1-Piperazinyl)-6-oxo-1,2-dihydro-6H—pyrrolo[3,2,1-ij]quinoline-5-carboxylic acid hydrochloride |
| Compound R (Invention) | 8-(4-Benzyl-1-piperazinyl)-6,7-dihydro-1-oxo-1H,5H—benzo[ij]quinolizine-2-carboxylic acid |
| Compound S (Invention) | 8-(4-p-Toluenesulfonyl-1-piperazinyl)-6,7-dihydro-1-oxo-1H,5H—benzo[ij]quinolizine-2-carboxylic acid |
| Compound T (Invention) | 8-(1-Piperazinyl)-9-chloro-5-methyl-6,7-dihydro-1-oxo-1H,5H—benzo[ij]quinolizine-2-carboxylic acid hydrochloride hydrate |
| Compound U (Invention) | 8-(4-Methyl-1-piperazinyl)-9-chloro-5-methyl-6,7-dihydro-1-oxo-1H,5H—benzo[ij]-quinolizine-2-carboxylic acid |
| Compound V (Invention) | 8-(4-Formyl-1-piperazinyl)-9-chloro-5-methyl-6,7-dihydro-1-oxo-1H,5H—benzo[ij]-quinolizine-2-carboxylic acid |
| Compound W (Invention) | 8-(4-Methyl-1-piperazinyl)-9-fluoro-5-methyl-6,7-dihydro-1-oxo-1H,5H—benzo[ij]-quinolizine-2-carboxylic acid |
| Compound X (Invention) | 8-(1-Piperazinyl)-9-fluoro-5-methyl-6,7-dihydro-1-oxo-1H,5H—benzo[ij]quinolizine-2-carboxylic acid hydrobromide |
| Compound Y (Invention) | 8-Chloro-9-(1-piperazinyl)-2-methyl-6-oxo-1,2-dihydro-6H—pyrrolo[3,2,1-ij]-quinoline-5-carboxylic acid |
| Compound Z (Invention) | 8-Chloro-9-(4-methyl-1-piperazinyl)-2-methyl-6-oxo-1,2-dihydro-6H—pyrrolo[3,2,1-ij]-quinoline-5-carboxylic acid |
| Compound a (Invention) | 8-Fluoro-9-(4-methyl-1-piperazinyl)-2-methyl-6-oxo-1,2-dihydro-6H—pyrrolo[3,2,1-ij]-quinoline-5-carboxylic acid |
| Compound b (Invention) | 8-(4-Trifluoroacetyl-1-piperazinyl)-9-chloro-5-methyl-6,7-dihydro-1-oxo-1H,5H—benzo[ij]quinolizine-2-carboxylic acid |
| Compound c (Invention) | 8-[4-(2-Trifluoroethyl)-1-piperazinyl]-9-chloro-5-methyl-6,7-dihydro-1-oxo-1H,5H—benzo[ij]quinolizine-2-carboxylic acid |
| Compound d (Invention) | 8-(4-Pentafluoropropionyl-1-piperazinyl)-9-chloro-5-methyl-6,7-dihydro-1-oxo-1H,5H—benzo[ij]quinolizine-2-carboxylic acid |
| Compound e (Invention) | 8-(4-Pentafluorobutyryl-1-piperazinyl)-9-chloro-5-methyl-6,7-dihydro-1oxo-1H,5H—benzo[ij]quinolizine-2-carboxylic acid |
| Compound f (Invention) | 8-[4-(2-Hydroxyethyl)-1-piperazinyl]-9-fluoro-5-methyl-6,7-dihydro-1-oxo-1H,5H—benzo[ij]quinolizine-2-carboxylic acid |
| Compound g (Invention) | 8-[4-(4-Methoxybenzyl)-1-piperazinyl]-9-chloro-5-methyl-6,7-dihydro-1-oxo-1H,5H—benzo[ij]quinolizine-2-carboxylic acid |
| Compound h (Invention) | 8-(4-Allyl-1-piperazinyl)-9-chloro-5-methyl-6,7-dihydro-1-oxo-1H,5H—benzo[ij]-quinolizine-2-carboxylic acid |
| Compound i | 8-[4-(2-Propynyl)-1-piperazinyl]-9-chloro-5-methyl-6,7-dihydro-1-oxo-1H,5H—benzo[ij]-quinolizine-2-carboxylic acid |

TABLE 1

Minimum Inhibitory Concentration (μg/ml)

Test Or-       Test Compound

TABLE 1-continued

| Test Organism | Minimum Inhibitory Concentration (µg/ml) | | | | | | | | | | | |
|---|---|---|---|---|---|---|---|---|---|---|---|---|
| | A | | B | | C | | D | | E | | F | |
| | $1 \times 10^8$ | $1 \times 10^6$ | $1 \times 10^8$ | $1 \times 10^6$ | $1 \times 10^8$ | $1 \times 10^6$ | $1 \times 10^8$ | $1 \times 10^6$ | $1 \times 10^8$ | $1 \times 10^6$ | $1 \times 10^8$ | $1 \times 10^6$ |
| 1 | 0.8 | 0.4 | 1.6 | 0.8 | 0.8 | 0.4 | | | 3.1 | 1.6 | 0.2 | 0.1 |
| 2 | 1.6 | 1.6 | 3.1 | 3.1 | 1.6 | 1.6 | | | 3.1 | 3.1 | 0.8 | 0.4 |
| 3 | 1.6 | 1.6 | 6.3 | 1.6 | 0.8 | 0.8 | | | 3.1 | 3.1 | 0.8 | 0.4 |
| 4 | 0.4 | 0.2 | 1.6 | 1.6 | 0.8 | 0.2 | | | 1.6 | 1.6 | 0.2 | 0.1 |
| 5 | 0.4 | 0.4 | 1.6 | 1.6 | 0.8 | 0.8 | | | 1.6 | 0.8 | 0.2 | 0.1 |
| 6 | 6.3 | 3.1 | 12.5 | 6.3 | 3.1 | 3.1 | | | 6.3 | 3.1 | 0.8 | 0.4 |
| 7 | 1.6 | 0.8 | 12.5 | 1.6 | 3.1 | 0.8 | | | 3.1 | 3.1 | | |
| 8 | 0.8 | 0.8 | | | 0.8 | 0.4 | | | 6.3 | 3.1 | 0.4 | 0.2 |
| 9 | 0.8 | 0.8 | | | 0.8 | 0.4 | | | 3.1 | 3.1 | 0.4 | 0.2 |
| 10 | 3.1 | 1.6 | 12.5 | 3.1 | 1.6 | 1.6 | | | 12.5 | 1.6 | 0.8 | 0.4 |
| 11 | 0.8 | 0.8 | | | 1.6 | 1.6 | | | 3.1 | 1.6 | 0.4 | 0.4 |
| 12 | 6.3 | 3.1 | | | 1.6 | 0.8 | | | 100 | 50 | 25 | 125 |
| 13 | 12.5 | 6.3 | | | 6.3 | 3.1 | | | >100 | >100 | 50 | 50 |
| 14 | 6.3 | 3.1 | | | 6.3 | 3.1 | | | >100 | >100 | 25 | 12.5 |
| 15 | 6.3 | 6.3 | 12.5 | 6.3 | 6.3 | 6.3 | | | >100 | >100 | 25 | 12.5 |
| 16 | 12.5 | 12.5 | | | 6.3 | 6.3 | | | >100 | >100 | 25 | 25 |
| 17 | 3.1 | 1.6 | | | 3.1 | 3.1 | | | 100 | 50 | 25 | 125 |
| 18 | 0.4 | 0.2 | 0.8 | 0.8 | 0.4 | 0.2 | | | 3.1 | 3.1 | 0.2 | 0.2 |
| 19 | 0.8 | 0.4 | 1.6 | 1.6 | 1.6 | 1.6 | | | 3.1 | 3.1 | 0.8 | 0.8 |
| 20 | 3.1 | 1.6 | 6.3 | 3.1 | 3.1 | 1.6 | | | 3.1 | 3.1 | 0.8 | 0.4 |
| 21 | 0.8 | 0.8 | 12.5 | 12.5 | 3.1 | 3.1 | | | 6.3 | 3.1 | 0.4 | 0.2 |
| 22 | 6.3 | 3.1 | 2.5 | 12.5 | 25 | 25 | | | 50 | 50 | 3.1 | 1.6 |
| 23 | 25 | 12.5 | | | 100 | 50 | | | >100 | >100 | >100 | >100 |
| 24 | 25 | 12.5 | | | 50 | 25 | | | >100 | >100 | >100 | >100 |
| 25 | 12.5 | 3.1 | | | 100 | 50 | | | >100 | >100 | >100 | >100 |
| 26 | 25 | 6.3 | | | 100 | 50 | | | >100 | >100 | >100 | >100 |
| 27 | 25 | 12.5 | | | 100 | 50 | | | >100 | >100 | >100 | >100 |
| 28 | 1.6 | 1.6 | | | 25 | 6.3 | | | >100 | >100 | >25 | >6.3 |

| Test Organism | Test Compound | | | | | | | | | |
|---|---|---|---|---|---|---|---|---|---|---|
| | G | | H | | I | | J | | K | |
| | $1 \times 10^8$ | $1 \times 10^6$ | $1 \times 10^8$ | $1 \times 10^6$ | $1 \times 10^8$ | $1 \times 10^6$ | $1 \times 10^8$ | $1 \times 10^6$ | $1 \times 10^8$ | $1 \times 10^6$ |
| 1 | 0.8 | 0.4 | 6.3 | | 1.6 | | 3.1 | | 6.3 | |
| 2 | | | | | | | | | | |
| 3 | 3.1 | 1.6 | 12.5 | | 0.8 | | 6.3 | | 6.3 | |
| 4 | | | | | | | | | | |
| 5 | 0.4 | 0.2 | 25 | | 0.4 | | 12.5 | | 12.5 | |
| 6 | | | | | | | | | | |
| 7 | | | | | | | | | | |
| 8 | | | | | | | | | | |
| 9 | | | | | | | | | | |
| 10 | | | | | | | | | | |
| 11 | | | | | | | | | | |
| 12 | | | | | | | | | | |
| 13 | 100 | 50 | 25 | | 25 | | 25 | | 25 | |
| 14 | 25 | 12.5 | 3.1 | | 6.3 | | 3.1 | | 3.1 | |
| 15 | 50 | 25 | 12.5 | | 25 | | 12.5 | | 12.5 | |
| 16 | | | | | | | | | | |
| 17 | | | | | | | | | | |
| 18 | 0.8 | 0.8 | 6.3 | | 0.2 | | 3.1 | | 3.1 | |
| 19 | 1.6 | 1.6 | 12.5 | | 3.1 | | 6.3 | | 3.1 | |
| 20 | 3.1 | 1.6 | 50 | | 12.5 | | 50 | | 12.5 | |
| 21 | | | | | | | | | | |
| 22 | 3.1 | 3.1 | 1.6 | | 0.1 | | 0.8 | | 0.8 | |
| 23 | >100 | >100 | | | | | | | | |
| 24 | | | | | | | | | | |
| 25 | | | | | | | | | | |
| 26 | | | | | | | | | | |
| 27 | | | | | | | | | | |
| 28 | | | | | | | | | | |

TABLE 1A

| Test Compound | | Minimum Inhibitory Concentration (µg/ml) | | | | | | | | | | |
|---|---|---|---|---|---|---|---|---|---|---|---|---|
| | | Test Organism | | | | | | | | | | |
| | | 2 | 3 | 5 | 13 | 14 | 15 | 18 | 19 | 20 | 22 | 23 |
| L | $1 \times 10^8$ | 1.6 | 6.3 | 3.1 | 50 | 50 | 50 | 3.1 | 3.1 | 6.3 | 6.3 | — |
| | $1 \times 10^6$ | — | — | — | — | — | — | — | — | — | — | — |
| M | $1 \times 10^8$ | 1.6 | 3.1 | 1.6 | 25 | 12.5 | 25 | 0.8 | 1.6 | 3.1 | 3.1 | — |
| | $1 \times 10^6$ | — | — | — | — | — | — | — | — | — | — | — |
| N | $1 \times 10^8$ | 6.3 | 6.3 | 6.3 | 100 | 25 | 50 | 1.6 | 3.1 | 12.5 | 3.1 | — |
| | $1 \times 10^6$ | — | — | — | — | — | — | — | — | — | — | — |
| O | $1 \times 10^8$ | 6.3 | 6.3 | 6.3 | 100 | 25 | 100 | 1.6 | 6.3 | 12.5 | 3.1 | — |
| | $1 \times 10^6$ | — | — | — | — | — | — | — | — | — | — | — |
| P | $1 \times 10^8$ | 1.6 | 0.8 | 0.4 | 6.3 | 6.3 | 6.3 | 0.8 | 1.6 | 1.6 | 6.3 | — |

TABLE 1A-continued

| Test Compound | | Minimum Inhibitory Concentration (μg/ml) Test Organism | | | | | | | | | |
|---|---|---|---|---|---|---|---|---|---|---|---|
| | | 2 | 3 | 5 | 13 | 14 | 15 | 18 | 19 | 20 | 22 | 23 |
| Q | $1 \times 10^6$ | — | — | — | — | — | — | — | — | — | — | — |
| | $1 \times 10^8$ | 25 | 12.5 | 25 | 50 | 25 | 50 | 6.3 | 3.1 | 6.3 | 100 | — |
| R | $1 \times 10^6$ | — | — | — | — | — | — | — | — | — | — | — |
| | $1 \times 10^8$ | 1.6 | 3.1 | 1.6 | 25 | 12.5 | 25 | 1.6 | 1.6 | 3.1 | 12.5 | — |
| S | $1 \times 10^6$ | — | — | — | — | — | — | — | — | — | — | — |
| | $1 \times 10^8$ | 1.6 | 3.1 | 3.1 | 50 | 12.5 | 25 | 1.6 | 3.1 | 6.3 | 6.3 | — |
| T | $1 \times 10^6$ | — | — | — | — | — | — | — | — | — | — | — |
| | $1 \times 10^8$ | 0.4 | 0.4 | 0.2 | 3.1 | 1.6 | 3.1 | 0.2 | 0.2 | 1.6 | 1.6 | 6.3 |
| | $1 \times 10^6$ | 0.4 | 0.4 | 0.2 | 3.1 | 1.6 | 1.6 | 0.1 | 0.2 | 1.6 | 1.6 | 3.1 |
| U | $1 \times 10^8$ | 0.2 | 0.2 | 0.4 | 6.3 | 1.6 | 3.1 | ≦0.05 | 0.2 | 0.4 | 0.8 | 3.1 |
| | $1 \times 10^6$ | 0.2 | 0.2 | 0.4 | 6.3 | 1.6 | 3.1 | ≦0.05 | 0.1 | 0.4 | 0.4 | 3.1 |
| V | $1 \times 10^8$ | 0.8 | 0.8 | 0.8 | 12.5 | 3.1 | 12.5 | 0.2 | 0.8 | 3.1 | 0.2 | 3.1 |
| | $1 \times 10^6$ | 0.8 | 0.8 | 0.8 | 6.3 | 1.6 | 12.5 | 0.2 | 0.4 | 3.1 | 0.2 | 1.6 |
| W | $1 \times 10^8$ | 0.4 | 0.4 | 0.4 | 6.3 | 1.6 | 3.1 | 0.1 | 0.2 | 0.4 | 0.4 | 1.6 |
| | $1 \times 10^6$ | 0.4 | 0.2 | 0.4 | 3.1 | 1.6 | 1.6 | ≦0.05 | 0.2 | 0.4 | 0.4 | 1.6 |
| X | $1 \times 10^8$ | 0.4 | 0.4 | 0.1 | 1.6 | 1.6 | 1.6 | 0.1 | 0.2 | 0.8 | 0.8 | 3.1 |
| Y | $1 \times 10^6$ | — | — | — | — | — | — | — | — | — | — | — |
| | $1 \times 10^8$ | 0.2 | 0.4 | 0.2 | 3.1 | 1.6 | 1.6 | 0.1 | 0.1 | 0.8 | 3.1 | 12.5 |
| | $1 \times 10^6$ | 0.2 | 0.2 | 0.1 | 3.1 | 1.6 | 1.6 | ≦0.05 | ≦0.05 | 0.4 | 3.1 | 6.3 |
| Z | $1 \times 10^8$ | 0.2 | 0.2 | 0.4 | 6.3 | 3.1 | 3.1 | 0.1 | 0.2 | 0.4 | 0.8 | 12.5 |
| | $1 \times 10^6$ | 0.2 | 0.2 | 0.2 | 3.1 | 3.1 | 3.1 | 0.1 | 0.2 | 0.4 | 0.4 | 6.3 |
| a | $1 \times 10^8$ | 0.1 | 0.2 | 0.2 | 1.6 | 1.6 | 1.6 | ≦0.05 | 0.1 | 0.2 | 0.8 | 6.3 |
| | $1 \times 10^6$ | 0.1 | 0.2 | 0.1 | 1.6 | 1.6 | 1.6 | ≦0.05 | 0.1 | 0.2 | 0.4 | 3.1 |
| b | $1 \times 10^8$ | 0.39 | 0.39 | 0.2 | 3.13 | 1.56 | 3.13 | 0.39 | 1.56 | 1.56 | 3.13 | 6.25 |
| c | $1 \times 10^6$ | — | — | — | — | — | — | — | — | — | — | — |
| | $1 \times 10^8$ | 0.39 | 0.39 | 0.39 | 6.25 | 0.78 | 3.13 | 0.2 | 1.56 | 0.39 | 0.1 | 1.56 |
| d | $1 \times 10^6$ | — | — | — | — | — | — | — | — | — | — | — |
| | $1 \times 10^8$ | 0.39 | 0.39 | 0.2 | 6.25 | 3.13 | 1.56 | 0.1 | 0.78 | 0.2 | 1.56 | 12.5 |
| e | $1 \times 10^6$ | — | — | — | — | — | — | — | — | — | — | — |
| | $1 \times 10^8$ | 0.39 | 0.39 | 0.2 | 6.25 | 3.13 | 1.56 | 0.2 | 0.78 | 0.2 | 3.13 | 6.25 |
| f | $1 \times 10^6$ | — | — | — | — | — | — | — | — | — | — | — |
| | $1 \times 10^8$ | 0.39 | 0.78 | 0.2 | 12.5 | 12.5 | 6.25 | 0.39 | 0.78 | 0.39 | 0.78 | 3.13 |
| g | $1 \times 10^6$ | — | — | — | — | — | — | — | — | — | — | — |
| | $1 \times 10^8$ | 0.78 | 0.78 | 0.1 | 12.5 | 12.5 | 6.25 | 0.78 | 1.56 | 0.39 | 0.78 | 3.13 |
| h | $1 \times 10^6$ | — | — | — | — | — | — | — | — | — | — | — |
| | $1 \times 10^8$ | 0.78 | 0.78 | 0.2 | 12.5 | 12.5 | 12.5 | 0.78 | 1.56 | 0.78 | 0.78 | 3.13 |
| i | $1 \times 10^6$ | — | — | — | — | — | — | — | — | — | — | — |
| | $1 \times 10^8$ | 1.56 | 0.78 | 0.2 | 25 | 12.5 | 12.5 | 0.78 | 1.56 | 0.78 | 0.39 | 1.56 |
| | $1 \times 10^6$ | — | — | — | — | — | — | — | — | — | — | — |

In the same manner as above, the antimicrobial activity of the following compounds on various test organisms which cause infectious diseases in fish was determined. The results obtained are shown in Table 2 below.

II. INFLUENCE OF THE ADDITION OF HORSE SERUM ON THE MINIMUM INHIBITORY CONCENTRATION OF QUINOLINE DERIVATIVES

Minimum inhibitory concentration of test compounds A, C and F on various test organisms shown in Table 3 was determined. The determination was conducted by

TABLE 2

Antimicrobial Activity on Bacteria which Cause Infectious Diseases in Fish

| | Minimum Inhibitory Concentration (μg/ml) Test Compound | | | | | | | |
|---|---|---|---|---|---|---|---|---|
| | B | | A | | C | | E | |
| Test Organism | $10^8$ | $10^6$ | $10^8$ | $10^6$ | $10^8$ | $10^6$ | $10^8$ | $10^6$ |
| *Aeromonas hydrophila* IFO 12658 | 1.6 | 0.8 | 0.2 | 0.1 | 0.4 | 0.2 | 0.8 | 0.8 |
| *Aeromonas hydrophila* IFO 12981 | 0.8 | 0.4 | 0.2 | 0.2 | 0.4 | 0.2 | 0.4 | 0.2 |
| *Aeromonas salmonicida* IFO 12659 | 1.6 | 0.8 | 0.4 | 0.2 | 0.4 | 0.2 | 0.8 | 0.8 |
| *Aeromonas salmonicida* IFO 12718 | 0.8 | 0.4 | 0.4 | 0.2 | 0.4 | 0.4 | 0.8 | 0.8 |
| *Pseudomonas fluorescens* IFO 12180 | 6.3 | 6.3 | 3.1 | 3.1 | 3.1 | 3.1 | >50 | 50 |
| *Pseudomonas fluorescens* IFO 12568 | 50 | 25 | 25 | 12.5 | 50 | 25 | >50 | 50 |
| *Vibrio anguillarum* IFO 12710 | 12.5 | 3.1 | 3.1 | 3.1 | 3.1 | 1.6 | 1.6 | 0.8 |
| *Vibrio anguillarum* IFO 13266 | 0.8 | 0.4 | 0.2 | 0.1 | 0.4 | 0.2 | 1.6 | 0.8 | evaluating minimum inhibitory concentration of each test compound by serial dilution plate method using a culture medium of Heart Infusion Agar (a product of Difco Co.) containing horse serum at a final concentration of 0, 10, 20 or 40% by volume with inoculum size of the test organism being $10^8$ cells/ml (*Chemotherapy*, 22, pp. 1126-1128 (1974)).

The results are shown in Table 3 below.

TABLE 3

Influence of the Addition of Horse Serum on the MIC of Quinoline Derivatives

Minimum Inhibitory Concentration (mcg/ml)

| Test Compound | Serum Conc. (%) | Test Organism | | | | | | | | | | | |
|---|---|---|---|---|---|---|---|---|---|---|---|---|---|
| | | 1 | | 2 | | 17 | | 16 | | 21 | | 27 | |
| | | $10^8$ | $10^6$ | $10^8$ | $10^6$ | $10^8$ | $10^6$ | $10^8$ | $10^6$ | $10^8$ | $10^6$ | $10^8$ | $10^6$ |
| F | 0 | 1.6 | 1.6 | 0.8 | 0.8 | 0.2 | 0.1 | 0.8 | 0.8 | 0.8 | 0.8 | 50 | 50 |
| | 10 | 3.1 | 3.1 | 0.8 | 0.8 | 0.4 | 0.2 | 0.8 | 0.4 | 0.8 | 0.8 | >50 | 50 |
| | 20 | 6.3 | 3.1 | 0.8 | 0.8 | 0.2 | 0.2 | 0.8 | 1.6 | 0.8 | 0.8 | >50 | 50 |
| | 40 | 12.5 | 12.5 | 1.6 | 1.6 | 0.2 | 0.2 | 1.6 | 1.6 | 1.6 | 1.6 | >50 | 50 |
| C | 0 | 12.5 | 12.5 | 1.6 | 1.6 | 0.8 | 0.4 | 1.6 | 1.6 | 3.1 | 1.6 | 6.3 | 3.1 |
| | 10 | 12.5 | 6.3 | 1.6 | 1.6 | 0.8 | 0.4 | 1.6 | 1.6 | 1.6 | 1.6 | 6.3 | 3.1 |
| | 20 | 12.5 | 6.3 | 0.8 | 1.6 | 0.8 | 0.4 | 0.8 | 0.4 | 1.6 | 1.6 | 3.1 | 3.1 |
| | 40 | 12.5 | 6.3 | 0.4 | 0.4 | 0.4 | 0.4 | 0.4 | 0.4 | 0.8 | 0.4 | 3.1 | 1.6 |
| A | 0 | 6.3 | 6.3 | 1.6 | 1.6 | 0.4 | 0.2 | 3.1 | 1.6 | 6.3 | 3.1 | 12.5 | 6.3 |
| | 10 | 6.3 | 3.1 | 0.8 | 0.8 | 0.2 | 0.2 | 1.6 | 1.6 | 3.1 | 3.1 | 6.3 | 6.3 |
| | 20 | 3.1 | 3.1 | 0.8 | 0.8 | 0.2 | 0.2 | 0.8 | 0.8 | 1.6 | 0.8 | 6.3 | 6.3 |
| | 40 | 3.1 | 3.1 | 0.4 | 0.4 | 0.2 | 0.2 | 0.8 | 0.4 | 0.8 | 0.8 | 6.3 | 3.1 |

III. INACTIVATION RATIO BY HUMAN SERUM PROTEIN

A 1/15 mol/l phosphate buffer was added to powder of Moni-Trol 1 (dehydrated preparation of human serum, a product of Midori Juji Co., Ltd.) to prepare a composition having the same serum protein concentration as natural human serum and this preparation was labeled "100% human serum", an aliquot of the "100% human serum" preparation was mixed with the same volume of the above buffer to prepare "50% human serum" and another aliquot was mixed with 4 times as much as its volume of the buffer to prepare "20% human serum".

Each of test compounds A and E was dissolved in an appropriate amount of the above serum preparations such that the final concentrations were 12.5 μg/ml and 3.1 μg/ml. After incubating the resulting preparations at 37° C. for 2 hours, the amount of active component was evaluated by determining the activity of the test compound in the human serum on Escherichia coli As-19 (Inoculum size: $10^6$ cells/ml).

The Inactivation Ratio of test compounds A and E in human serum was calculated in accordance with the following equation.

$$\text{Inactivation Ratio} = \frac{C_0 - C}{C_0} \times 100$$

wherein Co indicates the concentration of test compound in the absence of the serum, and C the concentration of active component in the serum.

The results obtained are shown in Table 4 below.

TABLE 4

Inactivation by Human Serum Protein

| Test Compound | Concentration (mcg/ml) | Inactivation Ratio (%) Serum Concentration | | | |
|---|---|---|---|---|---|
| | | 100(%) | 50(%) | 20(%) | 10(%) |
| A | 12.5 | −2.5 | −17.9 | −2.5 | −2.5 |
| | 3.1 | 0 | −26.5 | 0 | 8.2 |
| E | 12.5 | 76 | 62.4 | 39.2 | 47.2 |

TABLE 4-continued

Inactivation by Human Serum Protein

| Test Compound | Concentration (mcg/ml) | Inactivation Ratio (%) Serum Concentration | | | |
|---|---|---|---|---|---|
| | | 100(%) | 50(%) | 20(%) | 10(%) |
| | 3.1 | 61.3 | 61.3 | 43.5 | 41.3 |

ACUTE TOXICITY

The acute toxicity of the compounds of this invention having the formula (I) was determined by intravenous administration (i.v.) in mice which had not been fed for 12 hours prior to the test. $LD_{50}$ values (50% lethal dose) obtained are set forth below:

| Acute Toxicity | |
|---|---|
| Test Compound | $LD_{50}$ (i.v.) (mg/kg) |
| B | 1,100 |

In the same manner as above, $LD_{50}$ values were determined for all the other test compounds and the $LD_{50}$ values obtained were at least 500 mg/kg.

The present invention is further illustrated by the following Reference Examples and Examples, but they are not to be construed as limiting the scope of this invention. The antimicrobial activity of typical compounds of the present invention is also shown in Examples. Unless otherwise indicated, all parts, percents and ratios are by weight.

Unless otherwise indicated Elemental Analysis was carried out at a temperature of from 70° C. to 80° C. at reduced pressure (1 to 2 mmHg) for 6 hours, using $P_2O_5$ as a desiccant.

REFERENCE EXAMPLE 1

10 g of 5-hydroxy-3,4-dihydrocarbostyril was added to 100 ml of methanol having dissolved therein 3.8 g of potassium hydroxide and the mixture was stirred at room temperature for 30 minutes followed by removing methanol under reduced pressure. Benzene was added to the residue to form crystals and then benzene was removed by evaporation. The residue thus-obtained was suspended in 50 ml of dimethylformamide and 10.6 g of methanesulfonyl chloride was added dropwise to the suspension while ice-cooling with stirring. After adding 3.5 g of methanesulfonyl chloride the resulting mixture was stirred at room temperature for 4 hours. After the completion of the reaction, the solvent was removed under reduced pressure and the residue was purified through silica gel column chromatography (silica gel: Wako C-200, a trade name for a product of Wako Junyaku Co., Ltd.; eluent: chloroform). Recrystallization of the elute from water-containing ethanol gave 5.7 g of 5-methanesulfonyloxy-3,4-dihydrocarbostyril as colorless prismatic crystals having a melting point of 227° to 231° C.

REFERENCE EXAMPLE 2

In an analogous manner as in Reference Example 1, 5-(p-toluenesulfonyloxy)-3,4-dihydrocarbostyril having a melting point of 215° to 216° C. was obtained.

REFERENCE EXAMPLE 3

45 g of 5-amino-3,4-dihydrocarbostyril was suspended in 250 ml of a 15% hydrochloric acid and 250 ml of water having dissolved therein 20 g of sodium nitrite was added dropwise to the mixture followed by stirring at room temperature for 1 hour. The resulting solution was added dropwise to a solution prepared by dissolving 41.2 g of cuprous chloride in 120 ml of concentrated hydrochloric acid at room temperature while stirring. After completion of the addition, the mixture was heated on a water bath at 50° to 60° C. for 1 hour while stirring. After allowing the mixture to cool to precipitate crystals, they were collected by filtration and washed with water. The wet crystals were dissolved in chloroform and insoluble materials were removed by filtration. The residue was dried over anhydrous sodium sulfate. After removal of the solvent the residue was dissolved with heating and the solution was treated with activated carbon while hot. The ethanolic solution thus-treated was concentrated under reduced pressure. Recrystallization of the concentrate from ethanol gave 31.5 g of 5-chloro-3,4-dihydrocarbostyril having a melting point of 193° to 194° C.

REFERENCE EXAMPLE 4

42.5 g of 5-chloro-3,4-dihydrocarbostyril was suspended in 250 ml of dioxane and 44.3 g of $NaBH_4$ was added to the suspension. Then 67 ml of acetic acid (d=1.05) was added dropwise to the mixture at room temperature. After heat-refluxing the resulting mixture for 2 hours the solvent was removed under reduced pressure. Water was added to the residue and insoluble materials were removed by filtration followed by washing with diethyl ether. The residue was extracted with diethyl ether, dried over anhydrous sodium sulfate and distilled under reduced pressure to obtain 36.0 g of 5-chloro-1,2,3,4-tetrahydroquinoline having a boiling point of 116° to 120° C./0.2 mmHg.

REFERENCE EXAMPLE 5

4.5 g of 5-methanesulfonyloxy-3,4-dihydrocarbostyril was suspended in 90 ml of dioxane and 35 g of $NaBH_4$ was added to the suspension then 5.3 ml of acetic acid was added dropwise to the mixture. After heat-refluxing the resulting mixture for 1 hour the solvent was removed under reduced pressure. A saturated aqueous solution of sodium bicarbonate was added to the residue to form precipitates which were filtered and washed with chloroform. The filtrate was extracted with chloroform and the chloroform layer was dried over $Na_2SO_4$ followed by removing the solvent. The residue was purified through a silica gel column chromatography (silica gel: Wako C-200, a trade name for a product of Wako Junyaku Co., Ltd.; eluent: chloroform) and the eluate thus-obtained was crystallized from petroleum ether. Recrystallization of the crystals thus-obtained from methanol gave 1.9 g of 5-methanesulfonyloxy-1,2,3,4-tetrahydroquinoline, colorless prisms having a melting point of 74° to 76° C.

REFERENCE EXAMPLE 6

In an analogous manner as in Reference Example 5, 5-(p-toluenesulfonyloxy)-1,2,3,4-tetrahydroquinoline having a melting point of 112° to 113° C. was obtained.

REFERENCE EXAMPLE 7

5.5 g of 4-chlorooxindole was dissolved in 80 ml of dioxane and 6.2 g of sodium borohydride was suspended in the resulting solution and 12.7 ml of trifluoroacetic acid (d=1.48) was added thereto dropwise at room temperature while stirring. After heat-refluxing the mixture for 4.5 hours the solvent was removed therefrom under reduced pressure. Water was added to the residue and water-insoluble materials were removed by filtration and washed with diethyl ether. The filtrate was extracted with diethyl ether and the ether layer was dried over anhydrous sodium sulfate followed by removing the solvent. The residue was distilled under reduced pressure to obtain 3.9 g of 4-chloroindoline as a colorless oily product having a boiling point of 135° C. at 10 mmHg.

REFERENCE EXAMPLE 8

5 g of sodium borohydride was added to 66 ml of pyridine having dissolved therein 4.4 g of 2-methyl-4-chloroindole. To the mixture were added gradually 10.6 g of fine powders of aluminum chloride while ice-cooling with stirring. After completion of addition the mixture was stirred and allowed to react at room temperature for 27 hours, the solvent was removed therefrom under reduced pressure. Water was added to the residue and the mixture was extracted with 100 ml of benzene. The benzene layer was washed with a saturated aqueous sodium chloride solution followed by concentration. To the residue was added a 10% aqueous hydrochloric acid which caused foaming. After foaming ceased the mixture was rendered neutral with an aqueous sodium carbonate solution followed by extracting the mixture with 100 ml of benzene. The benzene layer was dried over anhydrous sodium sulfate. After removing the solvent under reduced pressure the extract was purified through a silica gel column chromatography (eluent:chloroform) to obtain 3.4 g of 2-methyl-4-chloroindoline which was confirmed by NMR.

REFERENCE EXAMPLE 9

21.6 g of ethyl ethoxymethylenemalonate was added to 22.4 g of 5-methanesulfonyloxy-1,2,3,4-tetrahydroquinoline and the mixture was heated at 110° C. on an oil bath for 30 minutes while stirring, during which time distillation of ethanol was observed. After heating, 240 g of polyphosphoric acid prepared from 120 g of phosphoric acid and 120 g of phosphorus pentoxide was added to the mixture and the mixture was allowed to react on an oil bath at 140° C. for 45 minutes. After completion of the reaction, the mixture was allowed to cool to room temperature and poured into 400 ml of water, followed by rendering the mixture neutral with a 40% aqueous sodium hydroxide solution to precipitate crystals. The crystals thus-obtained were mixed with 150 ml of a 10% aqueous sodium hydroxide solution and the mixture was heat refluxed for 40 minutes during which time the crystals were dissolved to form a uniform solution. The solution was treated with activated carbon while hot and filtered. The filtrate was allowed to cool and adjusted to a pH of 2 to precipitate crystals which were filtered. Recrystallization of the crude crystals thus-obtained from dimethylformamide gave 21.3 g of 8-methanesulfonyloxy-6,7-dihydro-1-oxo-1H,5H-benzo[ij]quinolizine-2-carboxylic acid as white needles having a melting point of 270° to 275° C.

REFERENCE EXAMPLE 10

21.6 g of ethyl ethoxymethylenemalonate was added to 30.0 g of 5-(p-toluenesulfonyloxy)-1,2,3,4-tetrahydroquinoline and the mixture was heated at 110° C. on an oil bath for 30 minutes while stirring, during which time distillation of ethanol was observed. After heating, 240 g of polyphosphoric acid prepared from 120 g of phosphoric acid and 120 g of phosphorus pentoxide was added to the mixture and the mixture was allowed to react on an oil bath at 140° C. for 40 minutes. After completion of the reaction, the mixture was allowed to cool to room temperature and poured into 400 ml of water, followed by rendering the mixture neutral with a 40% aqueous sodium hydroxide to precipitate crystals. The crystals thus-obtained were mixed with 150 ml of a 10% aqueous sodium hydroxide solution and the mixture was heat refluxed for 40 minutes during which time the crystals were dissolved to form a uniform solution. The solution was filtered and the filtrate was allowed to cool and adjusted to a pH of 2 to precipitate crystals which were collected by filtration. Recrystallization of the crude crystals thus-obtained from dimethylformamide gave 27.4 g of an 8-(p-toluenesulfonyloxy)-6,7-dihydro-1-oxo-1H,5H-benzo-[ij]quinolizine-2-carboxylic acid as white needles having a melting point of not lower than 300° C.

REFERENCE EXAMPLE 11

To 4.4 g of diethyl ethoxymethylenemalonate was added 3 g of 4-chloroindoline and the mixture was heated on an oil bath at 110° to 120° C. during which time liberation of ethanol was observed. 20 g of polyphosphoric acid prepared from 10 g of phosphoric acid and 10 g of phosphorus pentoxide was added thereto and the mixture was heated on an oil bath at 130° to 140° C. for 40 minutes. After completion of the reaction, the mixture was allowed to cool to 60° C., poured into water and rendered neutral with a 10% aqueous sodium hydroxide solution. The crystals precipitated were collected by filtration and washed with water. The crystals thus-treated were mixed with 50 ml of a 10% aqueous sodium hydroxide solution and the mixture was heat-refluxed on an oil bath for 1 hour. As the reaction proceeded the mixture changed to a uniform solution. The solution was treated with activated carbon while hot followed by filtration. The filtrate was rendered acidic with concentrated hydrochloric acid to precipitate crystals. Recrystallization of the crystals from dimethylformamide gave 3.5 g of 9-chloro-6-oxo-1,2-dihydro-6H-pyrrolo[3,2,1-ij]quinoline-5-carboxylic acid as white needles having a melting point of 307.5° C. (decomposed).

REFERENCE EXAMPLE 12

4.4 g of diethyl ethoxymethylenemalonate was added to 3.4 g of 2-methyl-4-chloroindoline and the mixture was heated on an oil bath at 110° to 120° C. for 40 minutes. 20 g of polyphosphoric acid prepared from 10 g of phosphoric acid and 10 g of phosphorus pentoxide was added thereto and the mixture was heated on an oil bath at 130° to 140° C. for 1 hour. After completion of the reaction, the mixture was allowed to cool to 60° C., poured into ice water and rendered neutral with a 10% aqueous sodium hydroxide solution. The crystals precipitated were collected by filtration and washed with water. The crystals thus treated were mixed with 50 ml of a 10% aqueous sodium hydroxide solution and the mixture was heat-refluxed on an oil bath for 1 hour. As the reaction proceeded the mixture changed to a uniform solution. The solution was treated with activated carbon while hot followed by filtration. The filtrate was rendered acidic with concentrated hydrochloric acid to precipitate crystals. Recrystallization of the product from dimethylformamide gave 3.8 g of 9-chloro-2-methyl-6-oxo-1,2-dihydro-6H-pyrrolo[3,2,1-ij]quinoline-5-carboxylic acid as white needles having a melting point of 288° to 290° C.

REFERENCE EXAMPLE 13

25 g of ethyl ethoxymethylenemalonate was added to 21 g of 5-chloro-2-methyl-1,2,3,4-tetrahydroquinoline and the mixture was heated on an oil bath at 110° to 120° C. during which time distillation of ethanol was observed. After heating the mixture at the same temperature as above for 30 minutes 160 g of polyphosphoric acid prepared from 80 g of phosphoric acid and 80 g of phosphorus pentoxide was added thereto followed by heating on an oil bath at 130° to 140° C. for 1 hour. After completion of the reaction the reaction mixture was poured into 600 ml of water and the resulting mixture was rendered neutral with a 10% aqueous sodium hydroxide solution to precipitate crystals, which were collected by filtration and mixed with 200 ml of a 10% aqueous sodium hydroxide solution and the mixture was heat-refluxed for 1 hour during which time the crystals were dissolved to form a uniform solution. The solution was treated with activated carbon while hot and filtered. The filtrate was allowed to cool and pH was adjusted with concentrated hydrochloric acid to a pH of 2 to precipitate crystals. Recrystallization of the crude crystals thus-obtained from dimethylformamide gave 22 g of 8-chloro-5-methyl-6,7-dihydro-1-oxo-1H,5H-benzo-[ij]quinolizine-2-carboxylic acid as colorless rhombic crystals having a melting point of 290° to 291° C.

REFERENCE EXAMPLE 14

In an analogous manner as in Reference Example 13, 8-chloro-6,7-dihydro-1-oxo-1H,5H-benzo[ij]quinolizine-2-carboxylic acid as colorless needles having a melting point of not lower than 300° C. was obtained.

REFERENCE EXAMPLE 15

9 g of diethyl ethoxymethylenemalonate was added to 9 g of 5-chloro-1,2,3,4-tetrahydrocarbazole and the mixture was heated without solvent at 110° C. on an oil bath for 30 minutes while stirring, during which time distillation of ethanol was observed. After heating, 100 g of polyphosphoric acid prepared from 50 g of phosphoric acid and 50 g of phosphorus pentoxide was added to the mixture and the mixture was allowed to react on an oil bath at 140° C. for 40 minutes. After completion of the reaction, the mixture was allowed to cool to 60° C. and poured into 500 ml of ice water to precipitate light yellow crystals. The crystals thus-formed were filtered and washed with water sufficiently followed by refluxing with 100 ml of a 10% aqueous NaOH solution for 1 hour. The crystals were dissolved to give a uniform solution which was then treated with activated carbon while hot and the pH of the solution was adjusted to a pH of 2 with concentrated hydrochloric acid to obtain 9.3 g of 1-chloro-7a,8,9,10,11,11a-hexahydro-4H-pyrido[3,2,1-jk]carbazole-4-oxo-5-carboxylic acid as light yellow crystals having a melting point of 273° to 275° C.

REFERENCE EXAMPLE 16

0.78 g of 8-(1-piperazinyl)-6,7-dihydro-1-oxo-1H,5H-benzo[ij]quinolizine-2-carboxylic acid was suspended in 25 ml of anhydrous dimethylformamide and 0.42 ml of triethylamine was added to the mixture while ice cooling and stirred for 15 minutes. Then 0.4 ml of isobutyl chloroformate was added thereto dropwise and stirred for 45 minutes at the same temperature as above. On the other hand, 1.3 g of ampicillin was suspended in 15 ml of anhydrous dimethylformamide and 0.7 ml of triethylamine and 0.5 g of anhydrous magnesium sulfate were added to the suspension while ice cooling and the mixture was stirred at the same temperature as above for 30 minutes and insoluble materials were removed by filtration. The triethylamine salt of ampicillin thus-obtained was added to the former reaction mixture and stirred for 2 hours while ice cooling. After completion of the reaction, insoluble materials were removed by filtration and 2.5 ml of a 20% n-butanol solution of potassium 2-ethylhexanoate and then 300 ml of diethyl ether were added to the filtrate to precipitate crystals to obtain 0.97 g of potassium-6-{2-[8-(piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylate as light yellow amorphous crystals having a melting point of 218° to 225° C. (reddening); 245° to 250° C. (decomposed).

REFERENCE EXAMPLE 17

0.7 g of 8-(4-acetyl-1-piperazinyl)-6,7-dihydro-1-oxo-1H,5H-benzo[ij]quinolizine-2-carboxylic acid was suspended in 20 ml of dimethylformamide and 0.34 ml of triethylamine was added to the mixture while ice-cooling and stirred for 15 minutes. Then 0.32 ml of isobutyl chloroformate was added thereto dropwise and stirred for 45 minutes at the same temperature as above. On the other hand, 1 g of ampicillin was suspended in 10 ml of anhydrous dimethylformamide and 0.56 ml of triethylamine and 0.4 g of anhydrous magnesium sulfate were added to the suspension while ice-cooling and the mixture was stirred at the same temperature as above for 30 minutes and insoluble materials were removed by filtration. The triethylamine salt of ampicillin thus-obtained was added to the former reaction mixture and stirred for 2 hours while ice-cooling. After completion of the reaction, insoluble materials were removed by filtration and 2.5 ml of a 20% n-butanol solution of potassium 2-ethyl hexanoate and then 300 ml of diethyl ether were added to the filtrate to precipitate crystals. The crystals were collected by filtration and dissolved in 100 ml of water and the solution was rendered acidic (pH=3) to form precipitates, which were washed with water and dried at room temperature under reduced pressure. The product was treated in an analogous manner as in Reference Example 1 to obtain 0.75 g of 6-{2-[8-(4-acetyl-1-piperazinyl)-6,7-dihydro-1-oxo-1H,5H-benzo[ij]quinolizine-2-carboxamido]-2-(4-hydroxy)-phenylacetamido}-3,3-dimethyl-7-oxo-4-thia-1-azabicyclo[3,2,0]heptane-2-carboxylic acid as white amorphous crystals having a melting point of 214° to 219° C. (decomposed).

REFERENCE EXAMPLE 18

0.81 g of 8-(4-methanesulfonyl-1-piperazinyl)-6,7-dihydro-1-oxo-1H,5H-benzo[ij]quinolizine-2-carboxylic acid was suspended in 25 ml of dimethylformamide and 0.42 ml of triethylamine was added to the mixture while ice-cooling and stirred for 15 minutes. Then 0.4 ml of isobutyl chloroformate was added thereto dropwise and stirred for 45 minutes at the same temperature as above. On the other hand, 1.3 g of ampicillin was suspended in 15 ml of anhydrous dimethylformamide and 0.7 ml of triethylamine and 0.5 g of anhydrous magnesium sulfate were added to the suspension while ice-cooling and the mixture was stirred at the same temperature as above for 30 minutes and insoluble materials were removed by filtration. The triethylamine salt of ampicillin thus-obtained was added to the former reaction mixture and stirred for 2 hours while ice-cooling followed by treating the resulting mixture in an analogous manner as in Reference Example 17 to obtain 1.25 g of 6-{2-[8--(4-methanesulfonyl-1-piperazinyl)-6,7-dihydro-1-oxo-1H,5H-benzo[ij]quinolizine-2-carboxamido]-2-phenylacetamido}-3,3-dimethyl-7-oxo-4-thia-1-azabicyclo[3,2,0]heptane-2-carboxylic acid as white amorphous crystals having a melting point of 182° to 187° C. (decomposed).

REFERENCE EXAMPLE 19

6-Chloroquinaldine (11 g) was dissolved in 15 ml of concentrated sulfuric acid and the solution was ice-cooled. Then, a solution of 7.1 g of potassium nitrate dissolved in 20 ml of concentrated sulfuric acid was added to the solution dropwise, during which operation the reaction temperature was maintained at 10° C. or less. After completion of addition the mixture was agitated at the same temperature as above for 1 hour and then poured onto 200 g of ice. Subsequently, the mixture was rendered alkaline with 10% sodium hydroxide, taking care that the internal temperature should not be raised to above 20° C., thus forming a pale yellow precipitate. The precipitate was collected by filtration, washed with water and recrystallized from ethanol to obtain 12.3 g of 5-nitro-6-chloroquinaldine as pale yellow rhombic crystals having a melting point of 123° to 124° C.

REFERENCE EXAMPLE 20

To 50 ml of concentrated hydrochloric acid having dissolved therein 25 g of stannous chloride was added 6.7 g of 5-nitro-6-chloroquinaldine and the mixture was allowed to react on a water bath at a temperature of 80° to 90° C. for 30 minutes. The reaction mixture was ice-cooled, rendered alkaline (pH 10) with 30% sodium hydroxide and filtered and extracted with 500 ml of chloroform and Celite (diatomaceous earth). After drying over anhydrous sodium sulfate the chloroform fraction was concentrated and recrystallized from a mixture of benzene and hexane to obtain 4.5 g of 5-amino-6-chloroquinaldine as colorless plates having a melting point of 196° to 197° C.

REFERENCE EXAMPLE 21

5-Amino-6-chloroquinaldine (4 g) was dissolved in 40 ml of concentrated hydrochloric acid and the resulting solution was cooled with ice. Then, a solution of 2.1 g of sodium nitrite dissolved in 5 ml of water was added thereto dropwise while ice-cooling. After continuing the reaction at the same temperature as above, the reaction mixture was added to a solution of 7 g of cuprous chloride dissolved in 15 ml of concentrated hydrochloric acid and the resulting mixture was allowed to react on a water bath at a temperature of 50° C. for 1 hour, during which time vigorous formation of nitrogen gas was observed. Subsequently, the reaction mixture was cooled, rendered alkaline with 30% sodium hydroxide, and filtered and extracted using 300 ml of chloroform and Celite (diatomaceous earth). After drying over anhydrous sodium sulfate the chloroform fraction was concentrated and recrystallized from a mixture of isopropanol and water to give 3.5 g of 5,6-dichloroquinaldine as white needles having a melting point of 84° to 85° C.

REFERENCE EXAMPLE 22

5,6-Dichloroquinaldine (5.5 g) was dissolved in 50 ml of acetic acid and 0.1 g of 5% platinum-carbon was added to the solution, which was then subjected to Parr's hydrogenation method to reduce the compound catalytically at a hydrogen gas pressure of 4 kg/cm². After theoretical amount of hydrogen was absorbed the reaction mixture was filtered and the filtrate was concentrated under reduced pressure. After rendering it alkaline with 50 ml of water and 20% sodium hydroxide, the residue was extracted with 100 ml of chloroform. The extract was dried by the addition of anhydrous potassium carbonate and concentrated to give 4.4 g of 5,6-dichloro-1,2,3,4-tetrahydroquinaldine as oily product.

NMR Analysis Data (in CDCl₃) $\sigma$: 1.23 (d, 3H, J=6 Hz), 1.7 (m, 2H), 2.72 (m, 2H), 3.28 (m, 1H), 3.75 (m, 1H), 6.62 (q, 2H, J=9 Hz).

REFERENCE EXAMPLE 23

A mixture of 3.2 g of 5,6-dichloro-1,2,3,4-tetrahydroquinaldine and 3.2 g of diethyl ethoxymethylenemalonate was allowed to react by heating at 160° C. for 30 minutes. Then 13 g of polyphosphoric acid prepared from 6.5 g of phosphorus pentoxide and 6.5 g of phosphoric acid was added to the mixture and the resulting mixture was allowed to react by heating at 140° to 150° C. for 1 hour. After completion of the reaction, the mixture was poured onto 100 g of ice, followed by rendering the mixture to pH 4 to 5 with a 40% aqueous sodium hydroxide solution to precipitate crystals. The crystals were collected by filtration, dried and mixed with 50 ml of a 10% aqueous sodium hydroxide solution. The mixture was allowed to react at 100° to 110° C. for 1 hour. After cooling, the reaction mixture was rendered acidic with concentrated hydrochloric acid to precipitate crystals. Recrystallization of the crystals thus-obtained from ethanol gave 2.3 g of 8,9-dichloro-5-methyl-6,7-dihydro-1-oxo-1H,5H-benzo[ij]quinolizine-2-carboxylic acid having a melting point of 269° to 271° C.

REFERENCE EXAMPLE 24

In an analogous manner as in Reference Example 21 was obtained 6-fluoro-5-chloro-1,2,3,4-tetrahydroquinaldine having the following physical property. NMR Spectral Analysis Data
$\sigma_{ppm}^{CDCl_3} = 1.88$ (d, 3H, J=6 Hz).

REFERENCE EXAMPLE 25

In an analogous manner as in Reference Example 22 was obtained 6-fluoro-5-amino-1,2,3,4-tetrahydro-quinaldine as an oily product. Production of this compound was confirmed by NMR spectral analysis and mass spectral analysis.

REFERENCE EXAMPLE 26

A mixture of 8 g of 6-fluoro-5-acetylamino-quinaldine and 0.2 g of 5% platinum on carbon was dissolved in 80 ml of acetic acid and the solution was subjected to catalytic hydrogenation according to Parr method at a hydrogen pressure of 4 kg/cm². After a theoretical amount of hydrogen was absorbed the reaction mixture was filtered. The filtrate was then concentrated under reduced pressure to obtain 8 g of 6-fluoro-5-acetylamino-1,2,3,4-tetrahydroquinaldine as an oily product. Production of this compound was confirmed by NMR spectral analysis and mass spectral analysis.

REFERENCE EXAMPLE 27

6-Fluoro-5-acetylamino-1,2,3,4-tetrahydroquinaldine (8 g) was dissolved in a mixture of 35 ml of concentrated hydrochloric acid and 20 ml of water. After refluxing the solution for 1 hour 10 ml of an aqueous solution having dissolved therein 5 g of sodium nitrite was added dropwise to the solution under ice-cooling taking care that the reaction temperature should not exceed 5° C. After completion of the addition the reaction mixture was stirred at the same temperature as above for 1 hour and poured into a solution of 12 ml of concentrated hydrochloric acid and 10 g of cuprous hydrochloride. The mixture was allowed to react at 80° C. for 1 hour and ice-cooled. After rendering it alkaline with an aqueous 28% ammonia solution the reaction mixture was extracted with 300 ml chloroform and Celite (diatomaceous earth, produced by Johns Manville Sales Corp.). The chloroform fraction obtained was dried over anhydrous sodium sulfate and concentrated. The residue was purified through a silica gel column chromatography (silica gel: Wako C-200, a trade name for a product of Wako Junyaku Co., Ltd.; eluent: chloroform-ethanol (9:1 by volume) to obtain 3.2 g of 6-fluoro-5-chloro-1,2,3,4-tetrahydroquinaldine as light orange oily product. Production of this compound was confirmed by NMR spectral analysis and mass spectral analysis.

NMR Spectral Analysis Data $\sigma_{ppm}^{CCl_4} = 1.88$ (d, 3H, J=6 Hz), 1.72 (m, 2H), 2.68 (m, 3H), 3.19 (m, 1H), 3.43 (s, 1H), 6.37 (m, 2H).

REFERENCE EXAMPLE 28

A mixture of 1.5 g of 6-fluoro-5-chloro-1,2,3,4-tetrahydroquinaldine and 1.8 g of diethyl ethoxymethylenemalonate was heated at 160° C. for 30 minutes. Then, 14 g of polyphosphoric acid prepared from 7 g of phosphorus pentoxide and 7 g of phosphoric acid was added to the mixture and the resulting mixture was allowed to react by heating at 140° to 150° C. for 1 hour. After completion of the reaction, the reaction mixture was poured onto 100 g of ice, followed by adjusting the mixture to pH 6 to 7 with a 10 N aqueous sodium hydroxide solution. The precipitates were collected by filtration and added to 30 ml of concentrated hydrochloric acid followed by heating under reflux. After completion of the reaction 50 ml of water was added to the reaction mixture to precipitate crystals. The crystals thus-obtained were collected by filtration, washed with water and dried. Recrystallization of the crude crystals from ethanol gave 1.2 g of 9-fluoro-8-chloro-5-methyl-6,7-dihydro-1-oxo-1H,5H-benzo[ij]quinolizine-2-carboxylic acid as white rhombic crystals having a melting point of 297° to 298° C.

EXAMPLE 1

19.2 g of 8-chloro-6,7-dihydro-1-oxo-1H,5H-benzo[ij]quinolizine-2-carboxylic acid and 35.5 g of piperazine were added to 350 ml of anhydrous dimethyl sulfoxide and the mixture was heated to an oil bath at 170° to 180° C. for 6 hours while stirring. After completion of the reaction, the solvent was removed under reduced pressure. 500 ml of water was added to the residue and the pH value of the mixture was adjusted to a pH of 2 followed by filtering water-insoluble materials. The filtrate was concentrated to 100 ml under reduced pressure and rendered alkaline (pH=9) with a 10% aqueous sodium hydroxide solution. After extracting the aqueous alkali solution with chloroform to thereby remove chloroform-soluble materials, the aqueous alkali solution layer was allowed to stand to precipitate crystals which were filtered. The crude crystals thus obtained were dissolved in 10 ml of a 10% aqueous sodium hydroxide solution and the solution was treated with activated carbon and adjusted to a pH of 8 with a 10% aqueous hydrochloric acid solution to precipitate crystals which were filtered and washed with water sufficiently. Recrystallization of the crystals from dimethylformamide gave 6.5 g of 8-(1-piperazinyl)-6,7-dihydro-1-oxo-1H,5H-benzo[ij]-quinolizine-2-carboxylic acid as white needles having a melting point of 267° to 268° C.

| Elemental Analysis for $C_{17}H_{19}O_3N_3.4H_2O$ | | | |
|---|---|---|---|
| | C | H | N |
| Calcd. (%): | 52.94 | 7.00 | 10.90 |
| Found (%): | 52.91 | 6.78 | 10.73 |

6.4 g of 8-(1-piperazinyl)-6,7-dihydro-1-oxo-1H,5H-benzo[ij]quinolizine-2-carboxylic acid thus-obtained was suspended in 50 ml of water and 15 ml of a 10% aqueous hydrochloric acid solution was added to the resulting solution. After removing the insoluble materials by filtration water was distilled off to obtain 5.7 g of 8-(1-piperazinyl)-6,7-dihydro-1-oxo-1H,5H-benzo[ij]-quinolizine-2-carboxylic acid hydrochloride as white amorphous crystals having a melting point of 300° C. or more.

| Elemental Analysis for $C_{17}H_{19}O_3N_3.HCl.H_2O$ | | | |
|---|---|---|---|
| | C | H | N |
| Calcd. (%): | 55.51 | 6.02 | 11.42 |
| Found (%): | 55.43 | 6.00 | 10.57 |

EXAMPLE 2

19.5 g of 8-chloro-5-methyl-6,7-dihydro-1-oxo-1H,5H-benzo[ij]quinolizine-2-carboxylic acid and 35.5 g of piperazine were added to 350 ml of anhydrous dimethyl sulfoxide and the mixture was heated on an oil bath at 170° to 180° C. for 6 hours while stirring. Treatment of the reaction mixture in an analogous manner as in Example 1 gave 5.3 g of 8-(1-piperazinyl)-5-methyl-6,7-dihydro-1-oxo-1H,5H-benzo[ij]quinolizine-2-carboxylic acid hydrochloride as white amorphous crystals having a melting point of 300° C. or more.

| Elemental Analysis for $C_{18}H_{21}O_3N_3.HCl.H_2O$ | | | |
|---|---|---|---|
| | C | H | N |
| Calcd. (%): | 56.62 | 6.33 | 11.00 |
| Found (%): | 56.71 | 6.33 | 11.00 |

3.8 g of 8-(1-piperazinyl)-5-methyl-6,7-dihydro-1-oxo-1H,5H-benzo[ij]quinolizine-2-carboxylic acid hydrochloride was added to 100 ml of water and 1 N aqueous sodium hydroxide solution was added thereto followed by heating the mixture to form a uniform solution. The solution was rendered alkaline (pH=8) with dilute hydrochloric acid to obtain 3.1 g of 8-(1-piperazinyl)-5-methyl-6,7-dihydro-1H,5H-benzo[ij]-quinolizine-2-carboxylic acid as colorless needles having a melting point of 264° to 265° C.

| Elemental Analysis for $C_{18}H_{21}O_3N_3$ | | | |
|---|---|---|---|
| | C | H | N |
| Calcd. (%): | 66.03 | 6.47 | 12.84 |
| Found (%): | 65.90 | 6.41 | 12.89 |

EXAMPLE 3

In an analogous manner as in Example 2 was prepared 8-(1-piperazinyl)-9-fluoro-5-methyl-6,7-dihydro-1-oxo-1H,5H-benzo[ij]quinolizine-2-carboxylic acid as white rhombic crystals having a melting point of 260° to 261° C.

EXAMPLE 4

4.0 g of 8-chloro-6,7-dihydro-1-oxo-1H,5H-benzo-[ij]quinolizine-2-carboxylic acid and 4.6 g of N-methyl-piperazine was added to 10 ml of anhydrous dimethylsulfoxide and the mixture was heated on an oil bath at 150° to 160° C. for 8 hours while stirring. After completion of the reaction, the solvent and excessive methylpiperazine were removed under reduced pressure and a mixture of methanol and diethyl ether was added to form precipitates which were separated by filtration and washed with diethyl ether. The crystals thus obtained were suspended in 20 ml of a 10% aqueous hydrochloric acid solution and insoluble materials were removed by filtration. The filtrate was purified through column chromatography using Amberlite LH-20 (a trade name for a product of Tokyo Organic Chemical Industries Ltd.) (eluent: water, ethanol). Recrystallization of the eluate from dimethylformamide gave 1.0 g of 8-(4-methyl-1-piperazinyl)-6,7-dihydro-1-oxo-1H,5H-benzo-[ij]quinolizine-2-carboxylic acid light yellow plates having a melting point of 278° to 280.5° C.

| Elemental Analysis for $C_{18}H_{21}O_3N_3$ | | | |
|---|---|---|---|
| | C | H | N |
| Calcd. (%): | 66.03 | 6.47 | 12.84 |
| Found (%): | 66.03 | 6.42 | 12.85 |

EXAMPLE 5

4.4 g of 8,10-dichloro-6,7-dihydro-1-oxo-1H,5H-benzo[ij]quinolizine-2-carboxylic acid and 4.5 g of piperazine were added to 10 ml of anhydrous dimethyl sulfoxide and the mixture was heated on an oil bath at 160° to 170° C. for 7 hours while stirring. Treatment of the reaction mixture in an analogous manner as in Example 4 gave 0.9 g of 8-(1-piperazinyl)-10-chloro-6,7-dihydro-1-oxo-1H,5H-benzo[ij]quinolizine-2-carboxylic acid hydrochloride as white amorphous crystals having a melting point of 300° C. or more.

| Elemental Analysis for $C_{17}H_{18}O_3N_3Cl \cdot HCl \cdot H_2O$ | | | |
|---|---|---|---|
| | C | H | N |
| Calcd. (%): | 50.76 | 5.26 | 10.45 |
| Found (%): | 50.68 | 5.24 | 10.53 |

EXAMPLES 6–14

In an analogous manner as described in Examples 1 to 5, the following compounds having various substituents shown in Table 5 were prepared. The melting point and the crystal form of the resulting products are also shown in Table 5 below.

TABLE 5

| Example No. | R² | R³ | Color and Form of Crystal | HA | Melting Point (°C.) |
|---|---|---|---|---|---|
| 6 | HC(O)— | H | White Needle | — | Above 300 |
| 7 | CH₃C(O)— | H | White Needle | — | 285–287 |
| 8 | C₆H₅C(O)— | H | White Needle | — | Above 300 |
| 9 | CH₃SO₂— | H | White Needle | — | Above 300 |
| 10 | (4-hydroxy-1,5-naphthyridin-3-yl)CO— | H | Brown Needle | — | Above 300 |
| 11 | C₆H₅CH₂— | H | Light Yellow Scale | — | 274–278 |
| 12 | CH₃—C₆H₄—SO₂— | H | White Needle | — | Above 300 |
| 13 | H | Cl (9-position) | White Amorphous | HCl | Above 300 |
| 14 | CH₃ | Cl (10-position) | White Amorphous | HCl | 297 (decomposed) |

Elemental Analyses of the compounds prepared in accordance with Examples 6 to 14 are shown in Table 6 below.

TABLE 6

| Example No. | Molecular Formulae | Elemental Analysis | | | | | |
|---|---|---|---|---|---|---|---|
| | | Calculated | | | Found | | |
| | | C | H | N | C | H | N |
| 6 | $C_{18}H_{19}O_4N_3$ | 63.33 | 5.61 | 12.31 | 63.27 | 5.49 | 12.18 |
| 7 | $C_{19}H_{21}O_4N_3$ | 64.21 | 5.96 | 11.83 | 64.13 | 5.95 | 11.81 |

TABLE 6-continued

| Example No. | Molecular Formulae | Elemental Analysis Calculated | | | Found | | |
|---|---|---|---|---|---|---|---|
| | | C | H | N | C | H | N |
| 8 | $C_{24}H_{23}O_4N_3$ | 69.05 | 5.55 | 10.07 | 68.88 | 5.43 | 10.01 |
| 9 | $C_{18}H_{21}O_5N_3S$ | 55.24 | 5.41 | 10.74 | 55.07 | 5.39 | 10.62 |
| 10 | $C_{26}H_{23}O_5N_5$ | 64.32 | 4.78 | 14.43 | 64.09 | 4.61 | 14.27 |
| 11 | $C_{24}H_{25}O_3N_3$ | 71.44 | 6.25 | 10.42 | 71.23 | 6.15 | 10.31 |
| 12 | $C_{24}H_{25}O_5N_3S$ | 61.66 | 5.39 | 8.99 | 61.58 | 5.35 | 8.81 |
| 13 | $C_{17}H_{18}O_3N_3Cl.HCl.H_2O$ | 50.76 | 5.26 | 10.45 | 50.70 | 5.23 | 10.33 |
| 14 | $C_{18}H_{20}O_3N_3Cl.HCl.H_2O$ | 51.93 | 5.57 | 10.09 | 51.71 | 5.42 | 9.86 |

EXAMPLE 15

19.1 g of 8-(p-toluenesulfonyl)-6,7-dihydro-1-oxo-1H,5H-benzo[ij]quinolizine-2-carboxylic acid and 12.9 g of piperazine were added to 200 ml of anhydrous dimethyl sulfoxide and the mixture was heated in an autoclave under flow of nitrogen at 10 atm. at a temperature of 150° to 160° C. for 18 hours while stirring. After completion of the reaction, the solvent and excess piperazine were removed under reduced pressure and a mixture of methanol and ethanol was added to the residue. The preicpitates formed were separated by filtration and washed with diethyl ether. The crystals thus-obtained were suspended in a mixture of 200 ml of water and 40 ml of a 10% aqueous hydrochloric acid solution and insoluble materials were removed by filtration. The filtrate was rendered neutral with saturated aqueous solution of sodium bicarbonate and purified through column chromatography using Amberlite LH-20 (a trade name for a product of Tokyo Organic Chemical Industries Ltd.) (eluent: water, ethanol). Recrystallization of the eluate from dimethylformamide gave 2.7 g of 8-(1-piperazinyl)-6,7-dihydro-1-oxo-1H,5H-benzo[ij]-quinolizine-2-carboxylic acid as white needles having a melting point of 267° to 268° C.

EXAMPLE 16

20.0 g of 8-(p-nitrobenzenesulfonyloxy)-6,7-dihydro-1-oxo-1H,5H-benzo[ij]quinolizine-2-carboxylic acid and 12.9 g of piperazine were added to 200 ml of anhydrous dimethyl sulfoxide and the mixture was heated in an autoclave under flow of nitrogen at 10 atm. at a temperature of 150° to 160° C. for 17 hours while stirring. Treatment in an analogous manner as in Example 15 gave 2.1 g of 8-(1-piperazinyl)-6,7-dihydro-1-oxo-1H,5H-benzo[ij]quinolizine-2-carboxylic acid as white needles having a melting point of 267° to 268° C.

EXAMPLE 17

15.4 g of 8-methanesulfonyloxy-5-methyl-6,7-dihydro-1-oxo-1H,5H-benzo[ij]quinolizine-2-carboxylic acid and piperazine 12.9 g were added to 200 ml of anhydrous dimethyl sulfoxide and the mixture was heated in an autoclave under flow of nitrogen at 8 atm. at a temperature of 170° to 180° C. for 20 hours while stirring. Treatment in an analogous manner as in Example 15 gave 1.7 g of 8-(1-piperazinyl)-5-methyl-6,7-dihydro-1-oxo-1H,5H-benzo[ij]quinolizine-2-carboxylic acid hydrochloride as white amorphous crystals having a melting point of not lower than 300° C.

EXAMPLE 18

18.5 g of 8-benzenesulfonyloxy-6,7-dihydro-1-oxo-1H,5H-benzo[ij]quinolizine-2-carboxylic acid and 12.9 g of piperazine were added to 200 ml of anhydrous dimethyl sulfoxide and the mixture was heated in an autoclave under flow of nitrogen at 10 atm. at a temperature of 160° to 170° C. for 20 hours while stirring. Treatment in the same manner as in Example 15 gave 1.5 g of 8-(1-piperazinyl)-6,7-dihydro-1-oxo-1H,5H-benzo[ij]quinolizine-2-carboxylic acid as white needles having a melting point of 267° to 268° C.

EXAMPLE 19

20.7 g of 8-(o-methoxybenzenesulfonyloxy)-5-methyl-6,7-dihydro-1-oxo-1H,5H-benzo[ij]quinolizine-2-carboxylic acid and 12.9 g of piperazine were added to 200 ml of anhydrous dimethyl sulfoxide and the mixture was heated in autoclave under flow of nitrogen at 10 atm. at a temperature of 150° to 160° C. for 18 hours while stirring. Treatment in an analogous manner as in Example 17 gave 2.5 g of 8-(1-piperazinyl)-5-methyl-6,7-dihydro-1-oxo-1H,5H-benzo[ij]quinolizine-2-carboxylic acid as white amorphous crystals having a melting point of not lower than 300° C.

EXAMPLES 20-26

In an analogous manner as described in Examples 15 to 19 the following compounds having various substituents shown in Table 7 below were prepared. The melting point and the crystal form of the resulting products are also shown in Table 7.

TABLE 7

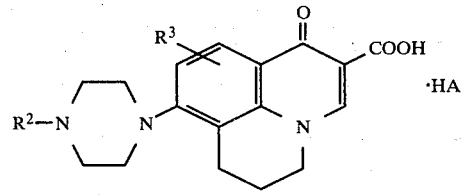

| Example No. | $R^2$ | $R^3$ | Color and Form of Crystal | HA | Melting Point (°C.) |
|---|---|---|---|---|---|
| 20 | $CH_3$ | H | Light Yellow | — | 278–280.5 |

TABLE 7-continued

[Structure: quinolizine with R³ at 9-position, R²-N-piperazinyl substituent, COOH group, ·HA]

| Example No. | R² | R³ | Color and Form of Crystal | HA | Melting Point (°C.) |
|---|---|---|---|---|---|
| 21 | H | Cl (9-position) | Plate White Amorphous | HCl | Above 300 |
| 22 | CH₃C(O)— | H | White Needle | — | 285–287 |
| 23 | C₆H₅—CH₂— | H | Light Brown Scale | — | 274–278 |
| 24 | CH₃—C₆H₄—SO₂— | H | White Needle | — | Above 300 |
| 25 | CH₃SO₂— | H | White Needle | — | Above 300 |
| 26 | CH₃— | Cl (10-position) | White Amorphous | HCl | 297 (decomposed) |

EXAMPLE 27

2.0 g of 8-(1-piperazinyl)-6,7-dihydro-1-oxo-1H,5H-benzo[ij]quinolizine-2-carboxylic acid and 1.2 g of sodium hydrogen carbonate were added to 30 ml of water and the mixture was stirred at room temperature for 30 minutes. 5 ml of acetone having dissolved therein 1.0 g of benzoyl chloride was added dropwise to the mixture while ice-cooling followed by stirring at the same temperature as above for 30 minutes and then at room temperature for 1.5 hours to precipitate crystals, which were separated by filtration and washed with water. Recrystallization of the crystals thus-treated from dimethylformamide gave 2.4 g of 8-(4-benzoyl-1-piperazinyl)-6,7-dihydro-1-oxo-1H,5H-benzo[ij]quinolizine-2-carboxylic acid as white needles having a melting point of not lower than 300° C.

EXAMPLE 28

2.0 g of 8-(1-piperazinyl)-6,7-dihydro-1-oxo-1H,5H-benzo[ij]quinolizine-2-carboxylic acid was dissolved in 20 ml of water having dissolved therein 0.8 g of potassium hydroxide and 0.8 g of methanesulfonyl chloride was added dropwise to the solution. The resulting mixture was allowed to stand overnight at the same temperature as above while stirring. The crystals precipitated were separated by filtration and washed with water. The crystals thus-treated were dissolved in 1 N aqueous sodium hydroxide solution and the solution was treated with activated carbon and rendered neutral with a 10% aqueous hydrochloric acid solution to precipitate crystals, which were separated by filtration and washed with water. Recrystallization of the crystals thus-obtained from dimethylformamide gave 1.0 g of 8-(4-methanesulfonyl-1-piperazinyl)-6,7-dihydro-1-oxo-1H,5H-benzo[ij]quinolizine-2-carboxylic acid as white needles having a melting point of not lower than 300° C.

EXAMPLE 29

2.0 g of 8-(1-piperazinyl)-6,7-dihydro-1-oxo-1H,5H-benzo[ij]quinolizine-2-carboxylic acid was added to 20 ml of water having dissolved therein 2.0 g of potassium carbonate and the mixture was stirred at room temperature for 30 minutes. After dissolving insoluble materials completely with the addition of 3 ml of 1 N aqueous sodium hydroxide solution, 10 ml of methanol having dissolved therein 0.9 g of benzyl chloride was added dropwise to the mixture while ice-cooling. After completion of the addition, the resulitng mixture was heat-refluxed for 3 hours to form a uniform solution. The solution obtained was treated with activated carbon while hot and rendered neutral with a 10% aqueous hydrochloric acid to precipitate crystals, which were separated by filtration and washed with water. Recrystallization of the crystals thus treated from dimethylformamide gave 0.25 g of 8-(4-benzyl-1-piperazinyl)-6,7-dihydro-1-oxo-1H,5H-benzo[ij]-quinolizine-2-carboxylic acid having a melting point of 274° to 278° C.

EXAMPLE 30

20 ml of dimethyl sulfoxide was added to a mixture of 3 g of 9-chloro-6-oxo-1,2-dihydro-6H-pyrrolo-[3,2,1-ij]quinoline-5-carboxylic acid and 6 g of anhydrous piperazine and the mixture was heated on an oil bath at 140° to 150° C. for 6 hours. After completion of reaction the solvent was removed therefrom under reduced pressure and 50 ml of water was added to the residue to dissolve it. The solution was shaken with 100 ml of chloroform and the water layer was separated and treated with activated carbon. The aqueous solution was rendered acidic with a 10% aqueous hydrochloric acid and filtered. The filtrate was again treated with activated carbon followed by concentration. The addition of ethanol to the concentrate gave rise to crystals which were recrystallized from ethanol-water to obtain 1.5 g of 9-(1-piperazinyl)-6-oxo-1,2-dihydro-6H-pyrrolo[3,2,1-ij]-quinoline-5-carboxylic acid hydrochloride as light yellow needles having a melting point of 300° C. or more.

| Elemental Analysis for $C_{16}H_{17}O_3N_3$ HCl.4H$_2$O | | | |
|---|---|---|---|
| | C | H | N |
| Calcd. (%): | 47.12 | 6.38 | 10.31 |
| Found (%): | 47.23 | 6.09 | 10.10 |

EXAMPLE 31

20 ml of dimethyl sulfoxide was added to a mixture of 1.6 g of 9-chloro-2-methyl-6-oxo-1,2-dihydro-6H-pyrrolo[3,2,1-ij]quinoline-5-carboxylic acid and 3 g of anhydrous piperazine and the mixture was heated on an oil bath at 140° to 150° C. for 6 hours. After completion of reaction the solvent was removed therefrom under reduced pressure and 50 ml of water was added to the residue to dissolve it. The solution was shaken with 100 ml of chloroform and the water layer was separated and treated with activated carbon. The aqueous solution was rendered acidic with a 10% aqueous hydrochloric acid solution and filtered. The filtrate was again treated with activated carbon followed by concentration. The addition of ethanol to the concentrate gave rise to crystals which were recrystallized from ethanol-water to obtain 0.9 g of 9-(1-piperazinyl)-2-methyl-6-oxo-1,2-dihydro-6H-pyrrolo[3,2,1-ij]quinoline-5-carboxylic acid hydrochloride as light yellow needles having a melting point of 269° to 273° C. (decomposed).

| Elemental Analysis for $C_{17}H_{19}O_3N_3$.HCl.H$_2$O | | | |
|---|---|---|---|
| | C | H | N |
| Calcd. (%): | 55.51 | 6.02 | 11.42 |
| Found (%): | 55.47 | 5.98 | 11.29 |

EXAMPLE 32

3.1 g of 1-chloro-7a,8,9,10,11,11a-hexahydro-4H-pyrido[3,2,1-jk]carbazole-4-oxo-5-carboxylic acid was mixed with 5 g of anhydrous piperazine and 50 ml of dimethyl sulfoxide and the mixture was heated at 140° to 150° C. on an oil bath for 4 hours with stirring. After completion of the reaction the solvent was removed under reduced pressure. 200 ml of water and 200 ml of chloroform were added to the residue and after shaking the water layer was separated. After adjusting the pH value thereof to a pH of 3 the water layer was filtered. The filtrate was treated with activated carbon and concentrated to obtain light yellow precipitates. The precipitates were washed with a small amount of water and dried to give 1.3 g of 1-(1-piperazinyl)-7a,8,9,10,11,11a-hexahydro-4H-pyrido[3,2,1-jk]carbazole-4-oxo-5-carboxylate acid hydrochloride having a melting point of 289° to 294° C. (decomposed).

| Elemental Analysis for $C_{20}H_{23}N_3O_3$.HCl.3H$_2$O | | | |
|---|---|---|---|
| | C | H | N |
| Calcd. (%): | 54.12 | 6.76 | 9.47 |
| Found (%): | 53.77 | 6.95 | 9.18 |

EXAMPLE 33

In an analogous manner as in Example 1, 8,9-dichloro-5-methyl-6,7-dihydro-1-oxo-1H,5H-benzo[ij]-quinolizine-2-carboxylic acid was reacted with piperazine, 1-methylpiperazine, 1-ethylpiperazine or 4-formylpiperazine to form the following compounds:

8-(1-Piperazinyl)-9-chloro-5-methyl-6,7-dihydro-1-oxo-1H,5H-benzo[ij]quinolizine-2-carboxylic acid as white rhombic crystals having a melting point of 246° to 247° C.

8-(1-Piperazinyl)-9-chloro-5-methyl-6,7-dihydro-1-oxo-1H,5H-benzo[ij]quinolizine-2-carboxylic acid monohydrochloride monohydrate as white amorphous crystals having a melting point of 306° to 307° C. (decomposed after blackening).

8-(4-Methyl-1-piperazinyl)-9-chloro-5-methyl-6,7-dihydro-1-oxo-1H,5H-benzo[ij]quinolizine-2-carboxylic acid as white rhombic crystals having a melting point of 292° to 293° C.

8-(4-Ethyl-1-piperazinyl)-9-chloro-5-methyl-6,7-dihydro-1-oxo-1H,5H-benzo[ij]quinolizine-2-carboxylic acid monohydroiodide monohydrate as white rhombic crystals having a melting point of 271° to 272° C.

8-(4-Formyl-1-piperazinyl)-9-chloro-5-methyl-6,7-dihydro-1-oxo-1H,5H-benzo[ij]quinolizine-2-carboxylic acid as white rhombic crystals having a melting point of 262° to 265° C.

EXAMPLE 34

In an analogous manner as in Example 1, 8-chloro-5-methyl-6,7-dihydro-1-oxo-1H,5H-benzo[ij]-quinolizine-2-carboxylic acid was reacted with 1-formylpiperazine to form 8-(4-formyl-1-piperazinyl)-5-methyl-6,7-dihydro-1-oxo-1H,5H-benzo[ij]quinolizine-2-carboxylic acid as white rhombic crystals having a melting point of 300° C. or more.

EXAMPLE 35

A mixture of 1.8 g of 9-fluoro-8-chloro-5-methyl-6,7-dihydro-1-oxo-1H,5H-benzo[ij]quinolizine-2-carboxylic acid, 36 ml of N-methylpiperazine and 15 ml of hexamethylphosphoric triamide was heated at 150° to 160° C. for 4 hours. After completion of the reaction the solvent was removed by distillation under reduced pressure and the residue was washed with 10 ml of ethyl acetate. The crude crystals thus-obtained were mixed with 100 ml of water and adjusted to a pH of 4 with acetic acid. Insoluble materials were removed by filtration and the filtrate was treated with activated carbon followed by concentration under reduced pressure. The residue was mixed with 20 ml of water and the solution was adjusted to a pH of 9 with a 10% aqueous sodium hydroxide solution and extracted with 80 ml chloroform. After the extract was dried over anhydrous sodium sulfate and concentrated it was purified through a silica gel column chromatography (silica gel: Wako C-200, a trade name for a product of Wako Junyaku Co., Ltd.; eluent: chloroform-methanol (9:1 by volume)) to obtain 0.8 g of 8-(4-methyl-1-piperazinyl)-9-fluoro-5-methyl-6,7-dihydro-1- oxo-1H,5H-benzo[ij]quinolizine-2-carboxylic acid as white rhombic crystals having a melting point of 262° to 263° C.

EXAMPLE 36

A mixture of 3 g of 9-fluoro-8-bromo-5-methyl-6,7-dihydro-1-oxo-1H,5H-benzo[ij]quinolizine-2-carboxylic acid, 3.8 g of anhydrous piperazine and 30 ml of hexamethylphosphoric triamide was heated at 150° to 160° C. on a water bath for 5 hours in an argon stream. After completion of the reaction the solvent was removed under reduced pressure and 20 ml of ethyl acetate was added to the residue. The crystals precipitated were collected by filtration. The crystals thus-obtained were dissolved in 300 ml of water and the solution was adjusted to a pH of 4 with acetic acid. After adding activated carbon to the solution and filtering, the filtrate was concentrated under reduced pressure. Recrystallization of the crude crystals precipitated from isopropanol-water (2:1 by volume) gave 2.7 g of 8-(1-piperazinyl)-9-fluoro-5-methyl-6,7-dihydro-1-oxo-benzo[ij]quinolizine-2-carboxylic acid hydrobromide as rhombic crystals having a melting point of 300° C. or more.

| Elemental Analysis Values for $C_{18}H_{20}N_3O_3F \cdot HBr \cdot H_2O$ | | | |
|---|---|---|---|
| | C | H | N |
| Calcd. (%): | 48.65 | 5.18 | 9.46 |
| Found (%): | 48.53 | 5.11 | 9.32 |

EXAMPLE 37

8-(4-Methyl-1-piperazinyl)-9-fluoro-5-methyl-6,7-dihydro-1-oxo-1H,5H-benzo[ij]quinolizine-2-carboxylic acid was added to 48% hydrobromic acid and the solvent was removed by distillation under reduced pressure. Recrystallization of the residue from isopropanol-water (2:1 by volume) gave 8-(4-methyl-1-piperazinyl)-9-fluoro-5-methyl-6,7-dihydro-1-oxo-1H,5H-benzo[ij]quinolizine-2-carboxylic acid hydrobromide monohydrate as white rhombic crystals having a melting point of 298° to 299° C. (decomposed).

EXAMPLE 38

In an analogous manner as in Example 30, 8,9-dichloro-2-methyl-6-oxo-1,2-dihydro-6H-pyrrolo[3,2,1-ij]-quinoline-5-carboxylic acid was reacted with piperazine, 1-methylpiperazine, 1-formylpiperazine or 1-acetyl-piperazine to form the following compounds.

8-Chloro-9-(1-piperazinyl)-2-methyl-6-oxo-1,2-dihydro-6H-pyrrolo[3,2,1-ij]quinoline-5-carboxylic acid as pale yellow rhombic crystals having a melting point of 258° to 260° C.

8-Chloro-9-(4-methyl-1-piperazinyl)-2-methyl-6-oxo-1,2-dihydro-6H-pyrrolo[3,2,1-ij]quinoline-5-carboxylic acid as pale yellow rhombic crystals having a melting point of 273° to 276° C.

8-Chloro-9-(4-methyl-1-piperazinyl)-2-methyl-6-oxo-1,2-dihydro-6H-pyrrolo[3,2,1-ij]quinoline-5-carboxylic acid.

8-Chloro-9-(4-acetyl-1-piperazinyl)-2-methyl-6-oxo-1,2-dihydro-6H-pyrrolo[3,2,1-ij]quinoline-5-carboxylic acid.

EXAMPLE 39

In an analogous manner as in Example 30, 8-fluoro-9-iodo-2-methyl-6-oxo-1,2-dihydro-6H-pyrrolo[3,2,1-ij]quinoline-5-carboxylic acid was reacted with piperazine, 1-methylpiperazine or 1-formylpiperazine to obtain the following compounds.

8-Fluoro-9-(1-piperazinyl)-2-methyl-6-oxo-1,2-dihydro-6H-pyrrolo[3,2,1-ij]quinoline-5-carboxylic acid hydroiodide as light yellow rhombic crystals having a melting point of above 300° C. (discolored at 270° C. but unmolten at 300° C.).

8-Fluoro-9-(4-methyl-1-piperazinyl)-2-methyl-6-oxo-1,2-dihydro-6H-pyrrolo[3,2,1-ij]quinoline-5-carboxylic acid as white rhombic crystals having a melting point of 242° to 244° C.

8-Fluoro-9-(4-formyl-1-piperazinyl)-2-methyl-6-oxo-1,2-dihydro-6H-pyrrolo[3,2,1-ij]quinoline-5-carboxylic acid.

EXAMPLE 40

In an analogous manner as in Example 1, 9-fluoro-8-bromo-5-methyl-6,7-dihydro-1-oxo-1H,5H-benzo[ij]quinolizine-2-carboxylic acid was reacted with 1-formylpiperazine, 1-acetylpiperazine, 1-propionylpiperazine or 1-ethylpiperazine to obtain the following compounds.

8-(4-Formyl-1-piperazinyl)-9-fluoro-5-methyl-6,7-dihydro-1-oxo-1H,5H-benzo[ij]quinolizine-2-carboxylic acid as white rhombic crystals having a melting point of 300° C. or more.

8-(4-Acetyl-1-piperazinyl)-9-fluoro-5-methyl-6,7-dihydro-1-oxo-1H,5H-benzo[ij]quinolizine-2-carboxylic acid as white rhombic crystals having a melting point of 247° to 249° C.

8-(4-Propionyl-1-piperazinyl)-9-fluoro-5-methyl-6,7-dihydro-1-oxo-1H,5H-benzo[ij]quinolizine-2-carboxylic acid as white rhombic crystals having a melting point of 272° to 274° C.

8-(4-Ethyl-1-piperazinyl)-9-fluoro-5-methyl-6,7-dihydro-1-oxo-1H,5H-benzo[ij]quinolizine-2-carboxylic acid as white rhombic crystals having a melting point of 253° to 255° C.

EXAMPLE 41

A mixture of 2.5 g of 8-(1-piperazinyl)-9-chloro-5-methyl-6,7-dihydro-1-oxo-1H,5H-benzo[ij]quinolizine-2-carboxylic acid and 50 ml of trifluoroacetic anhydride was heated under reflux for 3 hours. After completion of heating, excessive trifluoroacetic anhydride was distilled off under reduced pressure and 50 ml of water was added to the residue followed by stirring to precipitate white crystals. Recrystallization of the crystals from dimethylformamide gave 2.3 g of 8-(4-trifluoroacetyl-1-piperazinyl)-9-chloro-5-methyl-6,7-dihydro-1-oxo-1H,5H-benzo[ij]quinolizine-2-carboxylic acid as white rhombic crystals having a melting point of 300° C. or more.

| Elemental Analysis for $C_{20}H_{19}ClF_3N_3O_4$ (molecular weight: 457.5) | | | |
|---|---|---|---|
| | C | H | N |
| Calcd. (%): | 52.46 | 4.15 | 9.18 |
| Found (%): | 52.31 | 4.11 | 9.22 |

A mixture of 1 g of 8-(1-piperazinyl)-9-chloro-5-methyl-6,7-dihydro-1-oxo-1H,5H-benzo[ij]quinolizine-2-carboxylic acid, 15 ml of dimethylformamide, 1.2 ml of 2,2,2-trifluoroethyl iodide and 2 ml of triethylamine was heated at 80° C. for 5 hours. After cooling, insoluble substances were removed by filtration and the filtrate was concentrated under reduced pressure. The residue was mixed with 30 ml of water and insoluble substances were removed by filtration. After concentrating it under reduced pressure, the filtrate was purified through a silica gel column chromatography (silica gel: Wako C-200, a trade name for a product of Wako Junyaku Co., Ltd.; eluent: chloroform-methanol (9:1 by volume)) to obtain 0.5 g of 8-[4-(2,2,2-trifluoroethyl)-1-piperazinyl]-9-chloro-5-methyl-6,7-dihydro-1-oxo-1H,5H-benzo[ij]-quinolizine-2-carboxylic acid.iodide.monohydrate as white rhombic crystals having a melting point of 298° to 299° C.

EXAMPLE 43

A mixture of 0.8 g of 8-(1-piperazinyl)-9-chloro-5-methyl-6,7-dihydro-1-oxo-1H,5H-benzo[ij]-quinolizine 2-carboxylic acid hydrochloride hydrate, 0.4 ml of propargyl bromide, 0.8 ml of triethylamine and 10 ml of dimethylformamide was allowed to react by heating at 90° C. for 5 hours. After completion of the reaction insoluble substances were removed by filtration. After concentration under reduced pressure the filtrate was purified through a silica gel column chromatography (silica gel: Wako C-200, a trade name for a product of Wako Junyaku Co., Ltd.; eluent: chloroform-methanol (8:1 by volume)) to obtain 0.3 g of 8-[4-(2-propynyl)-1-piperazinyl]-9-chloro-5-methyl-6,7-dihydro-1-oxo-1H,5H-benzo[ij]quinolizine-2-carboxylic acid as pale yellow rhombic crystals having a melting point of 211° to 213° C.

EXAMPLE 44

A mixture of 1 g of 8-(1-piperazinyl)-9-chloro-5-methyl-6,7-dihydro-1-oxo-1H,5H-benzo[ij]quinolizine-2-carboxylic acid, 0.6 ml of triethylamine, 0.6 ml of trifluoroemethanesulfonyl chloride and 15 ml of dimethylformamide was stirred at room temperature for 3 hours. After completion of stirring, the solvent was removed under reduced pressure to concentrate the reaction mixture. By the addition of 30 ml of water to the concentrate pale yellow crystals precipitated. Recrystallization of the crystals from a mixture of dimethylformamide and water gave 0.7 g of 8-(4-trifluoromethanesulfonyl-1-piperazinyl)-9-chloro-5-methyl-6,7-dihydro-1-oxo-1H,5H-benzo[ij]quinolizine-2-carboxylic acid as pale yellow powder having a melting point of 232° to 235° C.

EXAMPLES 45–51

In an analogous manner as in Example 44, the following compounds were prepared.

EXAMPLE 45

8-(4-Allyl-1-piperazinyl)-9-chloro-5-methyl-6,7-dihydro-1-oxo-1H,5H-benzo[ij]quinolizine-2-carboxylic acid Melting point: 226° to 227° C.

EXAMPLE 46

8-[4-(2-Chloroethyl)-1-piperazinyl]-9-chloro-5-methyl-6,7-dihydro-1-oxo-1H,5H-benzo[ij]quinolizine-2-carboxylic acid Melting point: 284° to 285° C.

EXAMPLE 47

8-[4-(4-Methoxybenzyl)-1-piperazinyl]-9-chloro-5-methyl-6,7-dihydro-1-oxo-1H,5H-benzo[ij]quinolizine-2-carboxylic acid Melting point: 270° to 272° C.

EXAMPLE 48

8-[4-(2-Hydroxyethyl)-1-piperazinyl]-9-chloro-5-methyl-6,7-dihydro-1-oxo-1H,5H-benzo[ij]quinolizine-2-carboxylic acid Melting point: 228° to 230° C.

EXAMPLE 49

8-(4-Pentafluoropropionyl-1-piperazinyl)-9-chloro-5-methyl-6,7-dihydro-1-oxo-1H,5H-benzo[ij]quinolizine-2-carboxylic acid Melting point: 296° to 297° C.

EXAMPLE 50

8-(4-Heptafluorobutyryl-1-piperazinyl)-9-chloro-5-methyl-6,7-dihydro-1-oxo-1H,5H-benzo[ij]quinolizine-2-carboxylic acid Melting point: 269.5° to 270.5° C.

EXAMPLE 51

8-[4-(2-Hydroxyethyl)-1-piperazinyl]-9-fluoro-5-methyl-6,7-dihydro-1-oxo-1H,5H-benzo[ij]quinolizine-2-carboxylic acid Melting point: 288° to 290° C.

EXAMPLE 52

A mixture of 3.1 g of 8,9-dichloro-5-methyl-6,7-dihydro-1-oxo-1H,5H-benzo[ij]quinolizine-2-carboxylic acid, 9.1 g of 1-trifluoroacetylpiperazine and 50 ml of HMPTA was heated at 160° C. for 4 hours under atmosphere of argon. After completion of the reaction, the solvent was removed by distillation under reduced pressure and the residue was washed with water. Recrystallization of the residue from dimethylformamide gave 2.3 g of 8-(4-trifluoroacetyl-1-piperazinyl)-9-chloro-5-methyl-6,7-dihydro-1-oxo-1H,5H-benzo[ij]quinolizine-2-carboxylic acid as white rhombic crystals having a melting point of 300° C. or more.

EXAMPLE 53

A mixture of 1.6 g of 8,9-dichloro-6,7-dihydro-5-methyl-1-oxo-1H,5H-benzo[ij]quinolizine-2-carboxylic acid, 3.2 g of 1-propargylpiperazine and 25 ml of HMPTA was heated with stirring at 160° C. for 5 hours under atmosphere of argon. After completion of the reaction, the solvent was removed by distillation and the residue was washed with water. The residue was dissolved in 100 ml of water and insoluble substances were removed by filtration. The aqueous fraction was extracted with 200 ml of chloroform and the chloroform fraction was dried over anhydrous sodium sulfate. After concentration, the concentrate was purified through a silica gel column chromatography (silica gel: Wako C-200, a trade name for a product of Wako Junyako Co., Ltd.; eluent: chloroform-methanol (9:1 by volume)) to obtain 1.2 g of 8-[4-(2-propynyl)-1-piperazinyl]-9-chloro-5-methyl-6,7-dihydro-1-oxo-1H,5H-benzo[ij]quinolizine-2-carboxylic acid having a melting point of 211° to 213° C.

EXAMPLES 54–61

In an analogous manner as in Example 53 the following compounds were obtained.

EXAMPLE 54

8-(4-Allyl-1-piperazinyl)-9-chloro-5-methyl-6,7-dihydro-1-oxo-1H,5H-benzo[ij]quinolizine-2-carboxylic acid Melting point: 226° to 227° C.

EXAMPLE 55

8-[4-(4-Methoxybenzyl)-1-piperazinyl]-9-chloro-5-methyl-6,7-dihydro-1-oxo-1H,5H-benzo[ij]quinolizine-2-carboxylic acid Melting point: 270° to 272° C.

EXAMPLE 56

8-[4-(2-Hydroxyethyl)-1-piperazinyl]-9-chloro-5-methyl-6,7-dihydro-1-oxo-1H,5H-benzo[ij]quinolizine-2-carboxylic acid Melting point: 228° to 230° C.

EXAMPLE 57

8-[4-(2-Chloroethyl)-1-piperazinyl]-9-chloro-5-methyl-6,7-dihydro-1-oxo-1H,5H-benzo[ij]quinolizine-2-carboxylic acid Melting point: 284° to 285° C.

EXAMPLE 58

8-(4-Pentafluoropropionyl-1-piperazinyl)-9-chloro-5-methyl-6,7-dihydro-1-oxo-1H,5H-benzo[ij]quinolizine-2-carboxylic acid Melting point: 296° to 297° C.

EXAMPLE 59

8-(4-Heptafluorobutyryl-1-piperazinyl)-9-chloro-5-methyl-6,7-dihydro-1-oxo-1H,5H-benzo[ij]quinolizine-2-carboxylic acid Melting point: 269.5° to 270.5° C.

EXAMPLE 60

8-(4-Trifluoromethanesulfonyl-1-piperazinyl)-9-chloro-6,7-dihydro-1-oxo-1H,5H-benzo[ij]quinolizine-2-carboxylic acid Melting point: 232° to 235° C.

EXAMPLE 61

8-[4-(2-Hydroxyethyl)-1-piperazinyl]-9-fluoro-5-methyl-6,7-dihydro-1-oxo-1H,5H-benzo[ij]quinolizine-2-carboxylic acid Melting point: 288° to 290° C.

EXAMPLE 62

A mixture of 2.75 g of 8-(4-trifluoroacetyl-1-piperazinyl)-9-chloro-5-methyl-2-acetyl-6,7-dihydro-1-oxo-1H,5H-benzo[ij]quinolizine, 3 g of iodine and 20 ml of pyridine was heated at 100° C. for 1 hour. After completion of the reaction, crystals precipitated was collected by filtration and washed with 10 ml of cool pyridine and with 10 ml of methanol to obtain 8-(4-trifluoroacetyl-1-piperazinyl)-9-chloro-5-methyl-6,7-dihydro-1-oxo-1H,5H-benzo[ij]quinolizine-2-carbonylmethylpyridinium iodide. This compound was mixed with 50 ml of methanol and 50 ml of a 10% aqueous sodium hydroxide solution and the resulting mixture was refluxed for 1 hour. After completion of the reaction methanol was removed by distillation and the reaction mixture was adjusted to pH 7 with N hydrochloric acid to give 1.8 g of 8-(4-trifluoroacetyl-1-piperazinyl)-9-chloro-5-methyl-6,7-dihydro-1-oxo-1H,5H-benzo[ij]quinolizine-2-carboxylic acid as white rhombic crystals having a melting point of 300° C. or more.

EXAMPLES 63-72

In an analogous manner as in Example 62 the following compounds were prepared.

EXAMPLE 63

8-[4-(2,2,2-Trifluoroethyl)-1-piperazinyl]-9-chloro-5-methyl-6,7-dihydro-1-oxo-1H,5H-benzo[ij]quinolizine-2-carboxylic acid Melting point: 298° to 299° C.

EXAMPLE 64

8-[4-(2-Hydroxyethyl)-1-piperazinyl]-9-chloro-5-methyl-6,7-dihydro-1-oxo-1H,5H-benzo[ij]quinolizine-2-carboxylic acid Melting point: 228° to 230° C.

EXAMPLE 65

8-[4-(2-Chloroethyl)-1-piperazinyl]-9-chloro-5-methyl-6,7-dihydro-1-oxo-1H,5H-benzo[ij]quinolizine-2-carboxylic acid Melting point: 284° to 285° C.

EXAMPLE 66

8-(4-Allyl-1-piperazinyl)-9-chloro-5-methyl-6,7-dihydro-1-oxo-1H,5H-benzo[ij]quinolizine-2-carboxylic acid Melting point: 226° to 227° C.

EXAMPLE 67

8-[4-(4-Methoxybenzyl)-1-piperazinyl]-9-chloro-5-methyl-6,7-dihydro-1-oxo-1H,5H-benzo[ij]quinolizine-2-carboxylic acid Melting point: 270° to 272° C.

EXAMPLE 68

8-[4-(2-Propynyl)-1-piperazinyl]-9-chloro-5-methyl-6,7-dihydro-1-oxo-1H,5H-benzo[ij]quinolizine-2-carboxylic acid Melting point: 211° to 213° C.

EXAMPLE 69

8-(4-Pentafluoropropionyl-1-piperazinyl)-9-chloro-5-methyl-6,7-dihydro-1-oxo-1H,5H-benzo[ij]quinolizine-2-carboxylic acid Melting point: 296° to 297° C.

EXAMPLE 70

8-(4-Heptafluorobutyryl-1-piperazinyl)-9-chloro-5-methyl-6,7-dihydro-1-oxo-1H,5H-benzo[ij]quinolizine-2-carboxylic acid Melting point: 269.5° to 270.5° C.

EXAMPLE 71

8-(4-Trifluoromethanesulfonyl-1-piperazinyl)-5-methyl-6,7-dihydro-1-oxo-1H,5H-benzo[ij]quinolizine-2-carboxylic acid Melting point: 232° to 235° C.

EXAMPLE 72

8-[4-(2-Hydroxyethyl)-1-piperazinyl]-9-fluoro-5-methyl-6,7-dihydro-1-oxo-1H,5H-benzo[ij]quinolizine-2-carboxylic acid Melting point: 288° to 290° C.

EXAMPLE 73

A mixture of 3.4 g of 8-(p-toluenesulfonyloxy)-6,7-dihydro-1-oxo-1H,5H-benzo[ij]quinolizine-2-carboxylic acid, 9.1 g of 1-trifluoromethylpiperazine and 200 ml of anhydrous dimethyl sulfoxide was heated with stirring in an autoclave at 150° to 160° C. for 18 hours under nitrogen gas flow at a pressure of 10 atms. After completion of the reaction, the solvent and excessive piperazine compound were removed by distillation under reduced pressure and a mixture of methanol and ethanol was added to the residue. The precipitates formed were collected by filtration and washed with ether. The crystals obtained were suspended in a mixture of 200 ml of water and 40 ml of a 10% aqueous hydrochloric acid solution and insoluble substances were removed by filtration. The filtrate was rendered neutral with saturated aqueous solution of sodium bicarbonate and purified through column chromatography using Amberlite LH-20 (a trade name for a product of Tokyo Organic Chemical Industries Ltd.) (eluent: water, ethanol). Recrystallization of the eluate from dimethylformamide gave 1.7 g of 8-(4-trifluoromethyl-1-piperazinyl)-6,7-dihydro-1-oxo-1H,5H-benzo[ij]quinolizine-2-carboxylic acid as white rhombic crystals having a melting point of 300° C. or more.

EXAMPLE 74

A mixture of 4.5 g of 8-(p-toluenesulfonyloxy)-9-chloro-5-methyl-6,7-dihydro-1-oxo-1H,5H-benzo[ij]-quinolizine-2-carboxylic acid, 9.1 g of 1-trifluoroacetyl-piperazine and 200 ml of anhydrous dimethyl sulfoxide was heated with stirring in an autoclave at 150° to 160° C. for 17 hours under nitrogen gas flow at a pressure of 10 atms. The reaction mixture was treated in the same manner as Example 73 to obtain 2.3 g of 8-(4-trifluoroacetyl-1-piperazinyl)-9-chloro-5-methyl-6,7-dihydro-1-oxo-1H,5H-benzo[ij]quinolizine-2-carboxylic acid as white rhombic crystals having a melting point of 300° C. or more.

EXAMPLE 75

A mixture of 3.37 g of 8-methanesulfonyloxy-6,7-dihydro-1-oxo-1H,5H-benzo[ij]quinolizine-2-carboxylic acid, 9.1 g of 1-trifluoromethylpiperazine and 200 ml of anhydrous dimethyl sulfoxide was heated with stirring in an autoclave at 170° to 180° C. for 20 hours under nitrogen gas flow at a pressure of 8 atms. The reaction mixture was treated in the same manner as in Example 73 and further treated with concentrated hydrochloric acid to obtain 1.7 g of 8-(4-trifluoromethyl-1-piperazinyl)-6,7-dihydro-1-oxo-1H,5H-benzo[ij]quinolizine-2-carboxylic acid hydrochloride as white rhombic crystals having a melting point of 300° C. or more.

PREPARATION EXAMPLE 1

| | |
|---|---|
| 8-(1-Piperazinyl)-6,7-dihydro-1-oxo-1H,5H—benzo[ij]quinolizine-2-carboxylic Acid Hydrochloride | 200 mg |
| Glucose | 250 mg |
| Distilled Water for Injection | q.s. to make 5 ml |

The active compound and glucose were dissolved in distilled water for injection, and the solution was poured into a 5 ml ampoule. The air was purged with nitrogen, and the ampoule was sealed and sterilized at 121° C. for 15 minutes to obtain an injectable preparation.

PREPARATION EXAMPLE 2

| | |
|---|---|
| 8-(1-Piperazinyl)-5-methyl-6,7-dihydro-1-oxo-1H,5H—benzo[ij]quinolizine-2-carboxylic Acid Hydrochloride | 100 g |
| Avicel (trade name for a product of Asahi Kasei Kogyo Kabushiki Kaisha) | 40 g |
| Corn Starch | 30 g |
| Magnesium Stearate | 2 g |
| TC-5 (trade name for hydroxypropyl-methyl cellulose, produced by Shinetsu Chemical Industry Co., Ltd.) | 10 g |
| Polyethylene Glycol-6000 (molecular weight: 6000) | 3 g |
| Castor Oil | 40 g |
| Methanol | 40 g |

The active compound, Avicel, corn starch and magnesium stearate were mixed and ground, and then tableted using a conventional pounder (R 10 mm) for sugar coating (produced by Kikusui Seisakusho Co., Ltd.). The resulting tablets were coated with a film coating agent composed of TC-5, polyethylene glycol-6000, castor oil and methanol to produce film-coated tablets.

PREPARATION EXAMPLE 3

| | |
|---|---|
| 8-(1-Piperazinyl)-6,7-dihydro-1-oxo-1H,5H—benzo[ij]quinolizine-2-carboxylic Acid | 2 g |
| Purified Hydrous Lanolin | 5 g |
| Japan Wax | 5 g |
| White Petrolatum | 88 g |

The Japan wax was heated until it was molten, and the active compound, purified hydrous lanolin, and white petrolatum were added thereto, followed by heat-melting. The mixture was stirred until it began to solidify to prepare an ointment.

PREPARATION EXAMPLE 4

| | |
|---|---|
| 9-(1-Piperazinyl)-6-oxo-1,2-dihydro-6H—pyrrolo[3,2,1-ij]quinoline-5-carboxylic Acid Hydrochloride | 200 mg |
| Glucose | 250 mg |
| Distilled Water for Injection | q.s. to make 5 ml |

The active compound and glucose were dissolved in distilled water for injection, and the solution was poured into a 5 ml ampoule. The air was purged with nitrogen, and the ampoule was sealed and sterilized at 121° C. for 15 minutes to obtain an injectable preparation.

PREPARATION EXAMPLE 5

| | |
|---|---|
| 9-(1-Piperazinyl)-2-methyl-6-oxo-1,2-dihydro-6H-pyrrolo[3,2,1-ij]-quinoline-5-carboxylic Acid Hydrochloride | 100 g |
| Avicel (trade name for a product of Asahi Kasei Kogyo Kabushiki Kaisha) | 40 g |
| Corn Starch | 30 g |
| Magnesium Stearate | 2 g |
| TC-5 (trade name for hydroxypropylmethyl cellulose, produced by Shinetsu Chemical Industry Co., Ltd.) | 10 g |

| | |
|---|---|
| Polyethylene Glycol-6000 (molecular weight: 6000) | 3 g |
| Castor Oil | 40 g |
| Methanol | 40 g |

The active compound, Avicel, corn starch and magnesium stearate were mixed and ground, and then tableted using a conventional pounder (R 10 mm) for sugar coating (produced by Kikusui Seisakusho Co., Ltd.). The resulting tablets were coated with a film coating agent composed of TC-5, polyethylene glycol-6000, castor oil and methanol to produce film-coated tablets.

PREPARATION EXAMPLE 6

| | |
|---|---|
| 1-(1-Piperazinyl)-7a,8,9,10,11,11a-hexahydro-4-oxo-4H-pyrido[3,2,1-ij]-carbazole-5-carboxylic Acid Hydrochloride | 100 g |
| Avicel (trade name for a product of Asahi Kasei Kogyo Kabushiki Kaisha) | 40 g |
| Corn Starch | 30 g |
| Magnesium Stearate | 2 g |
| TC-5 (trade name for hydroxypropylmethyl cellulose, produced by Shinetsu Chemical Industry Co., Ltd.) | 10 g |
| Polyethylene Glycol-6000 (molecular weight: 6000) | 3 g |
| Castor Oil | 40 g |
| Methanol | 40 g |

The active compound, Avicel, corn starch and magnesium stearate were mixed and ground, and then tableted using a conventional pounder (R 10 mm) for sugar coating (produced by Kikusui Seisakusho Co., Ltd.). The resulting tablets were coated with a film coating agent composed of TC-5, polyethylene glycol-6000, castor oil and methanol to produce film-coated tablets.

PREPARATION EXAMPLE 7

| | |
|---|---|
| 8-(4-Methyl-1-piperazinyl)-9-fluoro-5-methyl-6,7-dihydro-1-oxo-1H,5H-benzo[ij]quinolizine-2-carboxylic Acid Hydrochloride | 100 g |
| Avicel (trade name for a product of Asahi Kasei Kogyo Kaisha) | 40 g |
| Corn Starch | 30 g |
| Magnesium Stearate | 2 g |
| TC-5 (trade name for hydroxypropylmethyl cellulose, produced by Shinetsu Chemical Industry Co., Ltd.) | 10 g |
| Polyethylene Glycol-6000 (molecular weight: 6000) | 3 g |
| Castor Oil | 40 g |
| Methanol | 40 g |

The active compound, Avicel, corn starch and magnesium stearate were mixed and ground, and then tableted using a conventional pounder (R 10 mm) for sugar coating (produced by Kikusui Seisakusho Co., Ltd.). The resulting tablets were coated with a film coating agent composed of TC-5, polyethylene glycol-6000, castor oil and methanol to produce film-coated tablets.

PREPARATION EXAMPLE 8

| | |
|---|---|
| 8-Fluoro-9-(4-methyl-1-piperazinyl)-2-methyl-6-oxo-1,2-dihydro-6H-pyrrolo[3,2,1-ij]quinoline-5-carboxylic Acid | 100 g |
| Avicel (trade name for a product of Asahi Kasei Kogyo Kabushiki Kaisha) | 40 g |
| Corn Starch | 30 g |
| Magnesium Stearate | 2 g |
| TC-5 (trade name for hydroxypropylmethyl cellulose, produced by Shinetsu Chemical Industry Co., Ltd.) | 10 g |
| Polyethylene Glycol-6000 (molecular weight: 6000) | 3 g |
| Castor Oil | 40 g |
| Methanol | 40 g |

The active compound, Avicel, corn starch and magnesium stearate were mixed and ground, and then tableted using a conventional pounder (R 10 mm) for sugar coating (produced by Kikusui Seisakusho Co., Ltd.). The resulting tablets were coated with a film coating agent composed of TC-5, polyethylene glycol-6000, castor oil and methanol to produce film-coated tablets.

PREPARATION EXAMPLE 9

| | |
|---|---|
| 8-(4-Trifluoroacetyl-1-piperazinyl)-9-chloro-5-methyl-6,7-dihydro-1-oxo-1H,5H—benzo[ij]quinolizine-2-carboxylic Acid Hydrochloride | 200 mg |
| Glucose | 250 mg |
| Distilled Water for Injection | q.s. to make 5 ml |

The active compound and glucose were dissolved in distilled water for injection, and the solution was poured into a 5 ml ampoule. The air was purged with nitrogen, and the ampoule was sealed and sterilized at 121° C. for 15 minutes to obtain an injectable preparation.

PREPARATION EXAMPLE 10

| | |
|---|---|
| 8-(4-Trifluoroacetyl-1-piperazinyl)-9-chloro-5-methyl-6,7-dihydro-1-oxo-1H,5H—benzo[ij]quinolizine-2-carboxylic Acid | 100 g |
| Avicel (trade name for a product of Asahi Kasei Kogyo Kabushiki Kaisha) | 40 g |
| Corn Starch | 30 g |
| Magnesium Stearate | 2 g |
| TC-5 (trade name for hydroxypropylmethyl cellulose, produced by Shinetsu Chemical Industry Co., Ltd.) | 10 g |
| Polyethylene Glycol-6000 (molecular weight: 6000) | 3 g |
| Castor Oil | 40 g |
| Methanol | 40 g |

The active compound, Avicel, corn starch and magnesium stearate were mixed and ground, and then tableted using a conventional pounder (R 10 mm) for sugar coating (produced by Kikusui Seisakusho Co., Ltd.). The resulting tablets were coated with a film coating agent composed of TC-5, polyethylene glycol-6000, castor oil and methanol to produce film-coated tablets.

PREPARATION EXAMPLE 11

| | |
|---|---|
| 8-(4-Trifluoroacetyl-1-piperazinyl)-9-chloro-5-methyl-6,7-dihydro-1-oxo-1H,5H—benzo[ij]quinolizine-2-carboxylic Acid | 2 g |
| Purified Hydrous Lanolin | 5 g |
| Japan Wax | 5 g |

| -continued | |
|---|---|
| White Petrolatum | 88 g |
| | Total: 100 g |

The Japan wax was heated until molten, and the active compound, purified hydrous lanolin and white petrolatum were added thereto followed by heat-melting. The mixture was stirred until it began to solidify to prepare an ointment.

While the invention has been described in detail and with reference to specific embodiments thereof, it will be apparent to one skilled in the art that various changes and modifications can be made therein without departing from the spirit and scope thereof.

What is claimed is:

1. A piperazinylbenzoheterocyclic compound represented by the formula (I)

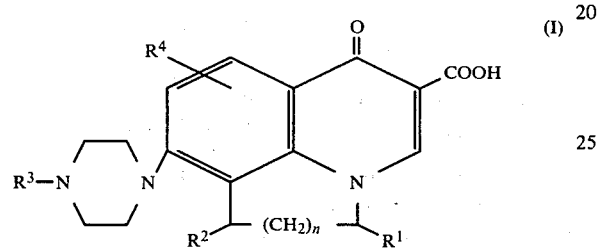

wherein $R^1$ represents hydrogen or lower alkyl; $R^2$ represents hydrogen; $R^3$ represents hydrogen, lower alkyl, lower alkanoyl, lower alkylsulfonyl, phenylalkyl wherein the alkyl moiety contains 1 to 4 carbon atoms, benzoyl, p-toluenesulfonyl, a group represented by the formula

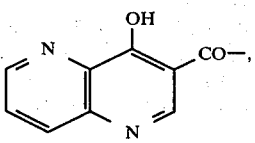

lower alkyl substituted with one to three of halogen and hydroxy, lower alkanoyl substituted with one to seven of halogen selected from the group consisting of fluorine, chlorine and bromine, phenylalkyl substituted with one to three of lower alkoxy on the phenyl ring, lower alkylsulfonyl substituted with one to three of halogen, lower alkenyl or lower alkynyl; $R^4$ represents hydrogen or halogen, and n is an integer of 0 or 1, except that when n is 0, $R^1$ and $R^2$ together can represent the atoms necessary to form a cyclohexane ring, and when $R^3$ represents lower alkyl substituted with one to three of halogen and hydroxy, lower alkanoyl substituted with one to seven of halogen selected from the group consisting of fluorine, chlorine and bromine, phenylalkyl substituted with one to three of lower alkoxy on the phenyl ring, lower alkylsulfonyl substituted with one to three of halogen, lower alkenyl or lower alkynyl, n is 1; or a pharmaceutically acceptable salt thereof.

2. A piperazinylbenzoheterocyclic compound or pharmaceutically acceptable salt thereof as in claim 1 wherein n is 1.

3. A piperazinylbenzoheterocyclic compound or a pharmaceutically acceptable salt thereof as in claim 2 wherein $R^4$ represents halogen.

4. A piperazinylbenzoheterocyclic compound or a pharmaceutically acceptable salt thereof as in claim 3 wherein $R^4$ represents chlorine or fluorine.

5. A piperazinylbenzoheterocyclic compound or a pharmaceutically acceptable salt thereof as in claim 4 wherein $R^1$ represents alkyl having from 1 to 4 carbon atoms.

6. A piperazinylbenzoheterocyclic compound or a pharmaceutically acceptable salt thereof as in claim 5 wherein $R^3$ represents hydrogen, alkyl having from 1 to 4 carbon atoms or alkanoyl having from 1 to 4 carbon atoms.

7. A piperazinylbenzoheterocyclic compound or a pharmaceutically acceptable salt thereof as in claim 5 wherein $R^3$ represents alkylsulfonyl having from 1 to 4 carbon atoms, phenylalkyl consisting of phenyl and alkyl having from 1 to 4 carbon atoms, benzoyl group, p-toluenesulfonyl or a group represented by the formula

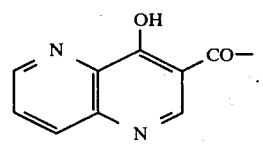

8. A piperazinylbenzoheterocyclic compound or a pharmaceutically acceptable salt thereof as in claim 5 wherein $R^3$ represents alkyl having from 1 to 4 carbon atoms substituted with from 1 to 3 of halogen and hydroxy or alkanoyl having from 1 to 4 carbon atoms substituted with from 1 to 7 of halogen.

9. A piperazinylbenzoheterocyclic compound or a pharmaceutically acceptable salt thereof as in claim 5 wherein $R^3$ represents phenylalkyl consisting of phenyl substituted with from 1 to 3 of alkoxy each having from 1 to 4 carbon atoms and alkylene having from 1 to 4 carbon atoms, alkylsulfonyl having from 1 to 4 carbon atoms substituted with from 1 to 3 of halogen, alkenyl having from 2 to 4 carbon atoms, or alkynyl having from 2 to 4 carbon atoms.

10. A piperazinylbenzoheterocyclic compound or a pharmaceutically acceptable salt thereof as in claim 4 wherein $R^1$ represents hydrogen.

11. A piperazinylbenzoheterocyclic compound or a pharmaceutically acceptable salt thereof as in claim 10 wherein $R^3$ represents hydrogen, alkyl having from 1 to 4 carbon atoms, or alkanoyl having from 1 to 4 carbon atoms.

12. A piperazinylbenzoheterocyclic compound or a pharmaceutically acceptable salt thereof as in claim 2 wherein $R^4$ represents hydrogen.

13. A piperazinylbenzoheterocyclic compound or a pharmaceutically acceptable salt thereof as in claim 12 wherein $R^1$ represents alkyl having from 1 to 4 carbon atoms.

14. A piperazinylbenzoheterocyclic compound or a pharmaceutically acceptable salt thereof as in claim 13 wherein $R^3$ represents hydrogen, alkyl having from 1 to 4 carbon atoms or alkanoyl having from 1 to 4 carbon atoms.

15. A piperazinylbenzoheterocyclic compound or a pharmaceutically acceptable salt thereof as in claim 12 wherein $R^1$ represents hydrogen.

16. A piperazinylbenzoheterocyclic compound or a pharmaceutically acceptable salt thereof as in claim 1 wherein n is 0, $R^1$ represents hydrogen or lower alkyl, and $R^2$ represents hydrogen.

17. A piperazinylbenzoheterocyclic compound or a pharmaceutically acceptable salt thereof as in claim 16 wherein $R^4$ represents halogen.

18. A piperazinylbenzoheterocyclic compound or a pharmaceutically acceptable salt thereof as in claim 17 wherein $R^1$ represents alkyl having from 1 to 4 carbon atoms.

19. A piperazinylbenzoheterocyclic compound or a pharmaceutically acceptable salt thereof as in claim 18 wherein $R^3$ represents hydrogen, alkyl having from 1 to 4 carbon atoms, or alkanoyl having from 1 to 4 carbon atoms.

20. A piperazinylbenzoheterocyclic compound or a pharmaceutically acceptable salt thereof as in claim 18 wherein $R^3$ represents alkylsulfonyl having from 1 to 4 carbon atoms, phenylalkyl consisting of phenyl and alkylene having from 1 to 4 carbon atoms, a benzoyl group, a p-toluenesulfonyl group or a group represented by the formula

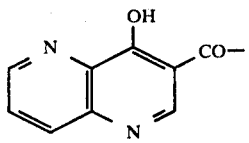

21. A piperazinylbenzoheterocyclic compound or a pharmaceutically acceptable salt thereof as in claim 17 wherein $R^1$ represents hydrogen.

22. A piperazinylbenzoheterocyclic compound or a pharmaceutically acceptable salt thereof as in claim 21 wherein $R^3$ represents hydrogen, alkyl having from 1 to 4 carbon atoms, or alkanoyl having from 1 to 4 carbon atoms.

23. A piperazinylbenzoheterocyclic compound or a pharmaceutically acceptable salt thereof as in claim 16 wherein $R^4$ represents hydrogen.

24. A piperazinylbenzoheterocyclic compound or a pharmaceutically acceptable salt thereof as in claim 23 wherein $R^1$ represents alkyl having from 1 to 4 carbon atoms.

25. A piperazinylbenzoheterocyclic compound or a pharmaceutically acceptable salt thereof as in claim 24 wherein $R^3$ represents hydrogen, alkyl having from 1 to 4 carbon atoms, or alkanoyl having from 1 to 4 carbon atoms.

26. A piperazinylbenzoheterocyclic compound or a pharmaceutically acceptable salt thereof as in claim 23 wherein $R^1$ represents hydrogen.

27. A piperazinylbenzoheterocyclic compound or a pharmaceutically acceptable salt thereof as in claim 1 wherein n is 0 and $R^1$ and $R^2$ together represent the atoms necessary to form a cyclohexane ring.

28. A piperazinylbenzoheterocyclic compound or a pharmaceutically acceptable salt thereof as in claim 14 wherein said compound is 8-(1-piperazinyl)-5-methyl-6,7-dihydro-1-oxo-1H,5H-benzo[ij]quinolizine-2-carboxylic acid.

29. A piperazinylbenzoheterocyclic compound or a pharmaceutically acceptable salt thereof as in claim 25 wherein said compound is 9-(1-piperazinyl)-2-methyl-6-oxo-1,2-dihydro-6H-pyrrolo[3,2,1-ij]quinoline-5-carboxylic acid.

30. A piperazinylbenzoheterocyclic compound or a pharmaceutically acceptable salt thereof as in claim 15 wherein said compound is 8-(1-piperazinyl)-6,7-dihydro-1-oxo-1H,5H-benzo[ij]quinolizine-2-carboxylic acid.

31. A piperazinylbenzoheterocyclic compound or a pharmaceutically acceptable salt thereof as in claim 26 wherein said compound is 9-(1-piperazinyl)-6-oxo-1,2-dihydro-6H-pyrrolo[3,2,1-ij]quinoline-5-carboxylic acid.

32. A piperazinylbenzoheterocyclic compound or a pharmaceutically acceptable salt thereof as in claim 27 wherein said compound is 1-(1-piperazinyl)-7a,8,9,10,11,11a-hexahydro-4H-pyrido[3,2,1-jk]carbazole-4-oxo-5-carboxylic acid.

33. A piperazinylbenzoheterocyclic compound or a pharmaceutically acceptable salt thereof as in claim 6 wherein said compound is 8-(1-piperazinyl)-9-fluoro-5-methyl-6,7-dihydro-1-oxo-1H,5H-benzo[ij]quinolizine-2-carboxylic acid.

34. A piperazinylbenzoheterocyclic compound or a pharmaceutically acceptable salt thereof as in claim 6 wherein said compound is 8-(1-piperazinyl)-9-chloro-5-methyl-6,7-dihydro-1-oxo-1H,5H-benzo[ij]quinolizine-2-carboxylic acid.

35. A piperazinylbenzoheterocyclic compound or a pharmaceutically acceptable salt thereof as in claim 6 wherein said compound is 8-(4-methyl-1-piperazinyl)-9-chloro-5-methyl-6,7-dihydro-1-oxo-1H,5H-benzo[ij]quinolizine-2-carboxylic acid.

36. A piperazinylbenzoheterocyclic compound or a pharmaceutically acceptable salt thereof as in claim 6 wherein said compound is 8-(4-formyl-1-piperazinyl)-9-chloro-5-methyl-6,7-dihydro-1-oxo-1H,5H-benzo[ij]quinolizine-2-carboxylic acid.

37. A piperazinylbenzoheterocyclic compound or a pharmaceutically acceptable salt thereof as in claim 6 wherein said compound is 8-(4-methyl-1-piperazinyl)-9-fluoro-5-methyl-6,7-dihydro-1-oxo-1H,5H-benzo[ij]quinolizine-2-carboxylic acid.

38. A piperazinylbenzoheterocyclic compound or a pharmaceutically acceptable salt thereof as in claim 6 wherein said compound is 8-(4-formyl-1-piperazinyl)-9-fluoro-5-methyl-6,7-dihydro-1-oxo-1H,5H-benzo[ij]quinolizine-2-carboxylic acid.

39. A piperazinylbenzoheterocyclic compound or a pharmaceutically acceptable salt thereof as in claim 6 wherein said compound is 8-(4-acetyl-1-piperazinyl)-9-fluoro-5-methyl-6,7-dihydro-1-oxo-1H,5H-benzo[ij]quinolizine-2-carboxylic acid.

40. A piperazinylbenzoheterocyclic compound or a pharmaceutically acceptable salt thereof as in claim 6 wherein said compound is 8-(4-ethyl-1-piperazinyl)-9-fluoro-5-methyl-6,7-dihydro-1-oxo-1H,5H-benzo[ij]quinolizine-2-carboxylic acid.

41. A piperazinylbenzoheterocyclic compound or a pharmaceutically acceptable salt thereof as in claim 19 wherein said compound is 8-chloro-9-(1-piperazinyl)-2-methyl-6-oxo-1,2-dihydro-6H-pyrrolo[3,2,1-ij]quinoline-5-carboxylic acid.

42. A piperazinylbenzoheterocyclic compound or a pharmaceutically acceptable salt thereof as in claim 19 wherein said compound is 8-chloro-9-(4-methyl-1-piperazinyl)-2-methyl-6-oxo-1,2-dihydro-6H-pyrrolo[3,2,1-ij]quinoline-5-carboxylic acid.

43. A piperazinylbenzoheterocyclic compound or a pharmaceutically acceptable salt thereof as in claim 19 wherein said compound is 8-chloro-9-(4-formyl-1-piperazinyl)-2-methyl-6-oxo-1,2-dihydro-6H-pyrrolo[3,2,1-ij]quinoline-5-carboxylic acid.

44. A piperazinylbenzoheterocyclic compound or a pharmaceutically acceptable salt thereof as in claim 19 wherein said compound is 8-chloro-9-(4-acetyl-1-piperazinyl)-2-methyl-6-oxo-1,2-dihydro-6H-pyrrolo-[3,2,1-ij]quinoline-5-carboxylic acid.

45. A piperazinylbenzoheterocyclic compound or a pharmaceutically acceptable salt thereof as in claim 19 wherein said compound is 8-fluoro-9-(1-piperazinyl)-2-methyl-6-oxo-1,2-dihydro-6H-pyrrolo[3,2,1-ij]quinoline-5-carboxylic acid.

46. A piperazinylbenzoheterocyclic compound or a pharmaceutically acceptable salt thereof as in claim 19 wherein said compound is 8-fluoro-9-(4-formyl-1-piperazinyl)-2-methyl-6-oxo-1,2-dihydro-6H-pyrrolo-[3,2,1-ij]quinoline-5-carboxylic acid.

47. A piperazinylbenzoheterocyclic compound or a pharmaceutically acceptable salt thereof as in claim 8 wherein said compound is 8-(4-trifluoroacetyl-1-piperazinyl)-9-chloro-5-methyl-6,7-dihydro-1-oxo-1H,5H-benzo[ij]quinolizine-2-carboxylic acid.

48. A piperazinylbenzoheterocyclic compound or a pharmaceutically acceptable salt thereof as in claim 8 wherein said compound is 8-[4-(2,2,2-trifluoroethyl)-1-piperazinyl]-9-chloro-5-methyl-6,7-dihydro-1-oxo-1H,5H-benzo[ij]quinolizine-2-carboxylic acid.

49. A piperazinylbenzoheterocyclic compound or a pharmaceutically acceptable salt thereof as in claim 8 wherein said compound is 8-[4-(2-hydroxyethyl)-1-piperazinyl]-9-fluoro-5-methyl-6,7-dihydro-1-oxo-1H,5H-benzo[ij]quinolizine-2-carboxylic acid.

50. A piperazinylbenzoheterocyclic compound or a pharmaceutically acceptable salt thereof as in claim 19 wherein said compound is 8-Fluoro-9-(4-methyl-1-piperazinyl)-2-methyl-6-oxo-1,2-dihydro-6H-pyrrolo[3,2,1-ij]quinoline-5-carboxylic acid.

51. A compound selected from the group consisting of 9-fluoro-6,7-dihydro-5-methyl-1-oxo-8-(1-piperazinyl)-1H,5H-benzo-[ij]quinolizine-2-carboxylic acid; 9-fluoro-6,7-dihydro-5-methyl-1-oxo-8-(4-methyl-1-piperazinyl)1H,5H-benzo[ij]quinolizine-2-carboxylic acid and the pharmaceutically acceptable acid addition salts thereof.

52. A piperazinylbenzoheterocyclic compound or a pharmaceutically acceptable salt thereof as in claim 1, wherein R³ represents hydrogen, lower alkyl, lower alkanoyl, lower alkylsulfonyl, phenylalkyl having 1 to 4 carbon atoms in the alkyl moiety, benzoyl, p-toluenesulfonyl or a group represented by the formula

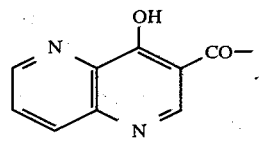

53. The piperazinylbenzoheterocyclic compound or pharmaceutically acceptable salt of claim 52, wherein R³ represents hydrogen.

54. The piperazinylbenzoheterocyclic compound or pharmaceutically acceptable salt of claim 53, wherein R⁴ represents hydrogen.

55. The piperazinylbenzoheterocyclic compound or pharmaceutically acceptable salt of claim 54, wherein R¹ represents alkyl having 1 to 4 carbon atoms.

56. The piperazinylbenzoheterocyclic compound or pharmaceutically acceptable salt of claim 54, wherein R¹ represents hydrogen.

57. The piperazinylbenzoheterocyclic compound or pharmaceutically acceptable salt of claim 53, wherein R⁴ represents halogen.

58. The piperazinylbenzoheterocyclic compound or pharmaceutically acceptable salt of claim 57, wherein R¹ represents alkyl having 1 to 4 carbon atoms.

59. The piperazinylbenzoheterocyclic compound or pharmaceutically acceptable salt of claim 52, wherein R³ represents lower alkyl, lower alkanoyl, lower alkylsulfonyl, phenylalkyl having 1 to 4 carbon atoms in the alkyl moiety, benzoyl, p-toluenesulfonyl or a group represented by the formula

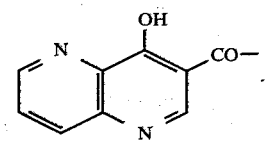

60. An antimicrobial composition comprising an antimicrobially effective amount of a piperazinylbenzoheterocyclic compound of claim 1.

61. An antimicrobial composition as in claim 60 wherein n is 1.

62. An antimicrobial composition as in claim 60 wherein n is 0, R¹ represents hydrogen or lower alkyl, and R² represents hydrogen atom.

63. An antimicrobial composition as in claim 60 wherein n is 0 and R¹ and R² together represent the atoms necessary to form a cyclohexane ring.

64. An antimicrobial composition as in claim 60, wherein R³ represents hydrogen, lower alkyl, lower alkanoyl, lower alkylsulfonyl, phenylalkyl having 1 to 4 carbon atoms in the alkyl moiety, benzoyl, p-toluenesulfonyl or a group represents by the formula

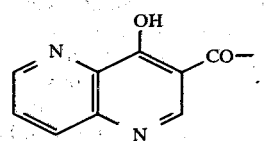

* * * * *